(12) United States Patent
Mori et al.

(10) Patent No.: US 7,763,716 B2
(45) Date of Patent: Jul. 27, 2010

(54) ANTIBODY AGAINST NPW

(75) Inventors: Masaaki Mori, Osaka (JP); Yukio Shimomura, Tsukuba (JP)

(73) Assignee: Takeda Pharmaceutical Company Limited, Osaka-Shi (JP)

( * ) Notice: Subject to any disclaimer, the term of this patent is extended or adjusted under 35 U.S.C. 154(b) by 761 days.

(21) Appl. No.: 10/557,351

(22) PCT Filed: May 27, 2004

(86) PCT No.: PCT/JP2004/007667

§ 371 (c)(1),
(2), (4) Date: Nov. 18, 2005

(87) PCT Pub. No.: WO2004/106382

PCT Pub. Date: Dec. 9, 2004

(65) Prior Publication Data

US 2007/0082364 A1    Apr. 12, 2007

(30) Foreign Application Priority Data

May 28, 2003    (JP)    .............................. 2003-151577

(51) Int. Cl.
*C07K 16/18*    (2006.01)

(52) U.S. Cl. .................................... 530/387.1

(58) Field of Classification Search .................... None
See application file for complete search history.

(56) References Cited

FOREIGN PATENT DOCUMENTS

| | | |
|---|---|---|
| EP | 1 293 567 A1 | 3/2003 |
| WO | WO 01/98494 A1 | 12/2001 |
| WO | WO 02/102847 A1 | 12/2002 |
| WO | WO 03/057236 A1 | 7/2003 |
| WO | WO 2004/041301 A1 | 5/2004 |
| WO | WO 2004/080485 A1 | 9/2004 |

OTHER PUBLICATIONS

Mondal et al., "A role for neuropeptide W in the regulation of feeding behavior", Endocrinology, 144(11):4729-4733 (2003).
Shimomura et al., "Identification of neuropeptide W as the endogenous ligand for orphan G-protein-coupled receptors GPR7 and GPR8", Journal of Biological Chemistry, American Society of Biolochemical Biologists, 277(39):35826-35832 (2002).

*Primary Examiner*—Michael Pak
(74) *Attorney, Agent, or Firm*—Edwards Angell Palmer & Dodge LLP; David G. Conlin; Jonathan M. Sparks

(57) ABSTRACT

The antibody of the present invention, which specifically reacts with a partial peptide at the N-terminal region or the C-terminal region of NPW, which enables to quantify NPW with highly sensitivity and specifically. Moreover, this antibody is useful as an agent for preventing/treating infertility, renal edema, digestive ulcer, gastric hyperacidity, etc., and a diagnostic for these diseases.

11 Claims, 28 Drawing Sheets

ANTIBODY AGAINST NPW

TECHNICAL FIELD

The present invention relates to a novel antibody having a binding specificity to a polypeptide comprising an amino acid sequence represented by SEQ ID NO: 4, SEQ ID NO: 5, SEQ ID NO: 6, SEQ ID NO: 7, SEQ ID NO: 8, SEQ ID NO: 9, SEQ ID NO: 10 or SEQ ID NO: 11, or a salt thereof. More particularly, the present invention relates to a method of quantifying the polypeptide or a salt thereof based on an antigen-antibody reaction, an antibody useful for diagnosis of diseases associated with the polypeptide or a salt thereof (e.g., anorexia, obesity, renal dropsy, syndrome of inappropriate secretion of anti-diuretic hormone, diabetes insipidus, upper digestive tract disorders, hyperchlorhydria, etc.) utilizing the neutralizing activity, and for development of preventive/therapeutic agents for these diseases, and so on.

BACKGROUND ART

As the endogenous ligands for human GPR7 and human GPR8 (Genomics, 28, 84-91, 1995, WO 95/12670), which are G protein-coupled receptors, the ligands for GPR8 (sometimes referred to as NPW or neuropeptide W in the specification) were isolated and identified (WO 01/98494, WO 02/44368, J. Biol. Chem., 277, 35826-35832, 2002). In addition, NPW was shown to be the ligand for rat or mouse GPR7 (the same receptor as TGR26 described in WO 02/44368) (WO 02/44368, J. Biol. Chem., 277, 35826-35832, 2002). As physiological actions of NPW, the action of increasing food intake, the action of stimulating prolactin release, etc. by intracerebroventricular administration are known (WO 01/98494, J. Biol. Chem., 277, 35826-35832, 2002).

Further studies about the physiological actions of NPW or the involvement of NPW in diseases are required, and an assay system for detecting and quantifying NPW in a simple way with high sensitivity has been earnestly desired.

DISCLOSURE OF THE INVENTION

The present inventors have made extensive investigations to solve the foregoing problems and as a result, produced a plurality of monoclonal antibodies capable of recognizing NPW and also found that the antibodies have an excellent activity of neutralizing NPW, resulting in development of an excellent method for assaying NPW using these antibodies. The inventors have made further investigations and come to accomplish the present invention.

That is, the present invention relates to:

(1) An antibody specifically reacting with a partial peptide at the N-terminal region of a polypeptide or a salt thereof, wherein the polypeptide comprises the amino acid sequence represented by SEQ ID NO: 4, SEQ ID NO: 5, SEQ ID NO: 6, SEQ ID NO: 7, SEQ ID NO: 8, SEQ ID NO: 9, SEQ ID NO: 10 or SEQ ID NO: 11, (2) The antibody according to (1), which specifically reacts with a peptide comprising the 1st-13th amino acid sequence in the amino acid sequence represented by SEQ ID NO: 4, SEQ ID NO: 5, SEQ ID NO: 6, SEQ ID NO: 7, SEQ ID NO: 8, SEQ ID NO: 9, SEQ ID NO: 10 or SEQ ID NO: 11, (2a) The antibody according to (2), which has a neutralizing activity for a peptide comprising the amino acid sequence represented by SEQ ID NO: 4, SEQ ID NO: 5, SEQ ID NO: 6, SEQ ID NO: 7, SEQ ID NO: 8, SEQ ID NO: 9, SEQ ID NO: 10 or SEQ ID NO: 11, (3) The antibody according to (1), which specifically reacts with a peptide comprising at least one selected from the 1st-3rd, 1st-4th, 1st-5th, 1st-6th, 1st-7th, 1st-8th, 1st-9th, 2nd-4th, 2nd-5th, 2nd-6th, 2nd-7th, 2nd-8th, 2nd-9th, 3rd-5th, 3rd-6th, 3rd-7th, 3rd-8th, 3rd-9th, 4th-6th, 4th-7th, 4th-8th, 4th-9th, 5th-7th, 5th-8th, 5th-9th, 6th-8th, 6th-9th and 7th-9th amino acid sequences in the amino acid sequence represented by SEQ ID NO: 4, SEQ ID NO: 5, SEQ ID NO: 6, SEQ ID NO: 7, SEQ ID NO: 8, SEQ ID NO: 9, SEQ ID NO: 10 or SEQ ID NO: 11, (3a) The antibody according to (3), which has a neutralizing activity for a peptide comprising the amino acid sequence represented by SEQ ID NO: 4, SEQ ID NO: 5, SEQ ID NO: 6, SEQ ID NO: 7, SEQ ID NO: 8, SEQ ID NO: 9, SEQ ID NO: 10 or SEQ ID NO: 11, (4) The antibody according to (1), which does not recognize the partial peptide at the C-terminal region of a polypeptide or a salt thereof, wherein the polypeptide comprises the amino acid sequence represented by SEQ ID NO: 4, SEQ ID NO: 5, SEQ ID NO: 6, SEQ ID NO: 7, SEQ ID NO: 8, SEQ ID NO: 9, SEQ ID NO: 10 or SEQ ID NO: 11, (5) The antibody according to (1), which has a neutralizing activity for a peptide comprising the amino acid sequence represented by SEQ ID NO: 4, SEQ ID NO: 5, SEQ ID NO: 6, SEQ ID NO: 7, SEQ ID NO: 8, SEQ ID NO: 9, SEQ ID NO: 10 or SEQ ID NO: 11, (6) The antibody according to (1), which is labeled, (7) The antibody according to (1), which is a monoclonal antibody, (8) The antibody according to (7), which is represented by AhW23N2G6D1a producible from a hybridoma represented by AhW23N2G6D1 (FERM BP-8363), (9) An antibody specifically reacting with a binding site of the antibody according to (8) to a polypeptide comprising the amino acid sequence represented by SEQ ID NO: 4, SEQ ID NO: 5, SEQ ID NO: 6, SEQ ID NO: 7, SEQ ID NO: 8, SEQ ID NO: 9, SEQ ID NO: 10 or SEQ ID NO: 11,

(10) The antibody according to (9), which has a neutralizing activity for a polypeptide comprising the amino acid sequence represented by SEQ ID NO: 4, SEQ ID NO: 5, SEQ ID NO: 6, SEQ ID NO: 7, SEQ ID NO: 8, SEQ ID NO: 9, SEQ ID NO: 10 or SEQ ID NO: 11,

(11) The antibody according to (7), which is represented by AhW23N3H3E4a producible from a hybridoma represented by AhW23N3H3E4 (FERM BP-8364),

(12) An antibody specifically reacting with a binding site of the antibody according to (11) to a polypeptide comprising the amino acid sequence represented by SEQ ID NO: 4, SEQ ID NO: 5, SEQ ID NO: 6, SEQ ID NO: 7, SEQ ID NO: 8, SEQ ID NO: 9, SEQ ID NO: 10 or SEQ ID NO: 11,

(13) The antibody according to (12), which has a neutralizing activity for a polypeptide comprising the amino acid sequence represented by SEQ ID NO: 4, SEQ ID NO: 5, SEQ ID NO: 6, SEQ ID NO: 7, SEQ ID NO: 8, SEQ ID NO: 9, SEQ ID NO: 10 or SEQ ID NO: 11,

(14) An antibody specifically reacting with a partial peptide at the C-terminal region of a polypeptide or a salt thereof, wherein the polypeptide comprises the amino acid sequence represented by SEQ ID NO: 4, SEQ ID NO: 6, SEQ ID NO: 8 or SEQ ID NO: 10,

(15) The antibody according to (14), which specifically reacts with a peptide comprising the 11th-23rd amino acid sequence in the amino acid sequence represented by SEQ ID NO: 4, SEQ ID NO: 6, SEQ ID NO: 8 or SEQ ID NO: 10, (15a) The antibody according to (15), which has a neutralizing activity for a peptide comprising the amino acid sequence represented by SEQ ID NO: 4, SEQ ID NO: 6, SEQ ID NO: 8 or SEQ ID NO: 10,

(16) The antibody according to (14), which specifically reacts with a peptide comprising at least one selected from the 16th-23rd, 17th-23rd, 18th-23rd, 19th-23rd, 20th-23rd, 21st-23rd, 16th-22nd, 17th-22nd, 18th-22nd, 19th-22nd, 20th-22nd, 16th-21st, 17th-21st, 18th-21st, 19th-21st, 16th-20th, 17th-20th and 18th-20th amino acid sequences in the amino acid sequence represented by SEQ ID NO: 4, SEQ ID NO: 6, SEQ ID NO: 8 or SEQ ID NO: 10, (16a) The antibody according to (16), which has a neutralizing activity for a peptide comprising the amino acid sequence represented by SEQ ID NO: 4, SEQ ID NO: 6, SEQ ID NO: 8 or SEQ ID NO: 10,

(17) The antibody according to (14), which does not recognize the partial peptide at the N-terminal region of a polypeptide or a salt thereof, wherein the polypeptide comprises the amino acid sequence represented by SEQ ID NO: 4, SEQ ID NO: 6, SEQ ID NO: 8 or SEQ ID NO: 10,

(18) The antibody according to (14), which has a neutralizing activity for a peptide comprising the amino acid sequence represented by SEQ ID NO: 4, SEQ ID NO: 6, SEQ ID NO: 8 or SEQ ID NO: 10,

(19) The antibody according to (14), which is labeled,

(20) The antibody according to (14), which is a monoclonal antibody,

(21) The antibody according to (20), which is represented by AhW23C6G1H8a producible from a hybridoma represented by AhW23C6G1H8 (FERM BP-8365),

(22) An antibody specifically reacting with a binding site of the antibody according to (21) to a polypeptide comprising the amino acid sequence represented by SEQ ID NO: 4, SEQ ID NO: 6, SEQ ID NO: 8 or SEQ ID NO: 10,

(23) The antibody according to (22), which has a neutralizing activity for a polypeptide comprising the amino acid sequence represented by SEQ ID NO: 4, SEQ ID NO: 6, SEQ ID NO: 8 or SEQ ID NO: 10,

(24) The antibody according to (20), which is represented by AhW23C5G2F6a producible from a hybridoma represented by AhW23C5G2F6 (FERM BP-8366),

(25) An antibody specifically reacting with a binding site of the antibody according to (24) to a polypeptide comprising the amino acid sequence represented by SEQ ID NO: 4, SEQ ID NO: 6, SEQ ID NO: 8 or SEQ ID NO: 10,

(26) The antibody according to (25), which has a neutralizing activity for a polypeptide comprising the amino acid sequence represented by SEQ ID NO: 4, SEQ ID NO: 6, SEQ ID NO: 8 or SEQ ID NO: 10,

(27) An antibody specifically reacting with a partial peptide at the C-terminal region of a polypeptide or a salt thereof, wherein the polypeptide comprises the amino acid sequence represented by SEQ ID NO: 5, SEQ ID NO: 7, SEQ ID NO: 9 or SEQ ID NO: 11,

(28) The antibody according to (27), which specifically reacts with a peptide comprising the 16th-30th amino acid sequence in the amino acid sequence represented by SEQ ID NO: 5, SEQ ID NO: 7, SEQ ID NO: 9 or SEQ ID NO: 11, (28a) The antibody according to (28), which has a neutralizing activity for a peptide comprising the amino acid sequence represented by SEQ ID NO: 5, SEQ ID NO: 7, SEQ ID NO: 9 or SEQ ID NO: 11,

(29) The antibody according to (27), which specifically reacts with a peptide comprising at least one selected from the 23rd-30th, 24th-30th, 25th-30th, 26th-30th, 27th-30th, 28th-30th, 23rd-29th, 24th-29th, 25th-29th, 26th-29th, 27th-29th, 23rd-28th, 24th-28th, 25th-28th, 26th-28th, 23rd-27th, 24th-27th and 25th-27th amino acid sequences in the amino acid sequence represented by SEQ ID NO: 5, SEQ ID NO: 7, SEQ ID NO: 9 or SEQ ID NO: 11, (29a) The antibody according to (29), which has a neutralizing activity for a peptide comprising the amino acid sequence represented by SEQ ID NO: 5, SEQ ID NO: 7, SEQ ID NO: 9 or SEQ ID NO: 11,

(30) The antibody according to (27), which does not recognize the partial peptide at the N-terminal region of a polypeptide or a salt thereof, wherein the polypeptide comprises the amino acid sequence represented by SEQ ID NO: 5, SEQ ID NO: 7, SEQ ID NO: 9 or SEQ ID NO: 11,

(31) The antibody according to (27), which has a neutralizing activity for a peptide comprising the amino acid sequence represented by SEQ ID NO: 5, SEQ ID NO: 7, SEQ ID NO: 9 or SEQ ID NO: 11,

(32) The antibody according to (27), which is labeled,

(33) The antibody according to (27), which is a monoclonal antibody,

(34) The antibody according to (33), which is represented by ArW30C3A1Aa producible from a hybridoma represented by ArW30C3A1A (FERM BP-8367),

(35) An antibody specifically reacting with a binding site of the antibody according to (34) to a polypeptide comprising the amino acid sequence represented by SEQ ID NO: 5, SEQ ID NO: 7, SEQ ID NO: 9 or SEQ ID NO: 11,

(36) The antibody according to (35), which has a neutralizing activity for a polypeptide comprising the amino acid sequence represented by SEQ ID NO: 5, SEQ ID NO: 7, SEQ ID NO: 9 or SEQ ID NO: 11,

(37) The antibody according to (33), which is represented by ArW30C7F2E8a producible from a hybridoma represented by ArW30C7F2E8 (FERM BP-8368),

(38) An antibody specifically reacting with a binding site of the antibody according to (37) to a polypeptide comprising the amino acid sequence represented by SEQ ID NO: 5, SEQ ID NO: 7, SEQ ID NO: 9 or SEQ ID NO: 11,

(39) The antibody according to (38), which has a neutralizing activity for a polypeptide comprising the amino acid sequence represented by SEQ ID NO: 5, SEQ ID NO: 7, SEQ ID NO: 9 or SEQ ID NO: 11,

(40) A pharmaceutical comprising the antibody according to (1), (14) or (27),

(41) The pharmaceutical according to (40), which is an agent for preventing/treating sterility, renal dropsy, peptic ulcer or hyperchlorhydria,

(42) A diagnostic agent comprising the antibody according to (1), (14) and/or (27),

(43) A method of quantifying a polypeptide comprising the amino acid sequence represented by SEQ ID NO: 4, SEQ ID NO: 5, SEQ ID NO: 6, SEQ ID NO: 7, SEQ ID NO: 8, SEQ ID NO: 9, SEQ ID NO: 10 or SEQ ID NO: 11, or a salt thereof, which comprises using the antibody according to (1),

(44) The quantifying method according to (43), which comprises further using the antibody according to (14) or (27),

(45) A method of quantifying a polypeptide comprising the amino acid sequence represented by SEQ ID NO: 4, SEQ ID NO: 6, SEQ ID NO: 8 or SEQ ID NO: 10, or a salt thereof, which comprises using the antibody according to (14),

(46) A method of quantifying a polypeptide comprising the amino acid sequence represented by SEQ ID NO: 5, SEQ ID NO: 7, SEQ ID NO: 9 or SEQ ID NO: 11, or a salt thereof, which comprises using the antibody according to (27),

(47) A method of quantifying a polypeptide comprising the amino acid sequence represented by SEQ ID NO: 4, SEQ ID NO: 5, SEQ ID NO: 6, SEQ ID NO: 7, SEQ ID NO: 8, SEQ ID NO: 9, SEQ ID NO: 10 or SEQ ID NO: 11, or a salt thereof, in a test fluid, which comprises competitively reacting the antibody according to (1) with a test fluid and a labeled form of a polypeptide comprising the amino acid sequence represented by SEQ ID NO: 4, SEQ ID NO: 5, SEQ ID NO: 6, SEQ ID NO: 7, SEQ ID NO: 8, SEQ ID NO: 9, SEQ ID NO: 10 or SEQ ID NO: 11, or a salt thereof, and determining a ratio of the labeled polypeptide or a salt thereof bound to the antibody,

(48) A method of quantifying a polypeptide comprising the amino acid sequence represented by SEQ ID NO: 4, SEQ ID NO: 6, SEQ ID NO: 8 or SEQ ID NO: 10, or a salt thereof, in a test fluid, which comprises competitively reacting the antibody according to (14) with a test fluid and a labeled form of a polypeptide comprising the amino acid sequence represented by SEQ ID NO: 4, SEQ ID NO: 6, SEQ ID NO: 8 or SEQ ID NO: 10, or a salt thereof, and determining a ratio of the labeled polypeptide or a salt thereof bound to the antibody,

(49) A method of quantifying a polypeptide comprising the amino acid sequence represented by SEQ ID NO: 5, SEQ ID NO: 7, SEQ ID NO: 9 or SEQ ID NO: 11, or a salt thereof, in a test fluid, which comprises competitively reacting the antibody according to (27) with a test fluid and a labeled form of a polypeptide comprising the amino acid sequence represented by SEQ ID NO: 5, SEQ ID NO: 7, SEQ ID NO: 9 or SEQ ID NO: 11, or a salt thereof, and determining a ratio of the labeled polypeptide or a salt thereof bound to the antibody,

(50) A method of quantifying a polypeptide comprising the amino acid sequence represented by SEQ ID NO: 4, SEQ ID NO: 6, SEQ ID NO: 8 or SEQ ID NO: 10, or a salt thereof, in a test fluid, which comprises 1) reacting the antibody according to (1) immobilized on a carrier, a labeled form of the antibody according to (14) and a test fluid, followed by measuring the activity of the label, or 2) reacting the antibody according to (14) immobilized on a carrier, a labeled form of the antibody according to (1) and a test fluid, followed by measuring the activity of the label,

(51) A method of quantifying a polypeptide comprising the amino acid sequence represented by SEQ ID NO: 5, SEQ ID NO: 7, SEQ ID NO: 9 or SEQ ID NO: 11, or a salt thereof, in a test fluid, which comprises 1) reacting the antibody according to (1) immobilized on a carrier, a labeled form of the antibody according to (27) and a test fluid, followed by measuring the activity of the label, or 2) reacting the antibody according to (27) immobilized on a carrier with a labeled form of the antibody according to (1) and a test fluid, followed by measuring the activity of the label,

(52) A method for diagnosis of a disease associated with a polypeptide comprising the amino acid sequence represented by SEQ ID NO: 4, SEQ ID NO: 5, SEQ ID NO: 6, SEQ ID NO: 7, SEQ ID NO: 8, SEQ ID NO: 9, SEQ ID NO: 10 or SEQ ID NO: 11, or a salt thereof, which comprises using the antibody according to (1),

(53) The method for diagnosis according to (52), which comprises further using the antibody according to (14) or (27),

(54) A method for diagnosis of a disease associated with a polypeptide comprising the amino acid sequence represented by SEQ ID NO: 4, SEQ ID NO: 6, SEQ ID NO: 8 or SEQ ID NO: 10, or a salt thereof, which comprises using the antibody according to (14),

(55) A method for diagnosis of a disease associated with a polypeptide comprising the amino acid sequence represented by SEQ ID NO: 5, SEQ ID NO: 7, SEQ ID NO: 9 or SEQ ID NO: 11, or a salt thereof, which comprises using the antibody according to (27),

(56) The method for diagnosis according to (52) through (55), wherein the diseases is sterility, renal dropsy, peptic ulcer or hyperchlorhydria,

(57) A hybridoma producing the antibody according to (7),

(58) The hybridoma according to (57), which is represented by AhW23N2G6D1 (FERM BP-8363) or AhW23N3H3E4 (FERM BP-8364),

(59) A method of producing the antibody according to (7), which comprises culturing the hybridoma according to (58) in vivo or in vitro and collecting the antibody according to (7) from the body fluid or culture,

(60) A hybridoma producing the antibody according to (20),

(61) The hybridoma according to (60), which is represented by AhW23C6G1H8 (FERM BP-8365) or AhW23C5G2F6 (FERM BP-8366),

(62) A method of producing the antibody according to (20), which comprises culturing the hybridoma according to (61) in vivo or in vitro and collecting the antibody according to (20) from the body fluid or culture,

(63) A hybridoma producing the antibody according to (33),

(64) The hybridoma according to (63), which is represented by ArW30C3A1A (FERM BP-8367) or ArW30C7F2E8 (FERM BP-8368),

(65) A method of producing the antibody according to (33), which comprises culturing the hybridoma according to (64) in vivo or in vitro and collecting the monoclonal antibody according to (33) from the body fluid or culture,

(66) A method of preventing/treating sterility, renal dropsy, peptic ulcer or hyperchlorhydria, which comprises administering to a mammal an effective dose of the antibody according to (1), (14) or (27),

(67) Use of the antibody according to (1), (14) or (27) to manufacture an agent for preventing/treating sterility, renal dropsy, peptic ulcer or hyperchlorhydria.

BEST MODE FOR CARRYING OUT THE INVENTION

Figure 1:
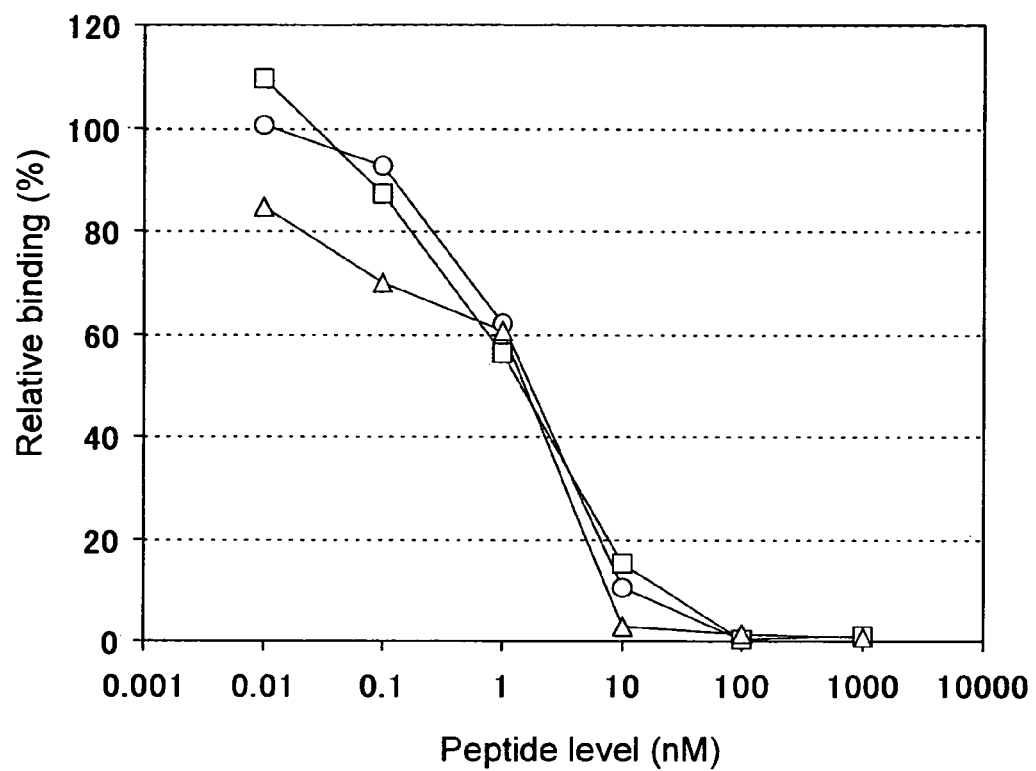
FIG. 1 shows binding inhibition by peptide-1, human NPW23 or human NPW30 against the binding of monoclonal antibody 2G6-D1 to biotin-labeled peptide-1. In the figure, -o- (-open circle-) represents the case where peptide-1 is added, -□- (-open square-) represents the case where human NPW23 is added, and -Δ- (-open triangle-) represents the case where human NPW30 is added, respectively.
Figure 2:
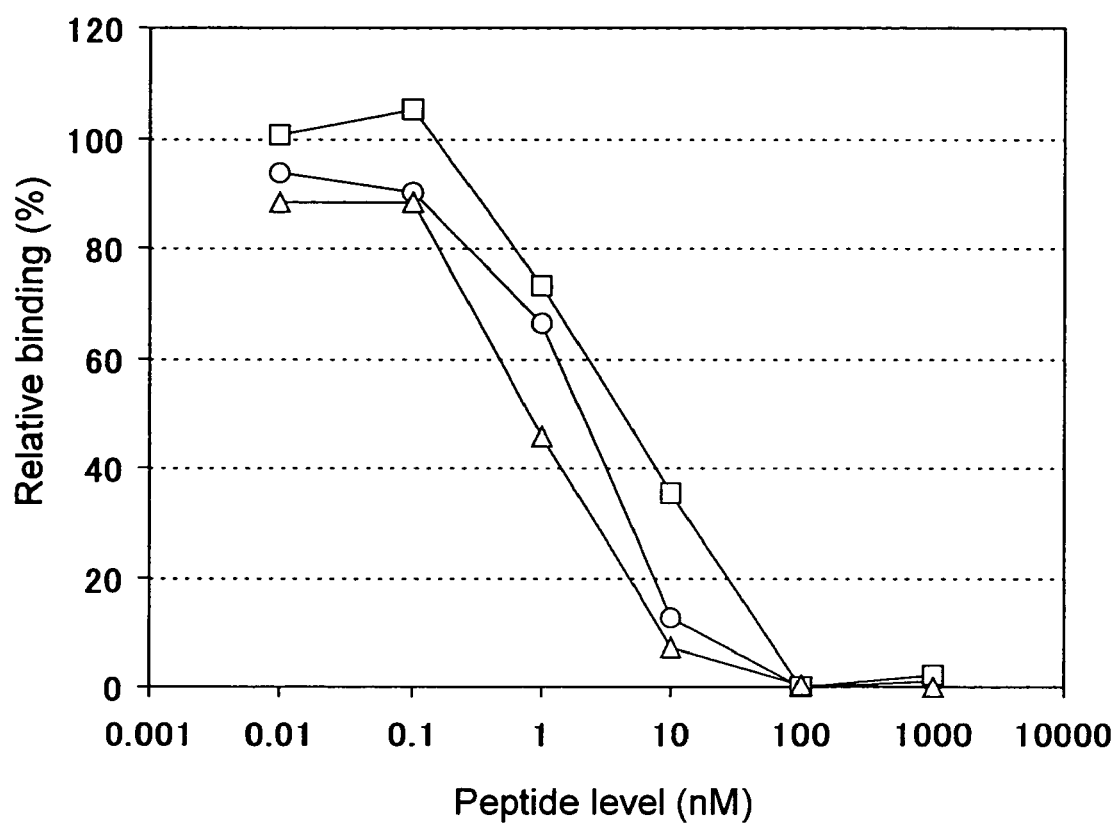
FIG. 2 shows binding inhibition by peptide-1, human NPW23 or human NPW30 against the binding of monoclonal antibody 3H3-E4 to biotin-labeled peptide-1. In the figure, -o- (-open circle-) represents the case where peptide-1 is added, -□- (-open square-) represents the case where human NPW23 is added, and -Δ- (-open triangle-) represents the case where human NPW30 is added, respectively.
Figure 3:
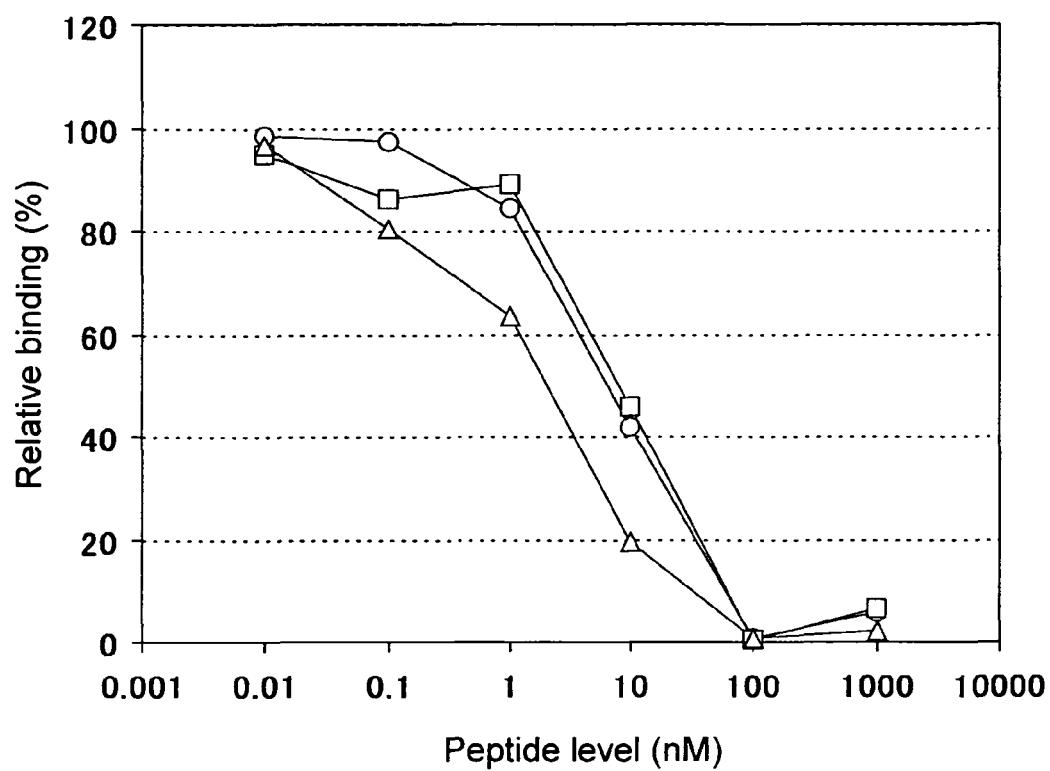
FIG. 3 shows binding inhibition by peptide-1, human NPW23 or human NPW30 against the binding of monoclonal antibody 5E6-C3 to biotin-labeled peptide-1. In the figure, -o- (-open circle-) represents the case where peptide-1 is added, -□- (-open square-) represents the case where human NPW23 is added, and -Δ- (-open triangle-) represents the case where human NPW30 is added, respectively.
Figure 4:
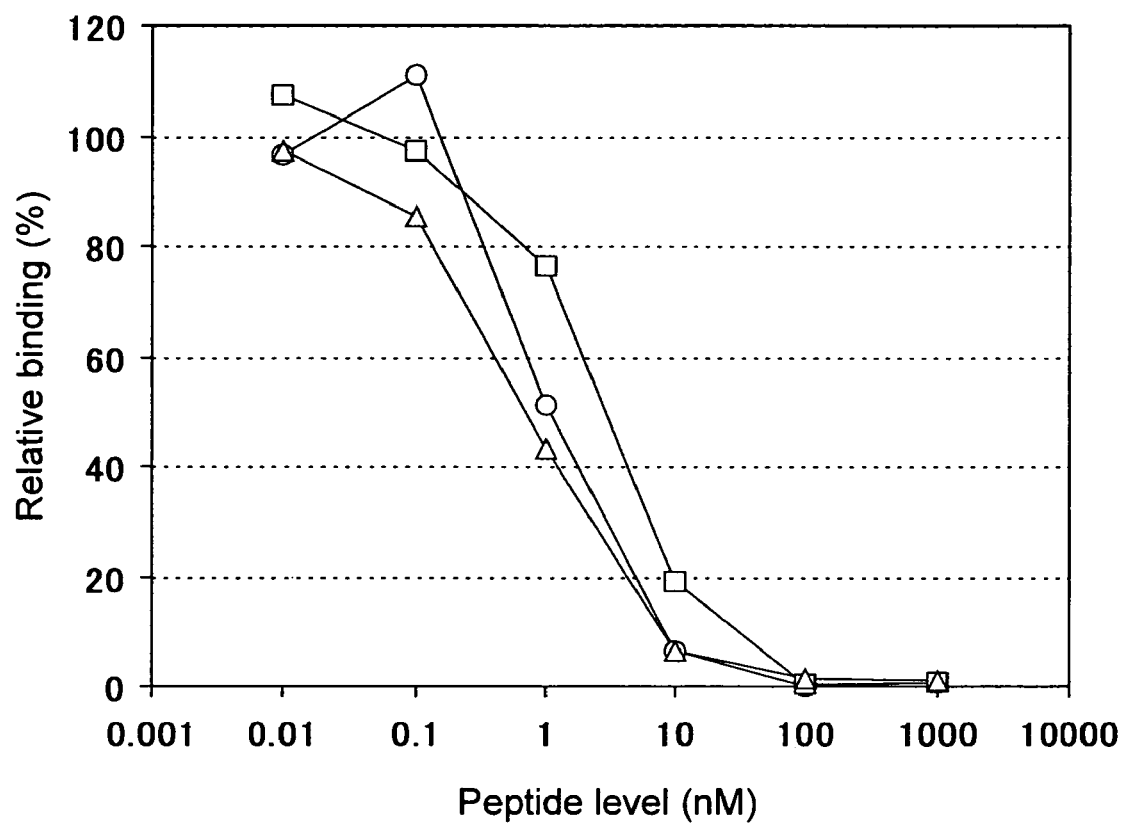
FIG. 4 shows binding inhibition by peptide-1, human NPW23 or human NPW30 against the binding of monoclonal antibody 7F9-E12 to biotin-labeled peptide-1. In the figure, -o- (-open circle-) represents the case where peptide-1 is added, -□- (-open square-) represents the case where human NPW23 is added, and -Δ- (-open triangle-) represents the case where human NPW30 is added, respectively.
Figure 5:
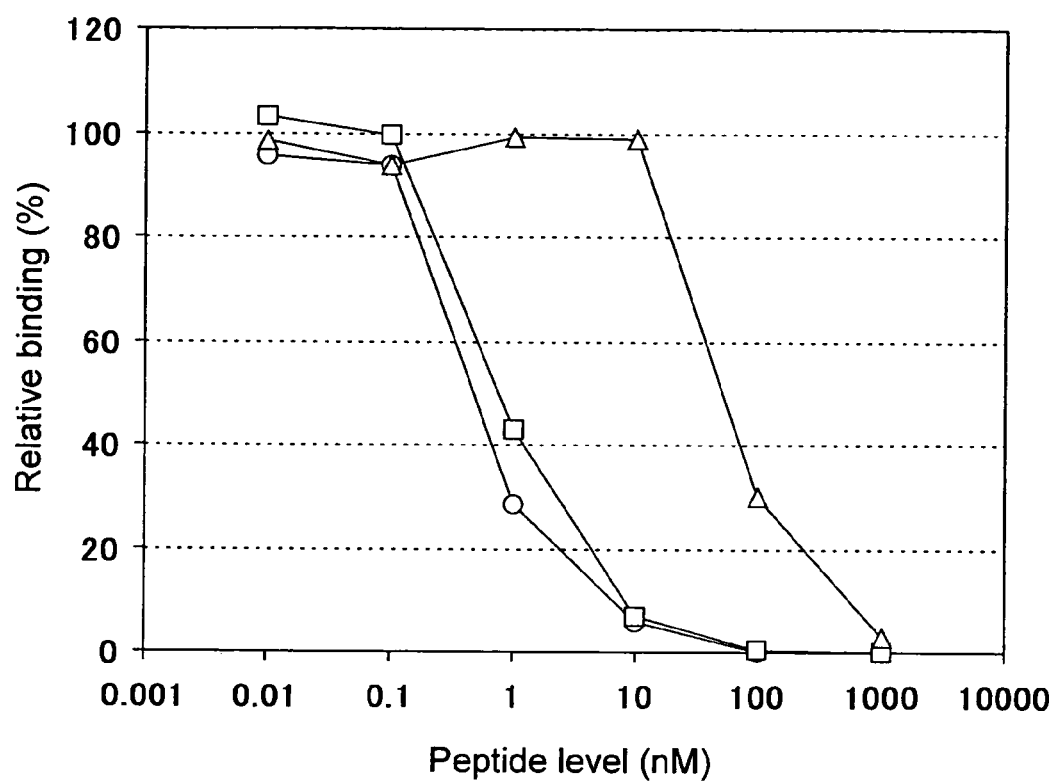
FIG. 5 shows binding inhibition by peptide-2, human NPW23 or human NPW30 against the binding of monoclonal antibody 2F1B2A to biotin-labeled peptide-2. In the figure, -○- (-open circle-) represents the case where peptide-2 is added, -□- (-open square-) represents the case where human NPW23 is added, and -Δ- (-open triangle-) represents the case where human NPW30 is added, respectively.
Figure 6:
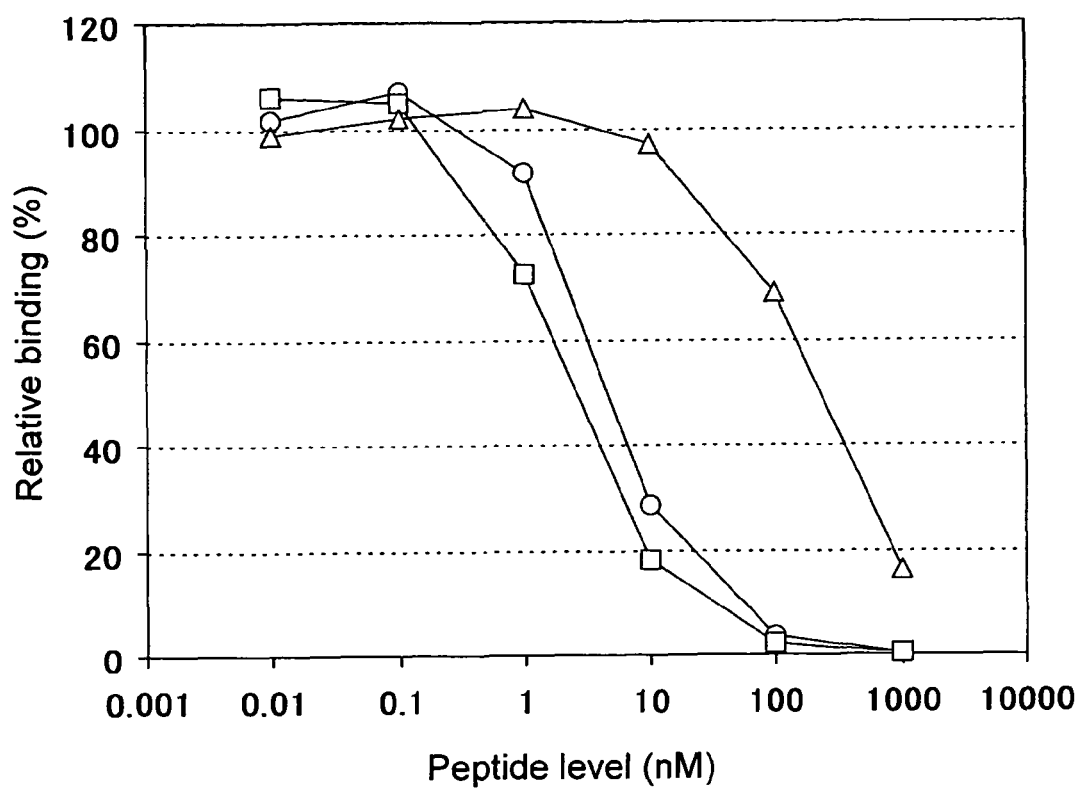
FIG. 6 shows binding inhibition by peptide-2, human NPW23 or human NPW30 against the binding of monoclonal antibody 5A2A to biotin-labeled peptide-2. In the figure, -○- (-open circle-) represents the case where peptide-2 is added, -□- (-open square-) represents the case where human NPW23 is added, and -Δ- (-open triangle-) represents the case where human NPW30 is added, respectively.
Figure 7:
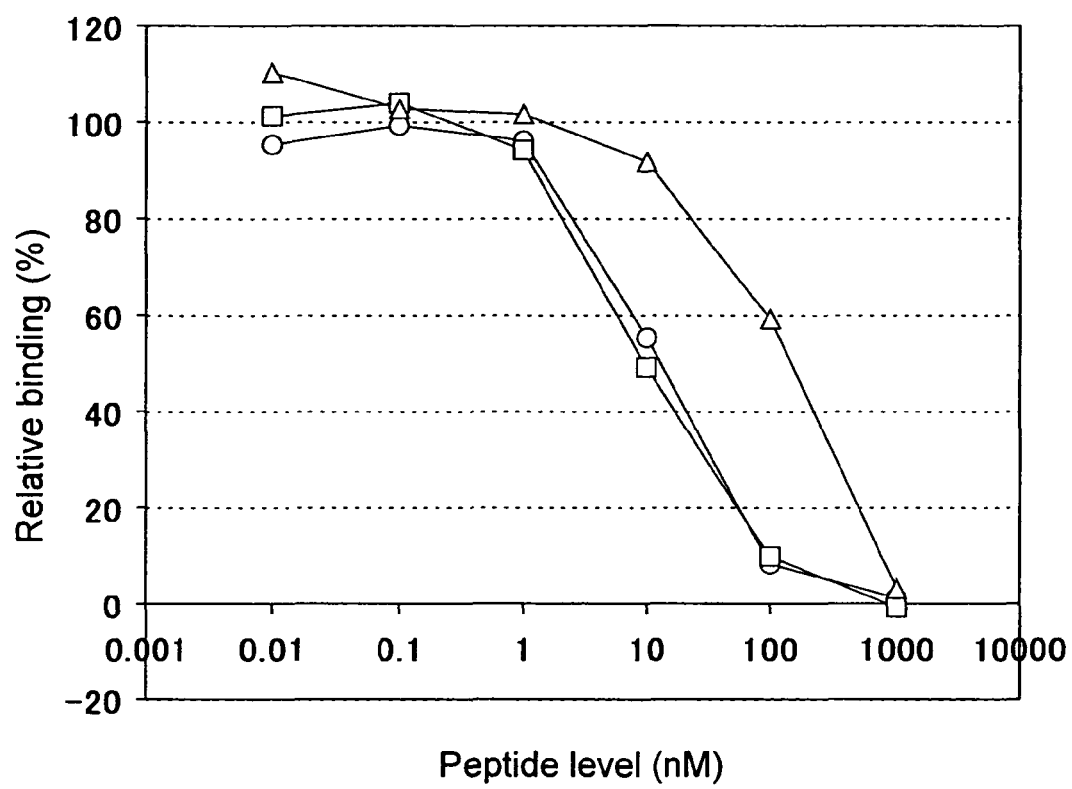
FIG. 7 shows binding inhibition by peptide-2, human NPW23 or human NPW30 against the binding of monoclonal antibody 5D6-F10 to biotin-labeled peptide-2. In the figure, -○- (-open circle-) represents the case where peptide-2 is added, -○- (-open square-) represents the case where human NPW23 is added, and -Δ- (-open triangle-) represents the case where human NPW30 is added, respectively.
Figure 8:
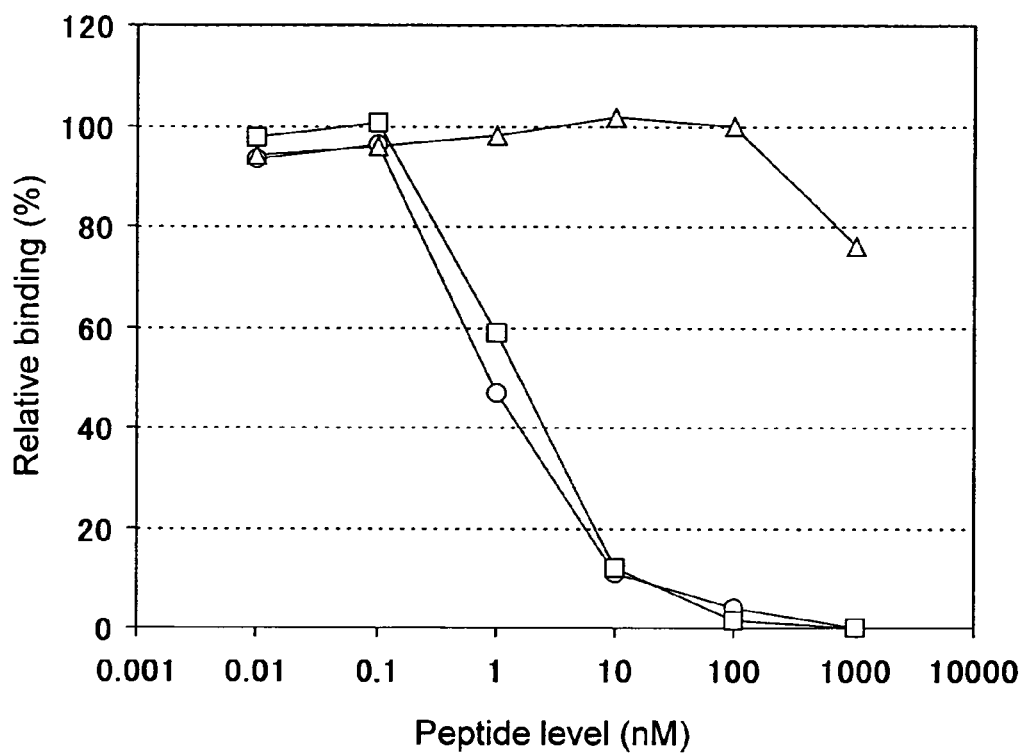
FIG. 8 shows binding inhibition by peptide-2, human NPW23 or human NPW30 against the binding of monoclonal antibody 5G2-F6 to biotin-labeled peptide-2. In the figure, -○- (-open circle-) represents the case where peptide-2 is added, -□- (-open square-) represents the case where human NPW23 is added, and -Δ- (-open triangle-) represents the case where human NPW30 is added, respectively.
Figure 9:
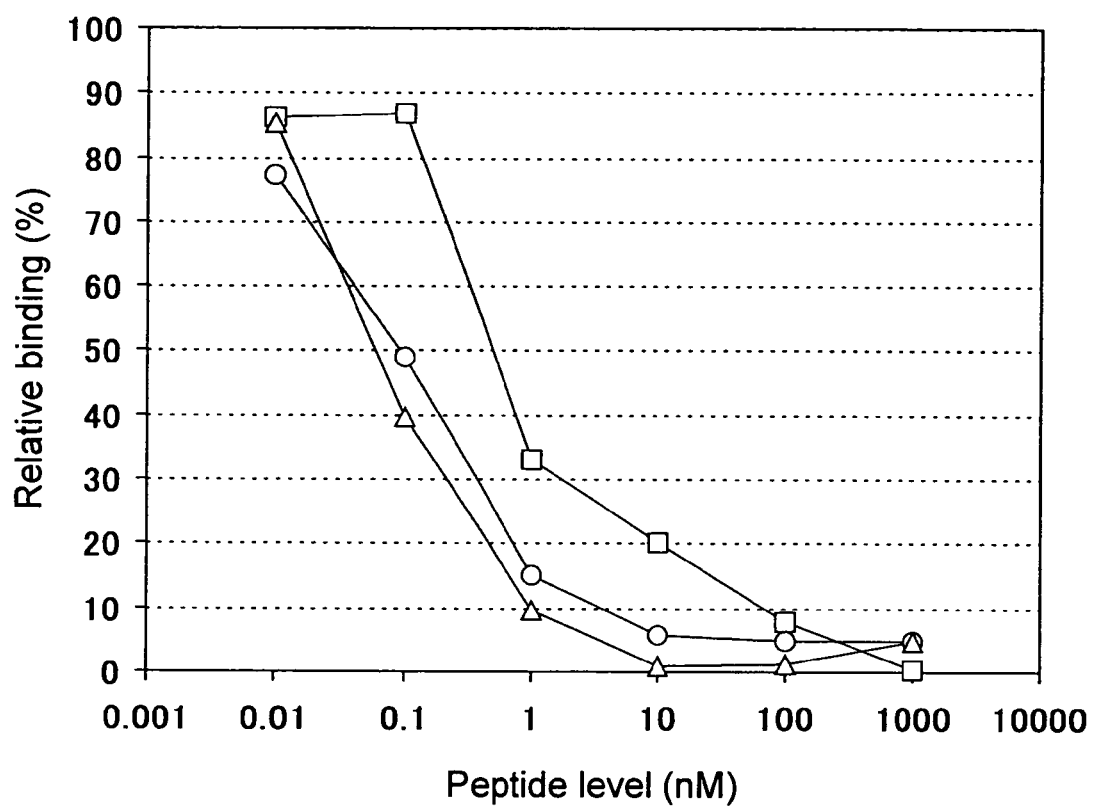
FIG. 9 shows binding inhibition by peptide-2, human NPW23 or human NPW30 against the binding of monoclonal antibody 6G1-H8 to biotin-labeled peptide-2. In the figure, -○- (-open circle-) represents the case where peptide-2 is added, -○- (-open square-) represents the case where human NPW23 is added, and -Δ- (-open triangle-) represents the case where human NPW30 is added, respectively.
Figure 10:
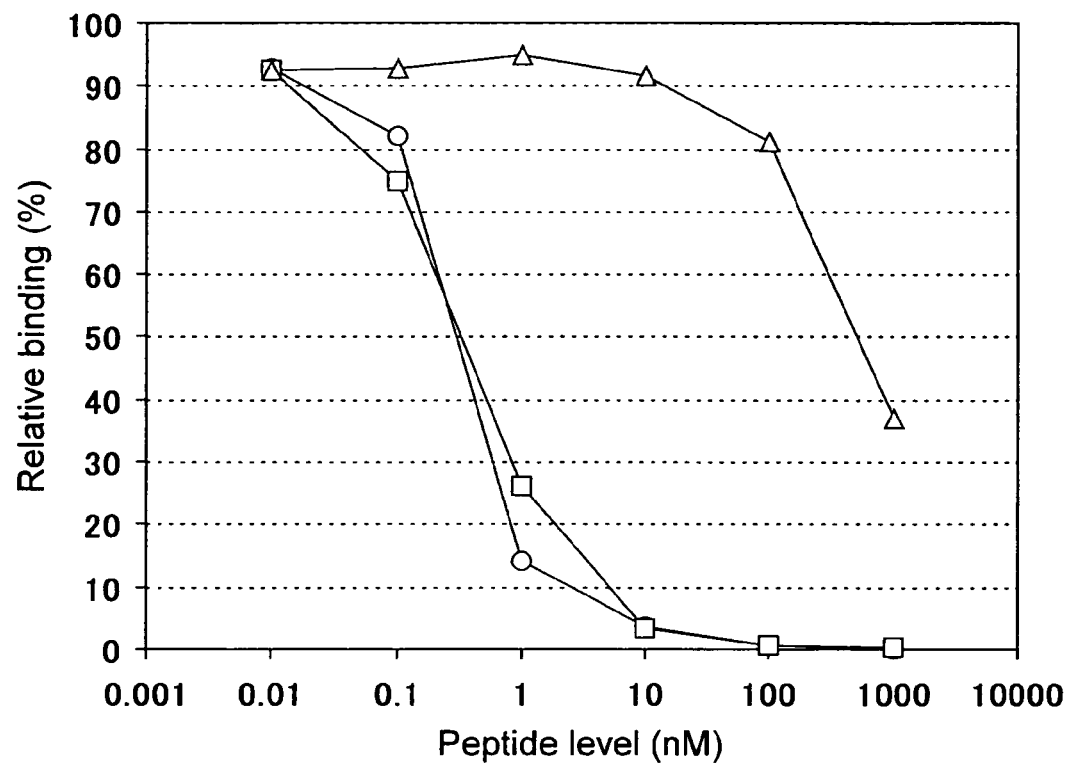
FIG. 10 shows binding inhibition by peptide-2, human NPW23 or human NPW30 against the binding of monoclonal antibody 7B4-D2 to biotin-labeled peptide-2. In the figure, -○- (-open circle-) represents the case where peptide-2 is added, -□- (-open square-) represents the case where human NPW23 is added, and -Δ- (-open triangle-) represents the case where human NPW30 is added, respectively.

Throughout the specification, the proteins (polypeptides) are represented in accordance with the conventional way of describing peptides, that is, the N-terminus (amino terminus) at the left hand and the C-terminus (carboxyl terminus) at the right hand. In the proteins used in the present invention including a polypeptide comprising the amino acid sequence represented by SEQ ID NO: 1, the C-terminus may be in any form of a carboxyl group, a carboxylate, an amide and an ester.

As the polypeptide comprising the amino acid sequence represented by SEQ ID NO: 4, SEQ ID NO: 5, SEQ ID NO: 6, SEQ ID NO: 7, SEQ ID NO: 8, SEQ ID NO: 9, SEQ ID NO: 10 or SEQ ID NO: 11, there is used a polypeptide comprising, for example, (1) the amino acid sequence represented by SEQ ID NO: 4, SEQ ID NO: 5, SEQ ID NO: 6, SEQ ID NO: 7, SEQ ID NO: 8, SEQ ID NO: 9, SEQ ID NO: 10 or SEQ ID NO: 11, wherein several (1 to 5) amino acids are added to the amino acid sequence described above; (2) the amino acid sequence represented by SEQ ID NO: 4, SEQ ID NO: 5, SEQ ID NO: 6, SEQ ID NO: 7, SEQ ID NO: 8, SEQ ID NO: 9, SEQ ID NO: 10 or SEQ ID NO: 11, wherein several (1 to 5) amino acids are inserted into the amino acid sequence described above, (3) the amino acid sequence represented by SEQ ID NO: 4, SEQ ID NO: 5, SEQ ID NO: 6, SEQ ID NO: 7, SEQ ID NO: 8, SEQ ID NO: 9, SEQ ID NO: 10 or SEQ ID NO: 11, wherein several (1 to 5) amino acids in the amino acid sequence described above are replaced with other amino acids, and the like.

As salts of the polypeptide comprising the amino acid sequence represented by SEQ ID NO: 4, SEQ ID NO: 5, SEQ ID NO: 6, SEQ ID NO: 7, SEQ ID NO: 8, SEQ ID NO: 9, SEQ ID NO: 10 or SEQ ID NO: 11, salts with physiologically acceptable acids (e.g., inorganic acids, organic acids) or bases (e.g., alkali metals, etc.) are used, particularly preferred are physiologically acceptable acid addition salts. Examples of such salts are salts with, for example, inorganic acids (e.g., hydrochloric acid, phosphoric acid, hydrobromic acid or sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid or benzenesulfonic acid), and the like.

Examples of the partial peptides at the N-terminal region of the polypeptide comprising the amino acid sequence represented by SEQ ID NO: 4, SEQ ID NO: 5, SEQ ID NO: 6, SEQ ID NO: 7, SEQ ID NO: 8, SEQ ID NO: 9, SEQ ID NO: 10 or SEQ ID NO: 11, or salts of the polypeptide include:

(a) in the amino acid sequence represented by SEQ ID NO: 4, SEQ ID NO: 5, SEQ ID NO: 6, SEQ ID NO: 7, SEQ ID NO: 8, SEQ ID NO: 9, SEQ ID NO: 10 or SEQ ID NO: 11:

(i) a polypeptide having the 1st-3rd amino acid sequence,
(ii) a polypeptide having the 1st-4th amino acid sequence,
(iii) a polypeptide having the 1st-5th amino acid sequence,
(iv) a polypeptide having the 1st-6th amino acid sequence,
(v) a polypeptide having the 1st-7th amino acid sequence,
(vi) a polypeptide having the 1st-8th amino acid sequence,
(vii) a polypeptide having the 1st-9th amino acid sequence,
(viii) a polypeptide having the 2nd-4th amino acid sequence,
(ix) a polypeptide having the 2nd-5th amino acid sequence,
(x) a polypeptide having the 2nd-6th amino acid sequence,
(xi) a polypeptide having the 2nd-7th amino acid sequence,
(xii) a polypeptide having the 2nd-8th amino acid sequence,
(xiii) a polypeptide having the 2nd-9th amino acid sequence,
(xiv) a polypeptide having the 3rd-5th amino acid sequence,
(xv) a polypeptide having the 3rd-6th amino acid sequence,
(xvi) a polypeptide having the 3rd-7th amino acid sequence,
(xvii) a polypeptide having the 3rd-8th amino acid sequence,
(xviii) a polypeptide having the 3rd-9th amino acid sequence,
(xix) a polypeptide having the 4th-6th amino acid sequence,
(xx) a polypeptide having the 4th-7th amino acid sequence,
(xxi) a polypeptide having the 4th-8th amino acid sequence,
(xxii) a polypeptide having the 4th-9th amino acid sequence,
(xxiii) a polypeptide having the 5th-7th amino acid sequence,
(xxiv) a polypeptide having the 5th-8th amino acid sequence,
(xxv) a polypeptide having the 5th-9th amino acid sequence,
(xxvi) a polypeptide having the 6th-8th amino acid sequence,
(xxvii) a polypeptide having the 6th-9th amino acid sequence and
(xxviii) a polypeptide having the 7th-9th amino acid sequence;

(b) a polypeptide having the 1st-5th amino acid sequence in the amino acid sequence represented by SEQ ID NO: 10 or SEQ ID NO: 11, and so on.

Examples of the partial peptides at the C-terminal region of the polypeptide comprising the amino acid sequence represented by SEQ ID NO: 4, SEQ ID NO: 6, SEQ ID NO: 8 or SEQ ID NO: 10, or salts of the polypeptide include, in the amino acid sequence represented by SEQ ID NO: 4, SEQ ID NO: 6, SEQ ID NO: 8 or SEQ ID NO: 10:

(i) a polypeptide having the 16th-23rd amino acid sequence,
(ii) a polypeptide having the 17th-23rd amino acid sequence,
(iii) a polypeptide having the 18th-23rd amino acid sequence,
(iv) a polypeptide having the 19th-23rd amino acid sequence, (v) a polypeptide having the 20th-23rd amino acid sequence,
(vi) a polypeptide having the 21st-23rd amino acid sequence,
(vii) a polypeptide having the 16th-22nd amino acid sequence,
(viii) a polypeptide having the 17th-22nd amino acid sequence,
(ix) a polypeptide having the 18th-22nd amino acid sequence,
(x) a polypeptide having the 19th-22nd amino acid sequence,
(xi) a polypeptide having the 20th-22nd amino acid sequence,
(xii) a polypeptide having the 16th-21st amino acid sequence,
(xiii) a polypeptide having the 17th-21st amino acid sequence,
(xiv) a polypeptide having the 18th-21st amino acid sequence,
(xv) a polypeptide having the 19th-21st amino acid sequence,
(xvi) a polypeptide having the 16th-20th amino acid sequence,
(xvii) a polypeptide having the 17th-20th amino acid sequence and
(xviii) a polypeptide having the 18th-20th amino acid sequence, etc.

Examples of the partial peptides at the C-terminal region of the polypeptide comprising the amino acid sequence represented by SEQ ID NO: 5, SEQ ID NO: 7, SEQ ID NO: 9 or SEQ ID NO: 11, or salts of the polypeptide include, in the amino acid sequence represented by SEQ ID NO: 5, SEQ ID NO: 7, SEQ ID NO: 9 or SEQ ID NO: 11:
(i) a polypeptide having the 23rd-30th amino acid sequence,
(ii) a polypeptide having the 24th-30th amino acid sequence,
(iii) a polypeptide having the 25th-30th amino acid sequence,
(iv) a polypeptide having the 26th-30th amino acid sequence,
(v) a polypeptide having the 27th-30th amino acid sequence,
(vi) a polypeptide having the 28th-30th amino acid sequence,
(vii) a polypeptide having the 23rd-29th amino acid sequence,
(viii) a polypeptide having the 24th-29th amino acid sequence,
(ix) a polypeptide having the 25th-29th amino acid sequence,
(x) a polypeptide having the 26th-29th amino acid sequence,
(xi) a polypeptide having the 27th-29th amino acid sequence,
(xii) a polypeptide having the 23rd-28th amino acid sequence,
(xiii) a polypeptide having the 24th-28th amino acid sequence,
(xiv) a polypeptide having the 25th-28th amino acid sequence,
(xv) a polypeptide having the 26th-28th amino acid sequence,
(xvi) a polypeptide having the 23rd-27th amino acid sequence,
(xvii) a polypeptide having the 24th-27th amino acid sequence,
(xviii) a polypeptide having the 25th-27th amino acid sequence, and so on.

The antibodies, which specifically react with partial peptides at the N-terminal region of the polypeptide comprising the amino acid sequence represented by SEQ ID NO: 4, SEQ ID NO: 5, SEQ ID NO: 6, SEQ ID NO: 7, SEQ ID NO: 8, SEQ ID NO: 9, SEQ ID NO: 10 or SEQ ID NO: 11, or salts of the polypeptide, may be those specifically reacting with partial peptides at the N-terminal region of the polypeptide or salts thereof, and preferably are monoclonal antibodies. Specifically, there are used antibodies (preferably, monoclonal antibodies), which specifically react with a peptide comprising the 1st-13th amino acid sequence in the amino acid sequence represented by SEQ ID NO: 4, a polypeptide having the 1st-13th amino acid sequence in the amino acid sequence represented by SEQ ID NO: 4 wherein the 14th amino acid is substituted with Cys-NH$_2$; and the like.

In these antibodies, preferably used are antibodies, which do not recognize partial peptides at the C-terminal region of the polypeptide comprising the amino acid sequence represented by SEQ ID NO: 4, SEQ ID NO: 5, SEQ ID NO: 6, SEQ ID NO: 7, SEQ ID NO: 8, SEQ ID NO: 9, SEQ ID NO: 10 or SEQ ID NO: 11, or salts of the polypeptide.

More preferred are antibodies neutralizing the activity of the polypeptide comprising the amino acid sequence represented by SEQ ID NO: 4, SEQ ID NO: 5, SEQ ID NO: 6, SEQ ID NO: 7, SEQ ID NO: 8, SEQ ID NO: 9, SEQ ID NO: 10 or SEQ ID NO: 11, or salts of the polypeptide.

Specific examples include antibodies suppressing the activity at least 10%, preferably at least 50%, more preferably at least 80% of the polypeptide or salts thereof described above [e.g., cell stimulating activities on the human GPR8, human GPR7, rat GPR7 or mouse GPR7-expressed cells (e.g., activities that promote arachidonic acid release, acetylcholine release, intracellular Ca$^{2+}$ release, intracellular cAMP production and suppression, intracellular cGMP production, inositol phosphate production, change in cell membrane potential, phosphorylation of intracellular proteins, activation of c-fos, pH reduction, GTP$\gamma$S binding activities, etc.) and the like], when the antibodies are added to the polypeptide comprising the amino acid sequence represented by SEQ ID NO: 4, SEQ ID NO: 5, SEQ ID NO: 6, SEQ ID NO: 7, SEQ ID NO: 8, SEQ ID NO: 9, SEQ ID NO: 10 or SEQ ID NO: 11, or salts of the polypeptide, in a molar ratio of 1 to 1000-fold, preferably 1 to 100-fold and more preferably 1 to 10-fold.

Specific examples of the antibodies which are preferably used are the monoclonal antibody represented by AhW23N2G6D1a, the monoclonal antibody represented by AhW23N3H3E4a, etc.

As the antibodies, which specifically react with partial peptides at the N-terminal region of the polypeptide comprising the amino acid sequence represented by SEQ ID NO: 4, SEQ ID NO: 5, SEQ ID NO: 6, SEQ ID NO: 7, SEQ ID NO: 8, SEQ ID NO: 9, SEQ ID NO: 10 or SEQ ID NO: 11, or salts of the polypeptide, there are further employed antibodies, which specifically recognize (a), in the amino acid sequence represented by SEQ ID NO: 4, SEQ ID NO: 5, SEQ ID NO: 6, SEQ ID NO: 7, SEQ ID NO: 8, SEQ ID NO: 9, SEQ ID NO: 10 or SEQ ID NO: 11, (i) the 1st-3rd amino acid sequence, (ii) the 1st-4th amino acid sequence, (iii) the 1st-5th amino acid sequence, (iv) the 1st-6th amino acid sequence, (v) the 1st-7th amino acid sequence, (vi) the 1st-8th amino acid sequence, (vii) the 1st-9th amino acid sequence, (viii) the 2nd-4th amino acid sequence, (ix) the 2nd-5th amino acid sequence, (x) the 2nd-6th amino acid sequence, (xi) the 2nd-7th amino acid sequence, (xii) the 2nd-8th amino acid sequence, (xiii) the 2nd-9th amino acid sequence, (xiv) the 3rd-5th amino acid sequence and (xv) the 3rd-6th amino acid sequence, (xvi) the 3rd-7th amino acid sequence, (xvii) the 3rd-8th amino acid sequence, (xviii) the 3rd-9th amino acid sequence, (xix) the 4th-6th amino acid sequence, (xx) the 4th-7th amino acid sequence, (xxi) the 4th-8th amino acid sequence, (xxii) the 4th-9th amino acid sequence, (xxiii) the 5th-7th amino acid sequence, (xxiv) the 5th-8th amino acid sequence, (xxv) the 5th-9th amino acid sequence, (xxvi) the 6th-8th amino acid sequence, (xxvii) the 6th-9th amino acid sequence or (xxviii) the 7th-9th amino acid sequence, or (b) the 1st-5th amino acid sequence in the amino acid sequence represented by SEQ ID NO: 10 or SEQ ID NO: 11; and the like.

The present invention also includes antibodies (e.g., monoclonal antibodies), which specifically react with a binding site of the monoclonal antibody represented by AhW23N2G6D1a or the monoclonal antibody represented by AhW23N3H3E4a, to the polypeptide comprising the amino acid sequence represented by SEQ ID NO: 4, SEQ ID NO: 5, SEQ ID NO: 6, SEQ ID NO: 7, SEQ ID NO: 8, SEQ ID NO: 9, SEQ ID NO: 10 or SEQ ID NO: 11. Above all, they are antibodies (e.g., monoclonal antibodies) having a neutralizing activity for the polypeptide described above.

The "binding site" described above may be any of the sites to which the monoclonal antibody represented by AhW23N2G6D1a or the monoclonal antibody represented by AhW23N3H3E4a may bind, preferably, a specific binding site, i.e., an epitope.

The antibodies that specifically react with partial peptides at the C-terminal region of the polypeptide comprising the amino acid sequence represented by SEQ ID NO: 4, SEQ ID NO: 6, SEQ ID NO: 8 or SEQ ID NO: 10, or salts of the polypeptide may be antibodies that are specifically reactive with partial peptides at the C-terminal region of the polypeptide comprising the amino acid sequence represented by SEQ ID NO: 4, SEQ ID NO: 6, SEQ ID NO: 8 or SEQ ID NO: 10, or salts of the polypeptide, and preferably monoclonal antibodies.

Specifically, there are used, for example, antibodies (preferably, monoclonal antibodies), which specifically react with peptides having the 11th-23rd amino acid sequence in the amino acid sequence represented by SEQ ID NO: 4, or with polypeptides having the amino acid sequence represented by SEQ ID NO: 4 and having Cys added to the 11th amino acid of this amino acid sequence, and the like.

In these antibodies, preferably used are antibodies, which do not recognize partial peptides at the N-terminal region of the polypeptide comprising the amino acid sequence represented by SEQ ID NO: 4, SEQ ID NO: 6, SEQ ID NO: 8 or SEQ ID NO: 10, or salts of the polypeptide.

More preferably, the antibodies are those neutralizing the activity of the polypeptide comprising the amino acid sequence represented by SEQ ID NO: 4, SEQ ID NO: 6, SEQ ID NO: 8 or SEQ ID NO: 10, or salts of the polypeptide.

Specific examples include antibodies suppressing the activity at least 10%, preferably at least 50%, more preferably at least 80% of the polypeptide or salts thereof described above [e.g., cell stimulating activities on the human GPR8, human GPR7, rat GPR7 or mouse GPR7-expressed cells (e.g., activities that promote arachidonic acid release, acetylcholine release, intracellular $Ca^{2+}$ release, intracellular cAMP production and suppression, intracellular cGMP production, inositol phosphate production, change in cell membrane potential, phosphorylation of intracellular proteins, activation of c-fos, pH reduction, GTPγS binding activities, etc.) and the like], when the antibodies are added to the polypeptide comprising the amino acid sequence represented by SEQ ID NO: 4, SEQ ID NO: 6, SEQ ID NO: 8 or SEQ ID NO: 10, or salts of the polypeptide, in a molar ratio of 1 to 1000-fold, preferably 1 to 100-fold and more preferably 1 to 10-fold.

Specific examples of the antibodies which are preferably used include the monoclonal antibody represented by AhW23N2G6D1a, the monoclonal antibody represented by AhW23N3H3E4a, and the like.

Further as the antibodies, which specifically react with partial peptides at the C-terminal region of the polypeptide comprising the amino acid sequence represented by SEQ ID NO: 4, SEQ ID NO: 6, SEQ ID NO: 8 or SEQ ID NO: 10, or salts of the polypeptide, there are employed antibodies, which specifically recognize, in the amino acid sequence represented by SEQ ID NO: 4, SEQ ID NO: 6, SEQ ID NO: 8 or SEQ ID NO: 10, (i) the 16th-23rd amino acid sequence, (ii) the 17th-23rd amino acid sequence, (iii) the 18th-23rd amino acid sequence, (iv) the 19th-23rd amino acid sequence, (v) the 20th-23rd amino acid sequence, (vi) the 21st-23rd amino acid sequence, (vii) the 16th-22nd amino acid sequence, (viii) the 17th-22nd amino acid sequence, (ix) the 18th-22nd amino acid sequence, (x) the 19th-22nd amino acid sequence, (xi) the 20th-22nd amino acid sequence, (xii) the 16th-21st amino acid sequence, (xiii) the 17th-21st amino acid sequence and (xiv) the 18th-21st amino acid sequence, (xv) the 19th-21st amino acid sequence, (xvi) the 16th-20th amino acid sequence, (xvii) the 17th-20th amino acid sequence, or (xviii) the 18th-20th amino acid sequence; and the like.

The present invention also includes the antibodies (e.g., monoclonal antibodies), which specifically react with a binding site of the monoclonal antibody represented by AhW23N2G6D1a or the monoclonal antibody represented by AhW23N3H3E4a, to the polypeptide comprising the amino acid sequence represented by SEQ ID NO: 4, SEQ ID NO: 6, SEQ ID NO: 8 or SEQ ID NO: 10. Above all, they are antibodies (e.g., monoclonal antibodies) having a neutralizing activity for the polypeptide.

The "binding site" described above may be any of the sites to which the monoclonal antibody represented by AhW23N2G6D1a or the monoclonal antibody represented by AhW23N3H3E4a, preferably, a specific binding site, i.e., an epitope.

The antibodies that specifically react with partial peptides at the C-terminal region of the polypeptide comprising the amino acid sequence represented by SEQ ID NO: 5, SEQ ID NO: 7, SEQ ID NO: 9 or SEQ ID NO: 11, or salts of the polypeptide may be antibodies, which specifically react with partial peptides at the C-terminal region of the polypeptide comprising the amino acid sequence represented by SEQ ID NO: 5, SEQ ID NO: 7, SEQ ID NO: 9 or SEQ ID NO: 11, or salts of the polypeptide, and preferably monoclonal antibodies.

Specifically, there are used, for examples, antibodies (preferably, monoclonal antibodies), which specifically react with peptides having the 16th-30th amino acid sequence in the amino acid sequence represented by SEQ ID NO: 7, or with polypeptides having the 16th-30th amino acid sequence in this amino acid sequence and having Cys added to the 16th amino acid of this amino acid sequence, and the like.

In these antibodies, preferably used are antibodies, which do not recognize partial peptides at the N-terminal region of the polypeptide comprising the amino acid sequence represented by SEQ ID NO: 5, SEQ ID NO: 7, SEQ. ID NO: 9 or SEQ ID NO: 11, or salts of the polypeptide.

More preferred are antibodies neutralizing the activity of the polypeptide comprising the amino acid sequence represented by SEQ ID NO: 5, SEQ ID NO: 7, SEQ ID NO: 9 or SEQ ID NO: 11, or salts of the polypeptide.

Specific examples include antibodies suppressing the activity at least 10%, preferably at least 50%, more preferably at least 80% of the polypeptide or salts thereof described above [e.g., cell stimulating activities on the human GPR8, human GPR7, rat GPR7 or mouse GPR7-expressed cells (e.g., activities that promote arachidonic acid release, acetylcholine release, intracellular $Ca^{2+}$ release, intracellular cAMP production and suppression, intracellular cGMP production, inositol phosphate production, change in cell membrane potential, phosphorylation of intracellular proteins, activation of c-fos, pH reduction, GTPγS binding activities, etc.) and the like], when the antibodies are added to the polypeptide comprising the amino acid sequence represented by SEQ ID NO: 5, SEQ ID NO: 7, SEQ ID NO: 9 or SEQ ID NO: 11, or salts of the polypeptide, in a molar ratio of 1 to 1000-fold, preferably 1 to 100-fold and more preferably 1 to 10-fold.

Specific examples of the antibodies which are preferred include the monoclonal antibody represented by ArW30C3A1Aa, the monoclonal antibody represented by ArW30C7F2E8, and the like.

Further as the antibodies, which specifically react with partial peptides at the C-terminal region of the polypeptide comprising the amino acid sequence represented by SEQ ID NO: 5, SEQ ID NO: 7, SEQ ID NO: 9 or SEQ ID NO: 11, or salts of the polypeptide, there are employed antibodies specifically recognizing (i) the 23rd-30th amino acid sequence, (ii) the 24th-30th amino acid sequence, (iii) the 25th-30th amino acid sequence, (iv) the 26th-30th amino acid sequence, (v) the 27th-30th amino acid sequence, (vi) the 28th-30th amino acid sequence, (vii) the 23rd-29th amino acid sequence, (viii) the 24th-29th amino acid sequence, (ix) the 25th-29th amino acid sequence, (x) the 26th-29th amino acid sequence, (xi) the 27th-29th amino acid sequence, (xii) the 23rd-28th amino acid sequence, (xiii) the 24th-28th amino acid sequence and (xiv) the 25th-28th amino acid sequence, (xv) the 26th-28th amino acid sequence, (xvi) the 23rd-27th amino acid sequence, (xvii) the 24th-27th amino acid sequence, or (xviii) the 25th-27th amino acid sequence, in the amino acid sequence represented by SEQ ID NO: 5, SEQ ID NO: 7, SEQ ID NO: 9 or SEQ ID NO: 11; and the like.

The present invention also includes antibodies (e.g., monoclonal antibodies), which specifically react with a binding site of the monoclonal antibody represented by ArW30C3A1Aa or the monoclonal antibody represented by ArW30C7F2E8, to the polypeptide comprising the amino acid sequence represented by SEQ ID NO: 5, SEQ ID NO: 7, SEQ ID NO: 9 or SEQ ID NO: 11. Above all, they are antibodies (e.g., monoclonal antibodies) having a neutralizing activity for the polypeptide.

The "binding site" described above may be any of the sites to which the monoclonal antibody represented by the monoclonal antibody represented by ArW30C3A1Aa or the monoclonal antibody represented by ArW30C7F2E8, preferably a specific binding site, i.e., an epitope.

Hereinafter, description is given to the preparation of antigens for antibodies specifically reacting with partial peptides at the N-terminal region of the polypeptide or a salt thereof, wherein the polypeptide comprising the amino acid sequence represented by SEQ ID NO: 4, SEQ ID NO: 5, SEQ ID NO: 6, SEQ ID NO: 7, SEQ ID NO: 8, SEQ ID NO: 9, SEQ ID NO: 10 or SEQ ID NO: 11, antibodies specifically reacting with partial peptides at the C-terminal region of the polypeptide or a salt thereof, wherein the polypeptide comprising the amino acid sequence represented by SEQ ID NO: 4, SEQ ID NO: 6, SEQ ID NO: 8 or SEQ ID NO: 10, and antibodies specifically reacting with partial peptides at the C-terminal region of the polypeptide or a salt thereof, wherein the polypeptide comprising the amino acid sequence represented by SEQ ID NO: 5, SEQ ID NO: 7, SEQ ID NO: 9 or SEQ ID NO: 11 (hereinafter these antibodies are collectively referred to as the antibody of the present invention) and preparation of these antibodies.

(1) Preparation of Antigen

To prepare the antibody of the present invention, any antigen such as synthetic peptides having 1 or 2 more antigenic determinants, which are the same as in the polypeptide or a salt thereof, wherein the polypeptide comprising the amino acid sequence represented by SEQ ID NO: 4, SEQ ID NO: 5, SEQ ID NO: 6, SEQ ID NO: 7, SEQ ID NO: 8, SEQ ID NO: 9, SEQ ID NO: 10 or SEQ ID NO: 11 (hereinafter sometimes referred to as NPW), etc. may be used (hereinafter these antigens are sometimes referred to as the NPW antigen).

The NPW can be (a) prepared from mammalian tissues or cells of human, monkey, rat, mouse, etc., by publicly known methods or with some modifications, (b) chemically synthesized by publicly known peptide synthesis methods using a peptide synthesizer, etc., or (c) produced by culturing a transformant bearing a DNA encoding the NPW.

(a) Where the NPW antigen is prepared from the mammalian tissues or cells, the tissues or cells are homogenized, then extracted with an acid, an alcohol, etc., and the extract is purified and isolated by a combination of salting-out, dialysis, gel filtration, chromatography techniques such as reverse phase chromatography, ion exchange chromatography, affinity chromatography and the like.

(b) Where the NPW antigen is prepared chemically, the synthetic peptides used are, for example, a peptide having the same structure as the NPW antigen purified from natural one as described above, a peptide containing 1 or 2 more amino acid sequences, which are the same amino acid sequences consisting of at least 3, preferably at least 8 amino acids in an optional region of the amino acid sequence represented by SEQ ID NO: 4, etc.

(c) Where the NPW is prepared using the DNA-bearing transformant, the DNA can be produced in accordance with publicly known cloning techniques [e.g., the method described in Molecular Cloning (2nd ed., J. Sambrook et al., Cold Spring Harbor Lab. Press, 1989), etc.]. The cloning techniques include (1) a method in which transformants carrying DNAs encoding the NPW are obtained from cDNA library by hybridization using DNA probes or DNA primers designed based on the amino acid sequence of NPW, or (2) a method in which transformants carrying DNAs encoding the NPW are obtained by PCR using DNA primers designed based on the amino acid sequence of NPW, etc.

The peptides used as the NPW antigen can be prepared (1) by peptide synthesis methods publicly known, or (2) by cleaving the polypeptides having the amino acid sequence represented by SEQ ID NO: 4, SEQ ID NO: 5, SEQ ID NO: 6, SEQ ID NO: 7, SEQ ID NO: 8, SEQ ID NO: 9, SEQ ID NO: 10 or SEQ ID NO: 11 with an appropriate peptidase.

As the methods for peptide synthesis, for example, any of solid phase synthesis and liquid phase syntheses may be used. That is, the partial peptides or amino acids that can construct the peptide are condensed with the remaining part, and where the product contains protecting groups, the protecting groups are removed, to give the desired peptide. Publicly known methods for condensation and removal of the protecting groups include methods described in (i) or (ii) below, etc.

(i) Peptide Synthesis, Interscience Publishers, New York (1966)

(ii) The Peptide, Academic Press, New York (1965)

After the reaction, the peptide may be purified and isolated by a combination of conventional purification methods such as solvent extraction, distillation, column chromatography, liquid chromatography, recrystallization, etc. to give the peptide. When the peptide obtained by the above methods is in a free form, the peptide can be converted into an appropriate salt by a publicly known method; when the peptide is obtained in a salt form, it can be converted into a free form by a publicly known method.

Amides of the peptide may be obtained using commercially available resins for peptide synthesis, which are suitable for formation of the amides. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmehtylphenyl acetamidomethyl resin, polyacrylamide resin, 4-(2',4'-dimethoxyphenylhydroxymethyl)phenoxy resin, 4-(2',4'-dimethoxyphenyl-Fmoc-aminoethyl) phenoxy resin, etc. Using these resins, amino acids in which α-amino groups and functional groups on the side chains are appropriately protected are condensed on the resin in the order of the sequence of the objective peptide according to various condensation methods publicly known in the art. At the end of the reaction, the peptide is cut out from the resin and at the same time, the protecting groups are removed to obtain the objective peptide. Alternatively, the objective peptide may also be obtained by taking out the peptide protected in part with chlorotrityl resin, oxime resin, 4-hydroxybenzoic acid type resin, etc., and deprotecting the protective groups in a conventional manner.

For condensation of the protected amino acids described above, a variety of activation reagents available for the peptide synthesis may be used, and carbodiimides are particularly preferably employed. Examples of such carbodiimides include DCC, N,N'-diisopropylcarbodiimide, N-ethyl-N'-(3-dimethylaminopropyl)-carbodiimide, etc. For activation by these reagents, the protected amino acids in combination with a racemization inhibitor (e.g., HOBt, HOOBt, etc.) are added directly to the resin, or the protected amino acids are previously activated in the form of symmetric acid anhydrides, HOBt esters or HOOBt esters, followed by adding the thus activated protected amino acids to the resin. Solvents used to activate the protected amino acids or condense with the resin may be chosen from solvents that are known to be usable for peptide condensation reactions. For example, there may be employed acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; tertiary amines such as pyridine etc.; ethers such as dioxan, tetrahydrofuran, etc.; nitriles such as acetonitrile, propionitrile, etc.; esters such as methyl acetate, ethyl acetate, etc.; and appropriate mixtures of these solvents. The reaction temperature is appropriately chosen from the range known to be applicable to peptide bond-forming reactions and is usually selected in the range of approximately −20° C. to 50° C. The activated amino acid derivatives are used generally in an excess of 1.5 to 4 times. The condensation is examined using the ninhydrin reaction; when the condensation is insufficient, the condensation can be completed by repeating the condensation reaction without removal of the protecting groups. When the condensation is yet insufficient even after repeating the reaction, the unreacted amino acids may be acetylated using acetic anhydride or acetylimidazole thereby to cancel any adverse effects on subsequent reactions.

Examples of the protecting groups used to protect the amino groups of the starting amino acids include Z, Boc, t-pentyloxycarbonyl, isobornyloxycarbonyl, 4-methoxybenzyloxycarbonyl, Cl—Z, Br—Z, adamantyloxycarbonyl, trifluoroacetyl, phthaloyl, formyl, 2-nitrophenylsulphenyl, diphenylphosphinothioyl, Fmoc, etc. Examples of the protecting groups of a carboxyl group include, in addition to a $C_{1-6}$ alkyl group, a $C_{3-8}$ cycloalkyl group, a $C_{7-14}$ aralkyl group, 2-adamantyl, 4-nitrobenzyl, 4-methoxybenzyl, 4-chlorobenzyl, phenacyl and benzyloxycarbonyl hydrazide, t-butoxycarbonyl hydrazide, trityl hydrazide, and the like.

The hydroxyl group of serine and threonine can be protected through, for example, its esterification or etherification. Examples of the groups suitable for the esterification include a lower ($C_{1-6}$) alkanoyl group, such as acetyl group, etc.; an aroyl group such as benzoyl group, etc., and a group derived from carbonic acid such as benzyloxycarbonyl group, ethoxycarbonyl group, etc. Examples of a group suitable for the etherification include benzyl group, tetrahydropyranyl group, t-butyl group, etc.

Examples of groups for protecting the phenolic hydroxyl group of tyrosine include Bzl, Cl-Bzl, 2-nitrobenzyl, Br—Z, t-butyl, etc.

Examples of groups used to protect the imidazole moiety of histidine include Tos, 4-methoxy-2,3,6-trimethylbenzenesulfonyl, DNP, Bom, Bum, Boc, Trt, Fmoc, etc.

Examples of the activated carboxyl groups in the starting materials include the corresponding acid anhydrides, azides, activated esters [esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)]. Examples of the activated amino groups in the starting materials include the corresponding phosphoric amides.

To eliminate (split off) the protecting groups, there are used catalytic reduction under hydrogen gas flow in the presence of a catalyst such as Pd-black, Pd-carbon, etc.; an acid treatment with anhydrous hydrofluoric acid, methanesulfonic acid, trifluoromethane-sulfonic acid or trifluoroacetic acid, or a mixture solution of these acids; a treatment with a base such as diisopropylethylamine, triethylamine, piperidine, piperazine, etc.; and reduction with sodium in liquid ammonia; or the like. The elimination of the protecting groups by the acid treatment described above is carried out generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol, 1,2-ethanedithiol, etc. Furthermore, 2,4-dinitrophenyl group known as the protecting group for the imidazole of histidine is removed by a treatment with thiophenol. Formyl group used as the protecting group of the indole of tryptophan is eliminated by the aforesaid acid treatment in the presence of 1,2-ethanedithiol, 1,4-butanedithiol, etc. as well as by a treatment with an alkali such as a dilute sodium hydroxide solution, dilute ammonia, etc.

Protection of the functional groups that should not be involved in the reaction of the starting materials, protecting groups, elimination of the protecting groups and activation of the functional groups involved in the reaction may be appropriately chosen from publicly known groups and publicly known means.

In another method for obtaining the amides of the peptide, for example, the α-carboxyl group of the carboxy terminal amino acid is first protected by amidation; the peptide chain is then extended to a desired length toward the amino group side. Thereafter, a peptide in which only the protecting group of the N-terminal α-amino group in the peptide chain has been eliminated from the peptide and a peptide (or amino acids) in which only the protecting group of the C-terminal carboxyl group has been eliminated are prepared. The two peptides are condensed in a mixture of the solvents described above. The details of the condensation reaction are the same as described above. After the protected peptide obtained by the condensation is purified, all the protecting groups are eliminated by the method described above to give the desired crude peptide. This crude peptide is purified by various known purification means. Lyophilization of the major fraction gives the amide of the desired peptide.

To prepare the esterified peptide, for example, the α-carboxyl group of the carboxy terminal amino acid is condensed with a desired alcohol to prepare the amino acid ester, which is followed by procedure similar to the preparation of the amidated peptide above to give the ester form of the desired peptide.

The NPW antigen may be provided for direct immunization in its insolubilized form. The NPW antigen may also be bound or adsorbed to an appropriate carrier and the complex produced can be provided for immunization. A mixing ratio of the carrier to the NPW antigen (hapten) may be in any ratio of any type, as long as the antibody can be efficiently produced to the NPW antigen bound or adsorbed to the carrier. A high molecular carrier, which is conventionally used to produce an antibody to a hapten antigen, bound or adsorbed to the hapten in a weight ratio of 0.1 to 100 based on 1 of hapten may be used. As such a high molecular carrier, there are used a naturally occurring high molecular carrier and a synthetic high molecular carrier. Examples of the naturally occurring high molecular carrier used are serum albumin from mammals such as bovine, rabbit, human, etc., thyroglobulins from mammals such as bovine, rabbit, etc., hemoglobins from mammals such as bovine, rabbit, human, sheep, etc., or keyhole limpet hemocyanin. Examples of the synthetic high molecular carrier, which can be used, are various latexes including polymers, copolymers, etc., for example, polyamino acids, polystyrenes, polyacryls, polyvinyls, polypropylenes, etc.

For coupling of the hapten and the carrier, a variety of condensing agents can be used. Examples of the condensing agents, which are advantageously employed, are diazonium compounds such as bis-diazotized benzidine capable of crosslinking tyrosines, histidines or tryptophans; dialdehyde compounds such as glutaraldehyde, etc. capable of crosslinking amino groups with each other; diisocyanate compounds such as toluene-2,4-diisocyanate, etc.; dimaleimide compounds such as N,N'-o-phenylenedimaleimide, etc. capable of crosslinking thiols with each other; maleimide activated ester compounds capable of crosslinking an amino group with a thiol group; carbodiimide compounds capable of crosslinking an amino group with a carboxyl group; etc. In the crosslinking of amino groups with each other, one amino group is reacted with an activated ester reagent (e.g., SPDP, etc.) having dithiopyridyl group and then reduced to introduce the thiol group, whereas another amino group is introduced with a maleimide group using a maleimide activated ester reagent, and the two groups may be reacted with each other.

(2) Preparation of Monoclonal Antibody

The NPW antigen is administered to warm-blooded animal either solely or together with carriers or diluents to the site where the production of antibody is possible by administration routes such as intraperitoneally, intravenously, subcutaneously, etc. In order to potentiate the antibody productivity upon the administration, complete Freund's adjuvants or incomplete Freund's adjuvants may be administered. The administration is usually carried out once in every 2 to 6 weeks and approximately 2 to 10 times in total. Examples of the warm-blooded animal are monkeys, rabbits, dogs, guinea pigs, mice, rats, sheep, goats, fowl, etc. with mice being preferred for the preparation of monoclonal antibodies.

In the preparation of monoclonal antibodies, from warm-blooded animals, e.g., mice, immunized with the NPW antigen, the animal wherein the antibody titer is noted is selected, then the spleen or lymph node is collected after 2 to 5 days from the final immunization and antibody-producing cells contained therein are fused with myeloma cells to give anti-NPW monoclonal antibody-producing hybridomas. Measurement of the anti-NPW antibody titer in sera is made, for example, by reacting a labeled form of the NPW, which will be described later, with the antiserum followed by measuring the activity of the labeling agent bound to the antibody. The fusion may be operated, for example, by the known Kohler and Milstein method [Nature, 256, 495 (1975)]. Examples of fusion accelerators are polyethylene glycol (PEG), Sendai virus, etc., of which PEG is preferably employed. Examples of the myeloma cells are NS-1, P3U1, SP2/0, AP-1, etc. In particular, P3U1 or the like is preferably employed. A preferred ratio in count of the antibody-producing cells (spleen cells) to the myeloma cells used is within a range of approximately 1:1 to 20:1. When PEG (preferably, PEG 1000 to PEG 6000) is added in a concentration of approximately 10 to 80% followed by incubation generally at 20 to 40° C., preferably at 30 to 37° C. generally for 1 to 10 minutes, an efficient cell fusion can be carried out.

Various methods can be used for screening of the anti-NPW antibody-producing hybridomas. Examples of such methods include a method which comprises adding the hybridoma culture supernatant to a solid phase (e.g., microplate) adsorbed with the NPW or partial peptides thereof directly or together with a carrier, then adding an anti-immunoglobulin antibody (when mouse cells are used for the cell fusion, anti-mouse immunoglobulin antibody is used) labeled with a radioactive substance, an enzyme or the like, or Protein A and detecting the anti-NPW monoclonal antibody bound to the solid phase; a method which comprises adding the hybridoma culture supernatant to a solid phase adsorbed with an anti-immunoglobulin antibody or Protein A, adding the NPW labeled with a radioactive substance, an enzyme, etc. and detecting the NPW monoclonal antibodies bound to the solid phase; etc. Screening and plating of the anti-NPW monoclonal antibodies can be performed generally in a medium for animal cells (e.g., RPMI 1640) containing 10-20% fetal calf serum and supplemented with HAT (hypoxanthine, aminopterin and thymidine). The antibody titer in the hybridomas culture supernatant can be assayed as in the assay for the antibody titer in the antisera with the anti-NPW described above.

Separation and purification of the anti-NPW monoclonal antibody can be carried out by methods applied to conventional separation and purification of immunoglobulins, as in the conventional methods for separation and purification of polyclonal antibodies [e.g., salting-out, alcohol precipitation, isoelectric point precipitation, electrophoresis, adsorption and desorption with ion exchangers (e.g., DEAE), ultracentrifugation, gel filtration, or a specific purification method which involves collecting only an antibody with an activated adsorbent such as a antigen-binding solid phase, Protein A, Protein G, etc. and dissociating the binding to obtain the antibody; and the like].

As described above, the antibody of the present invention can be produced by culturing hybridoma cells in a warm-blooded animal in vivo or in vitro and collecting the antibody from the body fluids or culture medium.

Hybridomas that produce the anti-NPW antibody reacting with a segment (partial region) of the NPW and hybridomas that produce the anti-NPW monoclonal antibody reacting with the NPW but not reacting with its segment (partial region) can be screened, for example, by measuring the binding property of a peptide corresponding to the segment to an antibody produced by the hybridoma

[1] Method of Quantifying the NPW and Diagnosing Diseases Associated with the NPW Using the Antibody of the Present Invention Hereinafter, the method of quantifying the NPW (immunoassay, etc.) is described.

Using the antibody of the present invention, the NPW can be assayed and can also be detected by tissue staining, or the like. For these purposes, the antibody molecule itself may be used, or F(ab')2, Fab' or Fab fractions of the antibody molecule may be used.

The assaying method using the antibody of the present invention is not particularly limited. Any assaying method can be used, so long as the amount of antibody, antigen or antibody-antigen complex corresponding to the amount of antigen (e.g., the level of NPW) in a fluid to be tested can be detected by chemical or physical means and the amount of the antigen can be calculated from a standard curve prepared from standard solutions containing known amounts of the antigen. For such an assay method, for example, the sandwich assay, the competitive assay, the immunometric method, nephrometry, etc. are used, and the sandwich assay and the competitive assay described below are more preferred in terms of sensitivity and specificity, with the sandwich assay being particularly preferable.

(1) Sandwich Assay

After the antibody of the present invention immobilized on a carrier is reacted with a labeled form of the antibody of the present invention and a fluid to be tested, the activity of the labeling agent is measured to quantify the NPW in the test fluid.

Preferably, the sandwich assay includes:

(i) a method for quantification of the NPW in a test fluid, which comprises reacting the antibody specifically reacting with a partial peptide at the N-terminal region of the NPW immobilized on a carrier, a labeled form of the antibody specifically reacting with a partial peptide at the C-terminal region and the test fluid, and measuring the activity of the label;

(ii) a method for quantification of the NPW in a test fluid, which comprises reacting the antibody specifically reacting with a partial peptide at the C-terminal region of the NPW immobilized onto a carrier, the antibody specifically reacting with a partial peptide at the N-terminal region of a labeled form of the NPW and the test fluid, and measuring the activity of the label; etc.

A more preferred technique of the sandwich assay includes a method for quantification, wherein the antibody specifically reacting with a partial peptide at the N-terminal region of the NPW is the monoclonal antibody represented by AhW23N2G6D1a or the monoclonal antibody represented by AhW23N3H3E4a, and the antibody specifically reacting with a partial peptide at the C-terminal region of the NPW is (a) the monoclonal antibody represented by AhW23C6G1H8a or the monoclonal antibody represented by AhW23C5G2F6a, or (b) a monoclonal antibody represented by ArW30C3A1Aa or a monoclonal antibody represented by ArW30C7F2E8a. These antibodies are preferably used in a labeled form with horseradish peroxidase (HRP).

In the sandwich assay, the immobilized antibody of the present invention is reacted with a test fluid (primary reaction), then with a labeled form of antibody of the present invention (secondary reaction), and the activity of the labeling agent on the immobilizing carrier is measured, whereby the NPW level in the test fluid can be quantified. The primary and secondary reactions may be performed simultaneously or with some time intervals. The methods of labeling and immobilization can be performed by modifications of those methods described above. In the immunoassay by the sandwich assay, the antibody used for immobilized or labeled antibody is not necessarily from one species, but a mixture of two or more species of antibodies may be used to increase the measurement sensitivity, etc. In the method of assaying NPW by the sandwich assay, for example, when the antibodies used in the primary reaction recognize the partial peptides at the C-terminal region of NPW, the antibodies used in the secondary reaction are preferably those recognizing partial peptides other than the C-terminal region (i.e., the N-terminal region). When the antibodies used for the primary reaction recognize partial peptides at the N-terminal region of NPW, the antibodies used in the secondary reaction, antibodies recognizing partial peptides other than the N-terminal region (i.e., the C-terminal region) are preferably employed.

(2) Competitive Assay

The antibody of the present invention, a test fluid and a labeled form of the NPW are competitively reacted and a ratio of the labeled NPW bound to the antibody is measured, thereby to quantify the NPW in the test fluid.

The competitive assay is performed by, e.g., a solid phase technique.

Specifically, anti-mouse IgG antibody (manufactured by ICN/CAPPEL) is used as a solid phase antibody, i) the antibody of the present invention (e.g., AhW23N2G6D1a; AhW23N3H3E4a, AhW23C6G1H8a, AhW23C5G2F6a, ArW30C3A1Aa, ArW30C7F2E8a, etc.), ii) the NPW labeled with horseradish peroxidase (HRP), and iii) a test fluid are added to a plate where the solid phase antibody is present; after the reaction, the HRP activity adsorbed onto the solid phase is measured to quantify the NPW.

(3) Immunometric Assay

In the immunometric assay, an antigen in a test fluid and a solid phase antigen are competitively reacted with a given amount of a labeled form of the antibody of the present invention followed by separating the solid phase from the liquid phase; or an antigen in a test fluid and an excess amount of labeled form of the antibody of the present invention are reacted, then a solid phase antigen is added to bind an unreacted labeled form of the antibody of the present invention to the solid phase and the solid phase is then separated from the liquid phase. Thereafter, the labeled amount of any of the phases is measured to determine the antigen level in the test fluid.

(4) Nephrometry

In the nephrometry, the amount of insoluble sediment, which is produced as a result of the antigen-antibody reaction in a gel or in a solution, is measured. Even when the amount of an antigen in a test fluid is small and only a small amount of the sediment is obtained, a laser nephrometry utilizing laser scattering can be suitably used.

Examples of labeling agents, which are employed for the aforesaid assay methods (1) to (4) using labeling agents, include radioisotopes (e.g., [$^{125}$I], [$^{131}$I], [$^{3}$H], [$^{14}$C], [$^{32}$P], [$^{33}$P], [$^{35}$S], etc.), fluorescent substances [e.g., cyanine fluorescent dyes (e.g., Cy2, Cy3, Cy5, Cy5.5, Cy7 (manufactured by Amersham Biosciences), etc.), fluorescamine, fluorescein isothiocyanate, etc.], enzymes (e.g., β-galactosidase, β-glucosidase, alkaline phosphatase, peroxidase, malate dehydrogenase, etc.), luminescent substances (e.g., luminol, a luminol derivative, luciferin, lucigenin, etc.), biotin, lanthanides, etc. In addition, a biotin-avidin system may be used as well for binding an antibody to a labeling agent.

In the immobilization of antigens or antibodies, physical adsorption may be used. Alternatively, chemical binding that is conventionally used for immobilization of proteins, enzymes, etc. may be used as well. Examples of the carrier include insoluble polysaccharides such as agarose, dextran, cellulose, etc.; synthetic resins such as polystyrene, polyacrylamide, silicone, etc.; or glass; and the like.

In applying each of these immunoassay techniques to the method of the present invention, it is not necessary to set any special condition, operation, etc. The assay system for the NPW may be constructed in addition to the conditions or operations conventionally used for each of the assay techniques, taking into account the technical consideration of one skilled in the art. For details of such conventional technical means, reference may be made to a variety of reviews, reference books, etc. [for example, see Hiroshi Irie (ed.): "Radioimmunoassay" (published by Kodansha, 1974); Hiroshi Irie (ed.): "Radioimmunoassay; Second Series" (published by Kodansha, 1979); Eiji Ishikawa, et al. (ed.): "Enzyme Immunoassay" (published by Igaku Shoin, 1978); Eiji Ishikawa, et al. (ed.): "Enzyme Immunoassay" (Second Edition) (published by Igaku Shoin, 1982); Eiji Ishikawa, et al. (ed.): "Enzyme Immunoassay" (Third Edition) (published by Igaku Shoin, 1987); "Methods in Enzymology" Vol. 70 (Immunochemical Techniques (Part A)); ibid., Vol. 73 (Immunochemical Techniques (Part B)); ibid., Vol. 74 (Immunochemical Techniques (Part C)); ibid., Vol. 84 (Immunochemical Techniques (Part D: Selected Immunoassays)); ibid., Vol. 92 (Immunochemical Techniques (Part E: Monoclonal Antibodies and General Immunoassay Methods)); ibid., Vol. 121 (Immunochemical Techniques (Part I: Hybridoma Technology and Monoclonal Antibodies)] (all published by Academic Press); etc.). Thus, where the NPW assay system of the present invention is constructed by applying the sandwich immunoassay method, its method is not limited to EXAMPLES later described.

Thus, the antibody of the present invention enables to quantify the NPW with high sensitivity and is useful for clarification of the physiological functions of NPW and for diagnosis of diseases associated with the NPW.

By determining the level of NPW contained in body fluids (e.g., blood, plasma, serum, urine, follicular fluid, spinal fluid, sperm, etc.) using the antibody of the present invention, it can be diagnosed that one suffers from the diseases associated with the NPW, [for example, anorexia, obesity (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity, etc.), pituitary tumor, diencephalon tumor, menstrual disorder, autoimmune disease, prolactinoma, sterility, impotence, amenorrhea, lactorrhea, acromegaly, Chiari-Frommel syndrome, Argonz-del Castillo syndrome, Forbes-Albright syndrome, lymphoma, Sheehan's syndrome, spermatogenesis disorder, renal dropsy, voiding dysfunction (e.g., bladder contractile dysfunction, obstruction of urethral flow, dysuria, urodynia, urinary obstruction, etc.), hyponatremia, syndrome of inappropriate secretion of anti-diuretic hormone (SIADH), hypertension, storage dysfunction (e.g., pollakiuria, urinary incontinence (e.g., urge incontinence, stress incontinence, functional incontinence, etc.), etc.), polyuria, diabetes insipidus (e.g., pituitary diabetes insipidus, renal diabetes insipidus, etc.), hypematremia, metabolic alkalosis, hypokalemia, Cushing's syndrome, upper digestive tract disorders (e.g., peptic ulcer (e.g., gastric ulcer, duodenal ulcer, marginal ulcer, Zollinger-Ellison syndrome, etc.), gastritis, reflux esophagitis, NUD (non-ulcer dyspepsia), gastric cancer, gastric MALT lymphoma, nonsteroidal anti-inflammatory drug-induced ulcer, hyperacidity, ulcer, etc.), dyspepsia (e.g., pituitary dyspepsia, renal dyspepsia, etc.), bone metabolism disorders (e.g., osteoporosis, osteomalacia, etc.), anemia (e.g., iron deficiency anemia, etc.), etc.], or it is highly likely that one would suffer from these diseases in the future.

For example, in diagnosis of gastric hyperacidity, the NPW level in a body fluid is quantified and when the NPW level is more abundant than in healthy conditions, e.g., its blood level is about 10 fmol/ml or more, preferably about 15 fmol/ml or more, it is diagnosed that one suffers from gastric hyperacidity.

[2] Pharmaceutical Comprising the Antibody of the Present Invention

The antibody of the present invention can neutralize the activities of the NPW (e.g., GPR7-binding activity, GPR8-binding activity, GPR7-cell stimulating activity, GPR8-cell stimulating activity, eating behavior suppressing activity, prolactin producing activity, antidiuretic activity, gastric acid secretion promoting activity, etc.) and hence, can be used as a safe pharmaceutical including an agent for preventing/treating diseases associated with the NPW, for example, anorexia, pituitary tumor, diencephalon tumor, menstrual disorder, autoimmune disease, prolactinoma, sterility, impotence, amenorrhea, lactorrhea, acromegaly, Chiari-Frommel syndrome, Argonz-del Castillo syndrome, Forbes-Albright syndrome, lymphoma, Sheehan's syndrome, spermatogenesis disorder, renal dropsy, voiding dysfunction (e.g., bladder contractile dysfunction, obstruction of urethral flow, dysuria, urodynia, urinary obstruction, etc.), hyponatremia, syndrome of inappropriate secretion of anti-diuretic hormone (SIADH), hypertension, upper digestive tract disorders (e.g., peptic ulcer (e.g., gastric ulcer, duodenal ulcer, marginal ulcer, Zollinger-Ellison syndrome, etc.), gastritis, reflux esophagitis, NUD (non-ulcer dyspepsia), gastric cancer, gastric MALT lymphoma, nonsteroidal anti-inflammatory drug-induced ulcer, hyperacidity, ulcer, etc.), etc., an eating (appetite) stimulant, and so on. Preferably, the antibody can be used as an agent for preventing/treating sterility, renal dropsy, peptic ulcer, gastric hyperacidity, etc.

The antibody of the present invention may be administered in its intact form or in the form of an appropriate pharmaceutical composition. The pharmaceutical composition used for administration described above may contain the aforesaid antibody or its salt and a pharmacologically acceptable carrier, a diluent or an excipient. Such a pharmaceutical composition is provided in a dosage form suitable for oral or parenteral administration.

Examples of the composition for parenteral administration are injectable preparations, suppositories, etc. The injectable preparations may include dosage forms such as intravenous, subcutaneous, intracutaneous and intramuscular injections, drip infusions, etc. These injectable preparations may be prepared by methods publicly known. For example, the injectable preparations may be prepared by dissolving, suspending or emulsifying the antibody of the present invention or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate dissolution aid such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a dissolution aid such as benzyl benzoate, benzyl alcohol, etc. The injection thus prepared is preferably filled in an appropriate ampule. The suppository used for rectal administration may be prepared by blending the aforesaid antibody or its salt with conventional bases for suppositories.

The composition for oral administration includes a solid or liquid dosage form, specifically, tablets (including dragees and film-coated tablets), pills, granules, powders, capsules (including soft capsules), syrups, emulsions, suspensions, etc. Such a composition is manufactured by publicly known methods and may contain carriers, diluents or excipients conventionally used in the field of pharmaceutical preparations. As the carriers and excipients for tablets e.g., lactose, starch, sucrose, magnesium stearate and the like are used.

Advantageously, the pharmaceutical compositions for oral or parenteral use described above are prepared into pharmaceutical preparations with a unit dose to fit a dose of the active ingredients. Such unit dose preparations include, for example, tablets, pills, capsules, injections (ampoules) and suppositories. The amount of the antibody contained is generally about 5 to about 500 mg per dosage unit form; it is preferred that the aforesaid antibody is contained in about 5 to about 100 mg especially in the form of injection, and in about 10 to 250 mg for the other forms.

Each of the compositions described above may further contain other active ingredients, unless any adverse interaction occurs due to blending with the antibody described above.

The preventive/therapeutic agent for diseases described above comprising the antibody of the present invention is low toxic, and can be administered orally or parenterally to human or mammals (e.g., rats, rabbits, sheep, swine, bovine, cats, dogs, monkeys, etc.) as it is, in the form of liquid preparations or as a pharmaceutical composition of appropriate dosage form. The dose may vary depending on subject to be administered, target disease, symptoms, route for administration, etc. When used for the treatment of, e.g., gastric hyperacidity in an adult patient, it is advantageous that the antibody of the present invention is parenterally administered in a single dose of normally about 0.01 to 20 mg/kg body weight, preferably about 0.1 to 10 mg/kg body weight and more preferably about 0.1 to 5 mg/kg body weight about 1 to 5 times, preferably approximately 1 to 3 times a day. For oral administration, the corresponding dose may be administered. When symptoms are extremely serious, the dose may be increased depending on the conditions.

In the specification of the present invention, when amino acids, etc. are shown by abbreviations, they are denoted in accordance with the IUPAC-IUB Commission on Biochemical Nomenclature or by the common codes in the art, examples of which are shown below. For amino acids that may have the optical isomer, L form is presented unless otherwise indicated.

Gly: glycine

Ala: alanine

Val: valine

Leu: leucine

Ile: isoleucine

Ser: serine

Thr: threonine

Cys: cysteine

Met: methionine

Glu: glutamic acid

Asp: aspartic acid

Lys: lysine

Arg: arginine

His: histidine

Phe: phenylalanine

Tyr: tyrosine

Trp: tryptophan

Pro: proline

Asn: asparagine

Gln: glutamine

TFA: trifluoroacetic acid

DMF: N,N-dimethylformamide

SPDP: N-succinimidyl-3-(2-pyrimidyldithio)propionate

GMBS: N-(4-maleimidobutyryloxy)succinimide

BSA: bovine serum albumin

BTG: bovine thyroglobulin

EIA: enzyme immunoassay

HPLC: reverse phase high performance liquid chromatography

HRP: horseradish peroxidase

FBS: fetal bovine serum d-FBS: dialyzed fetal bovine serum

TMB: 3,3',5,5'-tetramethylbenzidine

NMP: N-methylpyrrolidone

Boc: t-butyloxycarbonyl

Fmoc: 9-fluorenylmethyloxycarbonyl

DCC: N,N'-dichlorohexylcarbodiimide

Pbf: 2,2,4,6,7-pentamethyldihydrobenzofrane-5-sulfonyl tBu: tertiary butyl

Trt: trityl

Tos: p-toluenesulfonyl

DIEA: N,N-diisopropylethylamine

HOBt: 1-hydroxybenzotriazole

HOAt: 1-hydroxy-7-azabenzotriazole

PyAop: 7-azabenzotriazol-1-yloxytrispirolydinophophonium hexafluorophosphate

Clt: 2-chlorotrityl

BHA: benzhydrylamine

The sequence identification numbers used in the sequence listing of the specification represent the following sequences.

[SEQ ID NO: 1]
This shows the amino acid sequence of the peptide to prepare immunogen (in the present specification, sometimes referred to as peptide-1), which was used in EXAMPLE 1 described below.

[SEQ ID NO: 2]
This shows the amino acid sequence of the peptide to prepare immunogen (in the present specification, sometimes referred to as peptide-2), which was used in EXAMPLE 1 described below.

[SEQ ID NO: 3]
This shows the amino acid sequence of the peptide to prepare immunogen (in this specification, sometimes referred to as the peptide-3), which was used in EXAMPLE 1 described below.

[SEQ ID NO: 4]
This shows the amino acid sequence of human neuropeptide W (1-23) (in this specification, sometimes referred to as human NPW23).

[SEQ ID NO: 5]
This shows the amino acid sequence of human neuropeptide W (1-30) (in this specification, sometimes referred to as human NPW30).

[SEQ ID NO: 6]
This shows the amino acid sequence of rat neuropeptide W (1-23) (in this specification, sometimes referred to as rat NPW23).

[SEQ ID NO: 7]
This shows the amino acid sequence of rat neuropeptide W (1-30) (in this specification, sometimes referred to as rat NPW30).

[SEQ ID NO: 8]
This shows the amino acid sequence of mouse neuropeptide W (1-23) (in this specification, sometimes referred to as mouse NPW23).

[SEQ ID NO: 9]
This shows the amino acid sequence of mouse neuropeptide W (1-30) (in this specification, sometimes referred to as mouse NPW30).

[SEQ ID NO: 10]
This shows the amino acid sequence of porcine neuropeptide W (1-23) (in this specification, sometimes referred to as porcine NPW23).

[SEQ ID NO: 11]
This shows the amino acid sequence of porcine neuropeptide W (1-30) (in this specification, sometimes referred to as porcine NPW30).

[SEQ ID NO: 12]
This shows the amino acid sequence of the biotin-labeled peptide-1 prepared in EXAMPLE 1 described below Xaa shows the Cys residues labeled with Biotin (Long Arm) Maleimide (VECTOR LABORATORIES).

[SEQ ID NO: 13]
This shows the amino acid sequence of the biotin-labeled peptide-2 prepared in EXAMPLE 1 described below. Xaa shows the Cys residues labeled with Biotin (Long Arm) Maleimide (VECTOR LABORATORIES).

[SEQ ID NO: 14]
This shows the amino acid sequence of the biotin-labeled peptide-3 prepared in EXAMPLE 1 described below. Xaa shows the Cys residues labeled with Biotin (Long Arm) Maleimide (VECTOR LABORATORIES).

[SEQ ID NO: 15]
This shows the amino acid sequence of human GPR7.

[SEQ ID NO: 16]
This shows the base sequence of a DNA encoding the amino acid sequence represented by SEQ ID NO: 15.

[SEQ ID NO: 17]
This shows the amino acid sequence of human GPR8.

[SEQ ID NO: 18]
This shows the base sequence of a DNA encoding the amino acid sequence represented by SEQ ID NO: 17.

[SEQ ID NO: 19]
This shows the amino acid sequence of rat GPR7 (the same receptor protein as TGR26 described in public literature (WO 02/44368)).

[SEQ ID NO: 20]
This shows the base sequence of a DNA of the amino acid sequence represented by SEQ ID NO: 19.

The hybridoma, AhW23N2G6D1, obtained in EXAMPLE 1 later described has been deposited on International Patent Organisms Depository, National Institute of Advanced Industrial Science and Technology, located at Central 6, 1-1-1 Higashi, Tsukuba, Ibaraki (postal code: 305-8566) under Accession Number FERM. BP-8363 since Apr. 23, 2003.

The hybridoma, AhW23N3H3E4, obtained in EXAMPLE 1 later described has been deposited on International Patent Organisms Depository, National Institute of Advanced Industrial Science and Technology, located at Central 6, 1-1-1 Higashi, Tsukuba, Ibaraki (postal code: 305-8566) under Accession Number FERM BP-8364 since Apr. 23, 2003.

The hybridoma, AhW23C6G1H8, obtained in EXAMPLE 1 later described has been deposited on International Patent Organisms Depository, National Institute of Advanced Industrial Science and Technology, located at Central 6, 1-1-1 Higashi, Tsukuba, Ibaraki (postal code: 305-8566) under Accession Number FERM BP-8365 since Apr. 23, 2003.

The hybridoma, AhW23C5G2F6, obtained in EXAMPLE 1 later described has been deposited on International Patent Organisms Depository, National Institute of Advanced Industrial Science and Technology, located at Central 6, 1-1-1 Higashi, Tsukuba, Ibaraki (postal code: 305-8566) under Accession Number FERM BP-8366 since Apr. 23, 2003.

The hybridoma, ArW30C3A1A, obtained in EXAMPLE 1 later described has been deposited on International Patent Organisms Depository, National Institute of Advanced Industrial Science and Technology, located at Central 6, 1-1-1 Higashi, Tsukuba, Ibaraki (postal code: 305-8566) under Accession Number FERM BP-8367 since Apr. 23, 2003.

The hybridoma, ArW30C7F2E8, obtained in EXAMPLE 1 later described has been deposited on International Patent Organisms Depository, National Institute of Advanced Industrial Science and Technology, located at Central 6, 1-1-1 Higashi, Tsukuba, Ibaraki (postal code: 305-8566) under Accession Number FERM BP-8368 since Apr. 23, 2003.

The antibodies acquired from the respective hybridoma cells are shown by the cell names with suffix "a."

The antibodies obtained in EXAMPLES described below, i.e., 2G6-D1, 3H3-E4, 5G2-F6, 6G1-H8, 3A1A and 7F2-E8, are sometimes referred to as AhW23N2G6D1a, AhW23N3H3a, AhW23C5G2F6a, AhW23C6G1H8a, ArW30C3A1Aa and ArW30C7F2E8a, respectively.

Hereinafter, the present invention will be described in more detail, with reference to EXAMPLES and REFERENCE EXAMPLES, but they are not deemed to limit the scope of the present invention.

In this specification, human NPW23, rat NPW23, mouse NPW23 and porcine NPW23 are sometimes collectively referred to as NPW23. Also, human NPW30, rat NPW30, mouse NPW30 and porcine NPW30 are sometimes collectively referred to as NPW30. Further, NPW23 and NPW30 are sometimes collectively referred to as NPW.

EXAMPLE 1

Production of Anti-NPW Monoclonal Antibody (1) Preparation of the Immunogen to Produce an Antibody Binding to the Amino Terminal Region of NPW In order to prepare an antibody binding to the amino terminal region of NPW, a peptide (peptide-1, SEQ ID NO: 1) in which cysteine was added at the carboxyl terminus of a peptide composed of amino terminal 13 residues of human NPW23 was conjugated to porcine thyroglobulin via the cysteine residue to prepare the immunogen.

To a solution of 35.0 mg of porcine thyroglobulin (SIGMA) in 2.5 ml of phosphate-buffered saline (PBS, Nissui Pharma), 9.1 mg of sulfosuccinimidyl 4-(N-maleimidomethyl) cyclohexane-1 carboxylate (Sulfo-SMCC, PIERCE) was added. The mixture was stirred at room temperature for an hour. The porcine thyroglobulin, which reacted with Sulfo-SMCC, was separated from the unreacted Sulfo-SMCC present in large excess by means of a molecular sieve chromatography using PD-10 (Amersham Biosciences). To the porcine thyroglobulin reacted with Sulfo-SMCC, 4 mg of peptide-1 (SEQ ID NO: 1) previously dissolved in 0.2 ml of 0.1% acetic acid solution and 1.8 ml of PBS were added. The mixture was stirred at 4° C. for 16 hours to obtain the conjugate of peptide-1 and porcine thyroglobulin. The conjugate of peptide-1 and porcine thyroglobulin was used as the immunogen to produce the antibody binding to the amino terminal region of NPW.

(2) Preparation of the Immunogen to Produce an Antibody Binding to the Carboxyl Terminal Region of NPW23

In order to prepare an antibody binding to the carboxyl terminal region of NPW23, a peptide (peptide-2, SEQ ID NO: 2) in which cysteine was added at the amino terminus of a peptide composed of carboxyl terminal 13 residues of human NPW23 was conjugated to porcine thyroglobulin via the cysteine residue to prepare the immunogen.

To a solution of 35.2 mg of porcine thyroglobulin in 2.5 ml of PBS, 9.1 mg of Sulfo-SMCC was added. The mixture was stirred at room temperature for an hour. The porcine thyroglobulin, which reacted with Sulfo-SMCC, was separated from the unreacted Sulfo-SMCC present in large excess by means of a molecular sieve chromatography using PD-10. To the porcine thyroglobulin reacted with Sulfo-SMCC, 4 mg of peptide-2 (SEQ ID NO: 2) previously dissolved in 0.2 ml of 0.1% acetic acid solution and 1.8 ml of PBS were added. The mixture was stirred at 4° C. for 16 hours to obtain the conjugate of peptide-2 and porcine thyroglobulin. The conjugate of peptide-2 and porcine thyroglobulin was used as the immunogen to produce an antibody binding to the carboxyl terminal region of NPW23.

(3) Preparation of the Immunogen to Produce an Antibody Binding to the Carboxyl Terminal Region of NPW30

In order to prepare an antibody binding to the carboxyl terminal region of NPW30, a peptide (peptide-3, SEQ ID NO: 3) in which cysteine was added at the amino terminus of a peptide composed of carboxyl terminal 15 residues of rat NPW30 was conjugated to porcine thyroglobulin via the cysteine residue to prepare the immunogen.

To a solution of 20.0 mg of keyhole limpet hemocyanin (KLH, PIERCE) in 2.5 ml of PBS, 5.0 mg of Sulfo-SMCC was added, and the mixture was stirred at room temperature for an hour. The KLH, which reacted with Sulfo-SMCC, was separated from the unreacted Sulfo-SMCC present in large excess by means of a molecular sieve chromatography using PD-10. To the KLH reacted with Sulfo-SMCC, 4 mg of peptide-3 (SEQ ID NO: 3) previously dissolved in 0.2 ml of 0.1% acetic acid solution and 1.8 ml of PBS were added. The mixture was stirred at 4° C. for 16 hours to obtain the conjugate of peptide-3 and porcine thyroglobulin. The conjugate of peptide-3 and porcine thyroglobulin was used as the immunogen to produce an antibody binding to the carboxyl terminal region of NPW30.

(4) Mouse Immunization

Freund's complete adjuvant was mixed with each of the immunogens prepared by the procedures described in (1), (2) and (3), and the mixture corresponding to 0.1 mg of each peptide (peptide-1, peptide-2 or peptide-3) was intraperitoneally injected to Balb/c mice (female, 6-8 weeks old), respectively. Approximately 4 weeks after the primary immunization, the immunogens prepared by the procedures described in (1), (2) and (3) were mixed with Freund's incomplete adjuvant and the mixture corresponding to 0.05 mg of each peptide (peptide-1, peptide-2 or peptide-3) was intraperitoneally injected to Balb/c mice (female, 6-8 weeks old) which received the primary immunization, respectively. Subsequently to the second immunization, a mixture of the immunogen corresponding to 0.05 mg of each peptide and Freund's incomplete adjuvant was injected for boostering at every 2 week intervals until the antibody titer increased.

(5) Labeling by Biotinylation of Peptide-1, Peptide-2 and Peptide-3

The cysteine residues of peptide-1 (SEQ ID NO: 1), peptide-2 (SEQ ID NO: 2) and peptide-3 (SEQ ID NO: 3) were labeled with biotin to synthesize biotin-labeled peptide-1, peptide-2 and peptide-3. After 50 nmol of each peptide and 500 nmol of Biotin (Long Arm) Maleimide (VECTOR LABORATORIES) were dissolved in 0.5 ml of 0.1 M phosphate buffer (pH 7.0), the solution was kept warm at 37° C. for 3 hours. The products in which only the cysteine residues of peptide-1, peptide-2 and peptide-3 were labeled with biotin were fractionated on HPLC, respectively, to obtain biotin-labeled peptide-1 (SEQ ID NO: 12), biotin-labeled peptide-2 (SEQ ID NO: 13) and biotin-labeled peptide-3 (SEQ ID NO: 14).

(6) Assay for the Antibody Titer of Antibody Binding to the Amino Terminal Region of NPW The antibody titer of antibody binding to the amino terminal region of NPW was assayed by enzyme immunoassay using the biotin-labeled peptide-1 (SEQ ID NO: 12). An anti-mouse IgG-immobilized plate was prepared as follows. A dilution of goat anti-mouse IgG (Fc) (ICN Biomedicals) in 50 mM carbonate buffer (pH 9.6) in 10 µg/ml was dispensed in a 96-well immunoplate in 100 µl/well, which was left to stand at 4° C. for 3 days. The solution in the wells was discarded and Block Ace (Snow Brand Milk Products) was added to the well in 350 µl/well, which was left to stand at 4° C. for 3 days. The solution in each well was discarded and PBS containing 3% sucrose and 0.1% bovine serum albumin (BSA) was added to the well in 350 µl/well, which was left to stand at 4° C. for 1 day. The solution in each well was discarded and dried in a descicator for 3 days. The plate was then stored at 4° C. until used.

The sera collected from mice immunized with the conjugate of peptide-1 and porcine thyroglobulin prepared in the procedures described in (1) above were diluted in various magnifications with 0.1% BSA-containing PBS. After 50 µl of the serum dilution, 50 µl of 0.1% BSA-containing PBS or NPW23 solution and 50 µl of dilutions of the biotin-labeled peptide-1 solution prepared by the procedures described in (5) above in 0.1% BSA-containing PBS to 1000-64000 fold were added to each well of the anti-mouse IgG-immobilized plate prepared as described above, which was then left to stand at room temperature for 2 to 3 hours. The solution in each well was discarded and the well was washed 4 times with distilled water containing 0.9% sodium chloride and 0.05% Tween 20. A solution of streptoavidin-horseradish peroxide (HRP) conjugate (Calbiochem) was diluted with 0.1% BSA-containing PBS to 12000-fold, and 100 µl of the resulting dilution was added to each well, which was then left to stand at room temperature for an hour. The solution in each well was discarded and the well was washed 4 times with distilled water containing 0.9% sodium chloride and 0.05% Tween 20. The substrate for HRP was prepared by dissolving 10 mg of orthophenylenediamine tablet (SIGMA) in 11 ml of 66 mM aqueous disodium hydrogen phosphate 12-hydrate solution containing 33 mM citric acid and 0.015% hydrogen peroxide. To each well was added 100 µl of this substrate solution, which was then left to stand at room temperature for 10 to 30 minutes. After the reaction was terminated by adding 100 µl of 2N sulfuric acid to each well, absorbance of the substrate solution was measured at 492 nm. When the absorbance of well is high, it means that the antibody binding to the amino terminal region of NPW is present in the sera. When absorbance decreases almost to the background level by addition of excess NPW, it means that binding of this antibody to the amino terminal region of NPW is sequence-specific.

(7) Assay for the Antibody Titer of Antibody Binding to the Carboxyl Terminal Region of NPW23

The antibody titer of antibody binding to the carboxyl terminal region of NPW23 was assayed by enzyme immunoassay using the biotin-labeled peptide-2 (SEQ ID NO: 13). The anti-mouse IgG-immobilized plate was prepared by the procedures described in (6) above. The sera collected from mice immunized with the conjugate of peptide-2 and porcine thyroglobulin prepared in the procedures described in (2) above were diluted in various magnifications with 0.1% BSA-containing PBS. After 50 µl of the serum dilution, 50 µl of 0.1% BSA-containing PBS or NPW23 solution and 50 µl of dilutions of the biotin-labeled peptide-2 solution prepared by the procedures described in (5) above in 0.1% BSA-containing PBS to 1000-64000 fold were added to each well of the anti-mouse IgG-immobilized plate, which was then left to stand at room temperature for 2 to 3 hours. The solution in each well was discarded and the well was washed 4 times with distilled water containing 0.9% sodium chloride and 0.05% Tween 20. A solution of streptavidin-HRP conjugate was diluted with 0.1% BSA-containing PBS to 12000-fold and 100 µl of the resulting dilution was added to each well, which was then left to stand at room temperature for an hour. The solution in each well was discarded and the well was washed 4 times with distilled water containing 0.9% sodium chloride and 0.05% Tween 20. The substrate for HRP was prepared as in EXAMPLE 8. To each well was added 100 µl of this substrate solution, which was then left to stand at room temperature for 10 to 30 minutes. The reaction was terminated by adding 100 µl of 2N sulfuric acid to each well, and absorbance of the substrate solution was measured at 492 nm. When the absorbance of well is high, it means that the antibody binding to the carboxyl terminal region of NPW23 is present in the sera. When the absorbance decreases almost to the background-level by addition of excess NPW23, it means that binding of this antibody to the carboxyl terminal region of NPW23 is sequence-specific.

(8) Assay for the Antibody Titer of Antibody Binding to the Carboxyl Terminal Region of NPW30

The antibody titer of antibody binding to the carboxyl terminal region of NPW30 was assayed by enzyme immunoassay using the biotin-labeled peptide-3 (SEQ ID NO: 14). The anti-mouse IgG-immobilized plate was prepared by the procedures described in (6) above. The sera collected from mice immunized with the conjugate of peptide-3 and KLH prepared in the procedures described in (3) above were diluted in various magnifications with 0.1% BSA-containing PBS. After 50 µl of the serum dilution, 50 µl of 0.1% BSA-containing PBS or NPW30 solution and 50 µl of dilutions of the biotin-labeled peptide-3 solution prepared by the procedures described in (5) above in 0.1% BSA-containing PBS to 1000-64000 fold were added to each well of the anti-mouse IgG-immobilized plate, which was then left to stand at room temperature for 2 to 3 hours. The solution in each well was discarded and the well was washed 4 times with distilled water containing 0.9% sodium chloride and 0.05% Tween 20. A solution of streptavidin-HRP conjugate was diluted with 0.1% BSA-containing PBS to 12000-fold and 100 µl of the resulting dilution was added to each well, which was then left to stand at room temperature for an hour. The solution in each well was discarded and the well was washed 4 times with distilled water containing 0.9% sodium chloride and 0.05% Tween 20. The substrate for HRP was prepared as in EXAMPLE 8. To each well was added 100 µl of this substrate solution, which was then left to stand at room temperature for 10 to 30 minutes. The reaction was terminated by adding 100 µl of 2N sulfuric acid to each well, and absorbance of the substrate solution was measured at 492 nm. When the absorbance of well is high, it means that the antibody binding to the carboxyl terminal region of NPW30 is present in the sera. When the absorbance decreases almost to the background level by addition of excess NPW30, it means that binding of this antibody to the carboxyl terminal region of NPW30 is sequence-specific.

(9) Cell Fusion, Screening of Antibody-Producing Hybridoma, Acquisition of Monoclonal Antibodies and Collection of Ascites Fluid The antibody titer to each antigen in sera from the mice immunized by the method described in (4) above was assayed by the method described in (6), (7) or (8). A solution of 0.05 mg of the immunogen showing a relatively high antibody titer against the mice in 50 µl of PBS was intravenously injected to the mice for final immunization. The spleen was withdrawn from each mouse after 3 to 4 days from the fmol immunization, pressed against a stainless mesh, filtered and suspended in RPMI 1640 to give the spleen cell suspension. As the cells used for cell fusion, Balb/c-derived myeloma cell P3X63Ag8.653 was used. The cell fusion was carried out by a modification of the original method (Kohler, G. & Milstein, C., Nature, 256, 495, 1975). That is, spleen cells and P3X63Ag8.653 were washed 3 times with serum-free RPMI 1640 and mixed in a 10:1 proportion of the spleen cells to P3X63Ag8.653 cells. The mixture was centrifuged at 800 rpm for 15 minutes to deposit the cells. After the supernatant was thoroughly removed, the deposit was lightly loosened and 0.2 ml of polyethylene glycol (HYBRI-MAX, SIGMA) was added thereto over 30 seconds, then 5 ml of RPMI 1640 over 2 minutes and finally 5 ml of RPMI 1640. This liquid mixture was kept warm at 37° C. for 3 minutes to perform the cell fusion. The fusion was followed by centrifugation at a centrifugal rate of 600 rpm for 15 minutes. RPMI 1640 medium containing HAT ($1\times10^{-4}$M hypoxanthine, $4\times10^{-7}$M aminopterin and $1.6\times10^{-3}$M thymidine) and 10% calf fetal serum was added to the cell deposit to adjust the cell count of P3X63Ag8.653 to $2-3\times10^5$ cells per 0.2 ml, and 0.2 ml/well was plated on a 96-well plate. When the culture medium turned yellow on Days 9-14 after start of the incubation, the supernatant was collected and the antibody titer in the culture supernatant of the cell-fused hybridoma was assayed by the method described in (6), (7) or (8) above.

The presence of the antibody specifically binding to the amino terminus of NPW, the carboxyl terminus of NPW23 or the carboxyl terminus of NPW30 was confirmed in the hybridoma culture supernatant. Next, these hybridomas were cloned by limiting dilution. To a 96-well plate on which thymocytes from Balb/c mice had been previously plated in $5\times10^5$ cells/well, 100 µl of culture medium (RPMI 1640 containing HAT and 10% calf fetal serum) containing one hybridoma in average was added, respectively. After incubation for 10 days, the antibody titer in the culture supernatant in the well where only one colony of the hybridoma grew was assayed, and each hybridoma producing an antibody specific to the amino terminus of NPW, the carboxyl terminus of NPW23 or the carboxyl terminus of NPW30 was screened.

The hybridoma screened as above was intraperitoneally injected to nude mice administered with 0.5 ml of pristane (Balb/c AnNCrj-nu/nu, female, 6 to 8 weeks old) in $1\times10^6$ to $5\times10^6$/mouse, and 6 to 20 days later, the antibody-containing ascites fluid was collected. From the ascites fluid collected, the monoclonal antibody was purified using a protein A column. That is, 6 to 20 ml of ascites fluid was diluted in an equal volume of binding buffer (1.5M glycine buffer (pH 9.0) containing 3.5M NaCl and 0.05% $NaN_3$). The dilution was then provided through a protein A-cellulose (Seikagaku Corporation) column, which had been previously equilibrated with the binding buffer, to elute the specific antibody with an eluting buffer (0.1 M citrate buffer containing 0.05% $NaN_3$, pH 3.0). The eluate containing this antibody was neutralized and concentrated with Centriplus YM-50 (Amicon). PBS was added to the antibody concentrate and concentration with Centriplus YM-50 was repeated, whereby the buffer in which the antibody was dissolved was replaced by PBS.

(10) Monoclonal Antibodies Binding to the Amino Terminal Region of NPW

With regard to four monoclonal antibodies, i.e., 2G6-D1, 3H3-E4, 5E6-C3 and 7F9-E12, obtained from the hybridomas producing antibodies specifically binding to the amino terminal region of NPW, which were acquired by the procedure described in (9) above, it was confirmed by enzyme immunoassay that these antibodies recognized peptide-1 (SEQ ID NO: 1), human NPW23 (SEQ ID NO: 4) and human NPW30 (SEQ ID NO: 5). A mouse IgG-immobilized plate was prepared as follows. Goat anti-mouse IgG (Fc) (ICN Biomedicals) was diluted in 50 mM carbonate buffer (pH 9.6) to 10 µg/ml and the resulting dilution was charged in a 96-well immunoplate in 150 µl/well, which was then left to stand at 4° C. for a day. The solution in the well was discarded and Block Ace was added to the well in 200 µl/well. The plate was stored at 4° C. until used.

The culture supernatant of hybridoma producing the 2G6-D1, 3H3-E4, 5E6-C3 or 7F9-E12 antibody was diluted in EIA buffer (0.1% BSA, 0.4% sodium chloride, 2 mM EDTA, 0.05% CHAPS (3-((3-cholamidopropyl)dimethylammonio)-1-propanesulfonate), 20 mM phosphate buffer (pH 7.0)) in fixed magnifications (50 to 1000-fold), respectively. To the mouse IgG-immobilized plates, 50 µl each of solutions of these antibodies, 50 µl each of solutions of peptide-1 (SEQ ID NO: 1), human NPW23 (SEQ ID NO: 4) or human NPW30 (SEQ ID NO: 5) diluted in EIA buffer to various concentrations and 50 µl of a biotin-labeled peptide-1 solution diluted in EIA buffer to 75000-fold were added. After these plates were left to stand at 4° C. for 16 hours, each well was washed with PBS. To each well, 150 µl of streptoavidin-HRP solution diluted in EIA buffer to 20000-fold was added, which was then left to stand at room temperature for 2 hours. After the plate was washed with PBS, 150 µl of TMB Microwell Peroxidase Substrate (KIRKEGAARD & PERRY LAB., INC.) was added thereto and left to stand at room temperature. After the reaction was terminated by adding 75 µl of 1M phosphoric acid, the absorbance was measured at 450 nm using a plate reader (BICHROMTIC, manufactured by Dainippon Pharmaceutical Co., Ltd.). In this reaction system, the relative binding (%) is used to mean a relative value to a value obtained by subtracting absorbance of the well added with EIA buffer and biotin-labeled peptide-1 solution from absorbance of each well, when a value obtained by subtracting absorbance of the well added with EIA buffer and biotin-labeled peptide-1 solution from absorbance of the well added with the antibody solution, EIA buffer and biotin-labeled peptide-1 solution is made 100% binding.

As shown in FIGS. 1, 2, 3 and 4, the binding of 2G6-D1, 3H3-E4, 5E6-C3 and 7F9-E12 antibodies to biotin-labeled peptide-1 was concentration-dependently inhibited by peptide-1, human NPW23 and human NPW30.

This means that the 2G6-D1, 3H3-E4, 5E6-C3 and 7F9-E12 antibodies recognize the amino terminal region of NPW and bind to NPW.

The hybridomas producing 2G6-D1 (AhW23N2G6D1a) and 3H3-E4 (AhW23N3H3a) which are antibodies specifically recognizing the amino terminal region of NPW were named AhW23N2G6D1 and AhW23N3H3E4, respectively.

(11) Monoclonal Antibodies Binding to the Carboxyl Terminal Region of NPW23

With regard to six monoclonal antibodies, i.e., 2F1B2A, 5A2A, 5D6-F10, 5G2-F6, 6G1-H8 and 7B4-D2, obtained from the hybridomas producing antibodies specifically binding to the carboxyl terminal region of NPW23, which were acquired by the procedure described in (9) above, it was confirmed by enzyme immunoassay that these antibodies recognized peptide-2 (SEQ ID NO: 2) and human NPW23 (SEQ ID NO: 4). The mouse IgG-immobilized plate was prepared according to (10) described above. The culture supernatant of hybridoma producing the 2F1B2A, 5A2A, 5D6-F10, 5G2-F6, 6G1-H8 or 7B4-D2 antibody was diluted in EIA buffer described in (10) above in fixed magnifications (30 to 1000-fold), respectively. To the mouse IgG-immobilized plates, 50 µl each of these antibody solutions, 50 µl each of solutions of peptide-2 (SEQ ID NO: 2), human NPW23 (SEQ ID NO: 4) or human NPW30 (SEQ ID NO: 5) diluted in EIA buffer to various concentrations and 50 µl of a biotin-labeled peptide-2 solution diluted in EIA buffer to fixed magnifications (75000 to 225000-fold) were added. After these plates were left to stand at 4° C. for 16 hours, each well was washed with PBS. To each well, 150 μl of streptoavidin-HRP solution diluted in EIA buffer to 20000-fold was added, which was then left to stand at room temperature for 2 hours. After the plate was washed with PBS, 150 μl of TMB Microwell Peroxidase Substrate was added thereto and left to stand at room temperature. After the reaction was terminated by adding 75 μl of 1M phosphoric acid, the absorbance was measured at 450 nm on the plate reader. In this reaction system, the relative binding (%) is used to mean a relative value to a value obtained by subtracting absorbance of the well added with EIA buffer and biotin-labeled peptide-2 solution from absorbance of each well, when a value obtained by subtracting absorbance of the well added with EIA buffer and biotin-labeled peptide-2 solution from absorbance of the well added with the antibody solution, EIA buffer and biotin-labeled peptide-2 solution is made 100% binding.

As shown in FIGS. 5, 6, 7, 8, 9 and 10, the binding of 2F1B2A, 5A2A, 5D6-F10, 5G2-F6, 6G1-H8 and 7B4-D2 antibodies to biotin-labeled peptide-2 was inhibited by peptide-2 and human NPW23.

This means that the 2F1B2A, 5A2A, 5D6-F10, 5G2-F6, 6G1-H8 and 7B4-D2 antibodies recognize the carboxyl terminal region of NPW23 and bind to NPW23.

The hybridomas producing 5G2-F6 (AhW23C5G2F6a) and 6G1-H8 (AhW23C6G1H8a) which are antibodies specifically recognizing the carboxyl terminal region of NPW23 were named AhW23C5G2F6 and AhW23C6G1H8, respectively.

(12) Monoclonal Antibodies Binding to the Carboxyl Terminal Region of NPW30

With regard to three monoclonal antibodies, i.e., 2A1A, 3A1A and 7F2-E8, obtained from the hybridomas producing antibodies specifically binding to the carboxyl terminal region of NPW30, which were acquired by the procedure described in (9) above, it was confirmed by enzyme immunoassay that these antibodies recognized peptide-3 (SEQ ID NO: 3) and human NPW30 (SEQ ID NO: 5). The mouse IgG-immobilized plate was prepared according to (10) described above. The culture supernatant of hybridomas producing the 2A1A, 3A1A or 7F2-E8 antibody was diluted in EIA buffer described in (10) above to 100-fold. To the mouse IgG-immobilized plates, 50 μl each of these antibody solutions, 50 μl each of solutions of peptide-3 (SEQ ID NO: 3), human NPW23 (SEQ ID NO: 4) or human NPW30 (SEQ ID NO: 5) diluted in EIA buffer to various concentrations and 50 μl of a biotin-labeled peptide-3 solution diluted in EIA buffer to 100000-fold were added. After these plates were left to stand at 4° C. for 16 hours, each well was washed with PBS. To each well, 150 μl of streptoavidin-HRP solution diluted in EIA buffer to 20000-fold was added, which was then left to stand at room temperature for 2 hours. After the plate was washed with PBS, 150 μl of TMB Microwell Peroxidase Substrate was added thereto and left to stand at room temperature. After the reaction was terminated by adding 75 μl of 1M phosphoric acid, the absorbance was measured at 450 nm on the plate reader. In this reaction system, the relative binding (%) is used to mean a relative value to a value obtained by subtracting absorbance of the well added with EIA buffer and biotin-labeled peptide-3 solution from absorbance of each well, when a value obtained by subtracting absorbance of the well added with EIA buffer and biotin-labeled peptide-3 solution from absorbance of the well added with the antibody solution, EIA buffer and biotin-labeled peptide-3 solution is made 100% binding.

Figure 11:
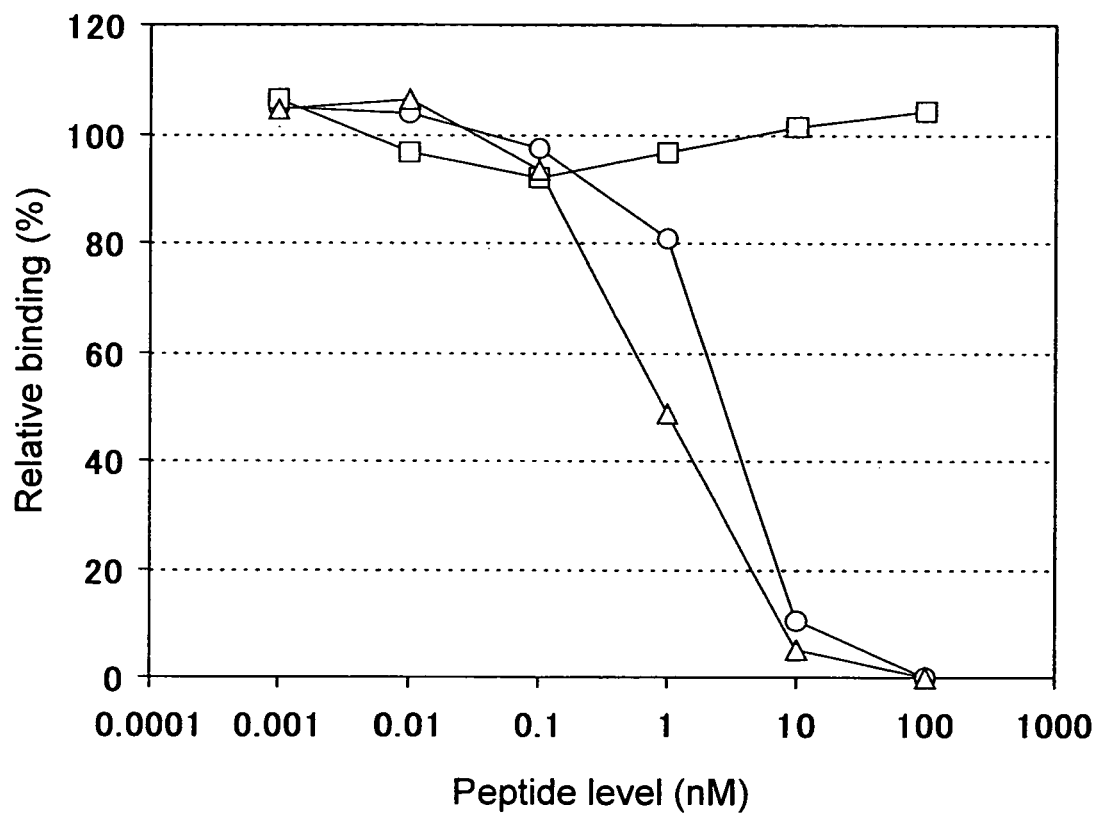
FIG. 11 shows binding inhibition by peptide-3, human NPW23 or human NPW30 against the binding of monoclonal antibody 2A1A to biotin-labeled peptide-3. In the figure, -○- (-open circle-) represents the case where peptide-3 is added, -□- (-open square-) represents the case where human NPW23 is added, and -Δ- (-open triangle-) represents the case where human NPW30 is added, respectively.
Figure 12:
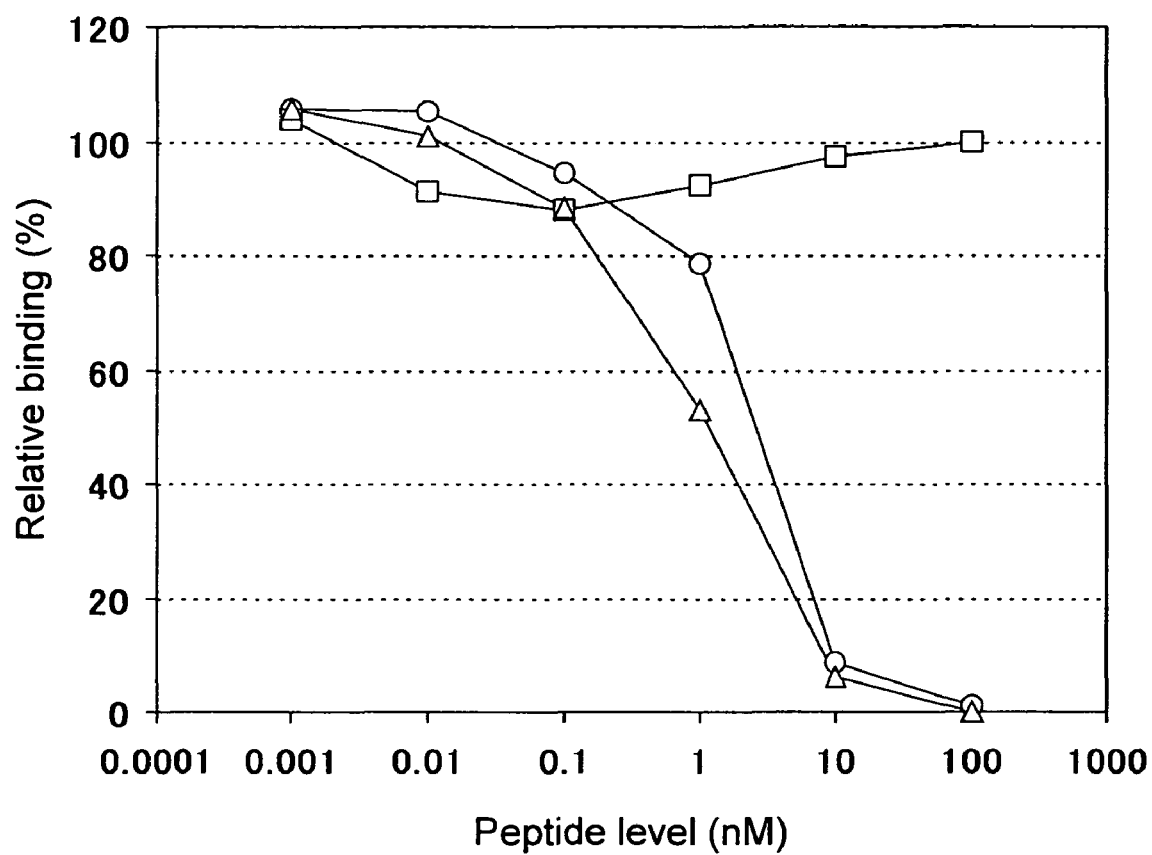
FIG. 12 shows binding inhibition by peptide-3, human NPW23 or human NPW30 against the binding of monoclonal antibody 3A1A to biotin-labeled peptide-3. In the figure, -○- (-open circle-) represents the case where peptide-3 is added, -□- (-open square-) represents the case where human NPW23 is added, and -Δ- (-open triangle-) represents the case where human NPW30 is added, respectively.
Figure 13:
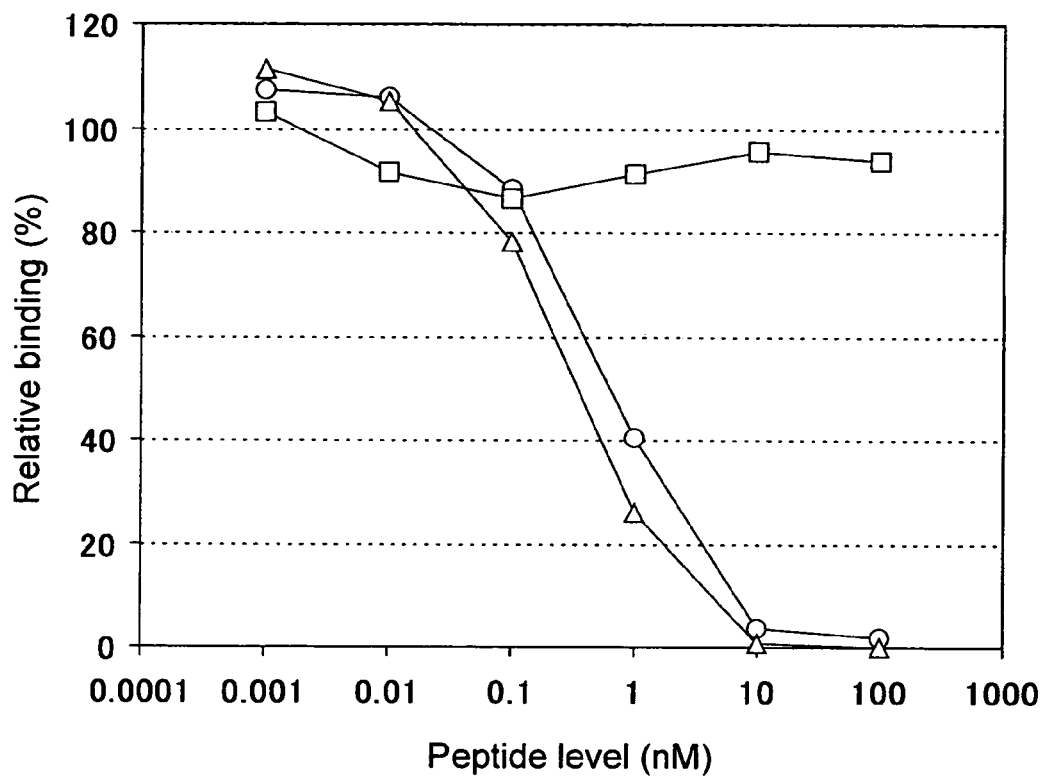
FIG. 13 shows binding inhibition by peptide-3, human NPW23 or human NPW30 against the binding of monoclonal antibody 7F2-E8 to biotin-labeled peptide-3. In the figure, -○- (-open circle-) represents the case where peptide-3 is added, -□- (-open square-) represents the case where human NPW23 is added, and -Δ- (-open triangle-) represents the case where human NPW30 is added, respectively.

As shown in FIGS. 11, 12 and 13, the binding of 2A1A, 3A1A and 7F2-E8 antibodies to biotin-labeled peptide-3 was inhibited by peptide-3 and human NPW30. This means that the 2A1A, 3A1A and 7F2-E8 antibodies recognize the carboxyl terminal region of NPW30 and bind to NPW30.

The hybridomas producing 3A1A (ArW30C3A1Aa) and 7F2-E8 (ArW30C7F2E8a) which are antibodies specifically recognizing the carboxyl terminal region of NPW30 were named ArW30C3A1A and ArW30C7F2E8, respectively.

EXAMPLE 2

Suppression of the Agonist Activity by Anti-NPW Monoclonal Antibodies

The activity of suppressing the agonist activity of NPW by the monoclonal antibodies described in EXAMPLE 1-(10), 1-(11) and 1-(12) was examined. NPW was reacted with the anti-NPW monoclonal antibodies at room temperature for an hour. Thereafter, the reaction solution was added to the human GPR7-expressing CHO cell line (SEQ ID NO: 15) produced by the method described in WO 02/93161, the human GPR8-expressing CHO cell line (SEQ ID NO: 17) produced by the method described in WO 01/98494 or the rat GPR7-expressing CHO cell line (the same receptor as TGR26 described in WO 02/44368) (SEQ ID NO: 19) produced by the method described in WO 02/44368, whereby the activity of inhibiting the cAMP accumulation in these cells by forskolin (FSK) stimulation was determined.

MEMα medium, pH 7.4, containing 20 mM HEPES, 0.05% BSA, 2 μM FSK and 0.2 mM 3-isobutyl-1-methylxantine (IBMX) was used as a buffer for diluting each NPW and each anti-NPW monoclonal antibody used in this EXAMPLE (hereinafter referred to as dilution buffer). A mixture of 2 nM of each NPW prepared using the dilution buffer and each anti-NPW monoclonal antibody IgG in various concentrations was kept warm at room temperature for an hour. The human GPR7-expressing CHO cell line, human GPR8-expressing CHO cell line or rat GPR7-expressing CHO cell line was plated on a 24-well plate in $5 \times 10^4$, followed by incubation for 2 days. Prior to adding the reaction solution of each NPW and each NPW antibody, each well was washed 3 times with 0.5 ml of MEMα medium containing 20 mM HEPES, 0.05% BSA and 0.2 mM IBMX (hereinafter referred to as wash buffer) and then 0.5 ml/well of the wash buffer was added to the well, followed by incubation for 30 minutes. After further washing 3 times with 0.5 ml of the wash buffer, 0.25 ml/well of the wash buffer and 0.25 ml/well of the reaction solution of NPW and anti-NPW antibody were added to the well. After keeping warm at 37° C. for 30 minutes, 0.1 ml of 20% perchloric acid was added to each well to terminate the intracellular cAMP synthesis reaction. Next, the 24-well plate was placed on ice for an hour thereby to extract cAMP. The cAMP level in the extract was determined using the cAMP EIA system (Amersham Biosciences). The relative value (%) in cAMP accumulation is a relative ratio of the value obtained by subtracting the intracellular cAMP level without addition of FSK from the intracellular cAMP level with addition of the assay sample to the value obtained by subtracting the intracellular cAMP level without addition of FSK from the intracellular cAMP level with FSK stimulation only.

Figure 14:
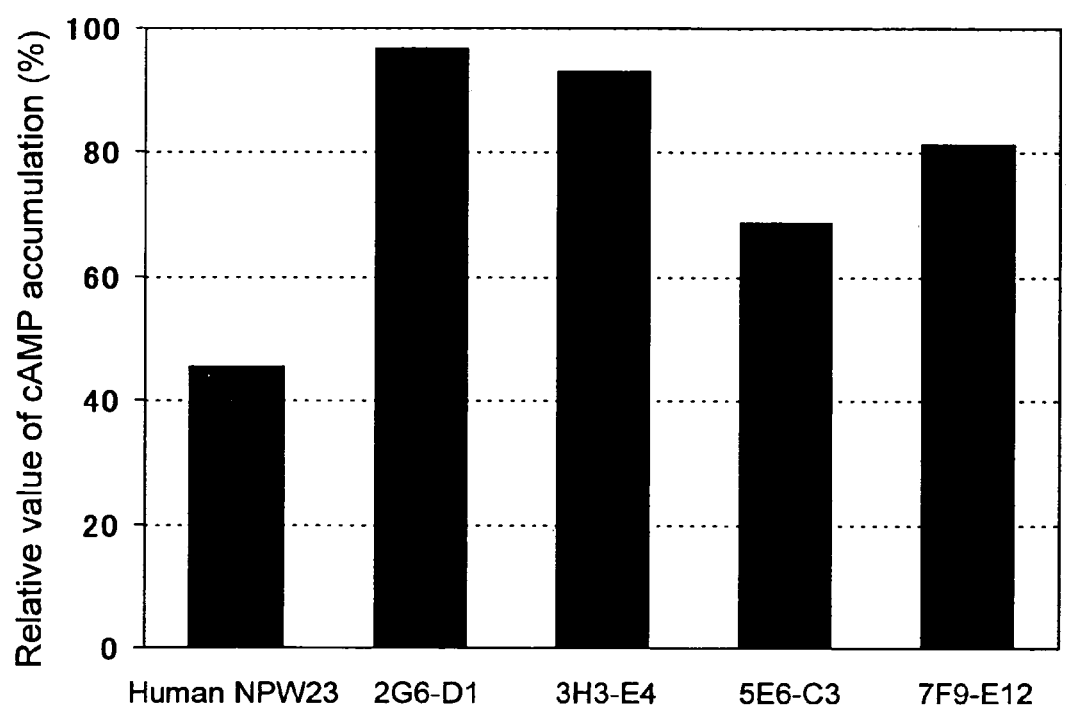
FIG. 14 shows suppression of the cAMP synthesis inhibiting activity of human NPW23 by the monoclonal antibody recognizing the amino terminus of NPW. The case wherein it was added to human GPR7-expressed cells is shown.

Human NPW23 (SEQ ID NO: 4) was reacted with 2G6-D1, 3H3-E4, 5E6-C3 and 7F9-E12 as the monoclonal antibodies recognizing the amino terminus of NPW. Thereafter, the reaction solution was given to the human GPR7-expressing cell line or human GPR8-expressing cell line. By giving human NPW23 alone, the cAMP level in human GPR7-expressed cells decreased to 46% as compared to the case where FSK stimulation only was made. By reacting human NPW23 with 2G6-D1, 3H3-E4, 5E6-C3 and 7F9-E12 in a molar ratio of 30-fold excess, however, the cAMP levels in human GPR7-expressed cells were recovered to 97%, 93%, 69% and 81%, respectively, as compared to the case where FSK stimulation only was made. The results are shown in FIG. 14.

Figure 15:
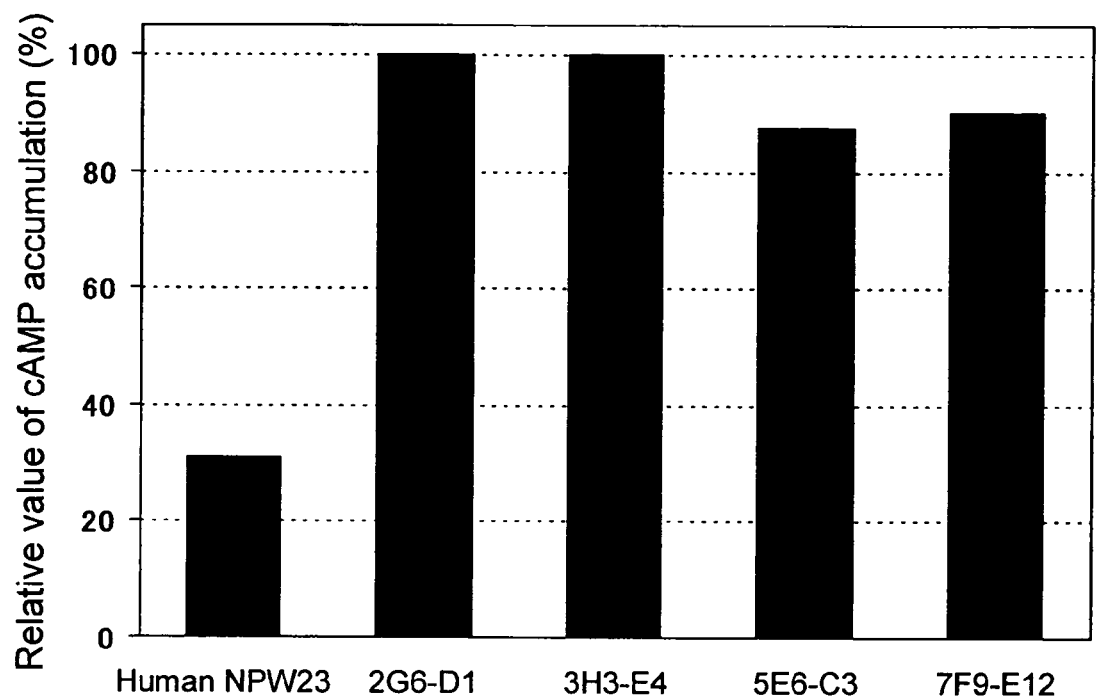
FIG. 15 shows suppression of the cAMP synthesis inhibiting activity of human NPW23 by the monoclonal antibody recognizing the amino terminus of NPW. The case wherein it was added to human GPR8-expressed cells is shown.

On the other hand, when human NPW23 alone was given, the cAMP level in human GPR8-expressed cells decreased to 31% as compared to the case where FSK stimulation only was made. By reacting human NPW23 with 2G6-D1, 3H3-E4, 5E6-C3 and 7F9-E12 in a molar ratio of 30-fold excess, however, the cAMP levels in human GPR8-expressed cells were recovered to 100%, 100%, 87% and 90%, respectively, as compared to the case where FSK stimulation only was made. The results are shown in FIG. 15.

These results mean that 2G6-D1, 3H3-E4, 5E6-C3 and 7F9-E12 suppress the cAMP synthesis inhibiting activity of human NPW23.

Figure 16:
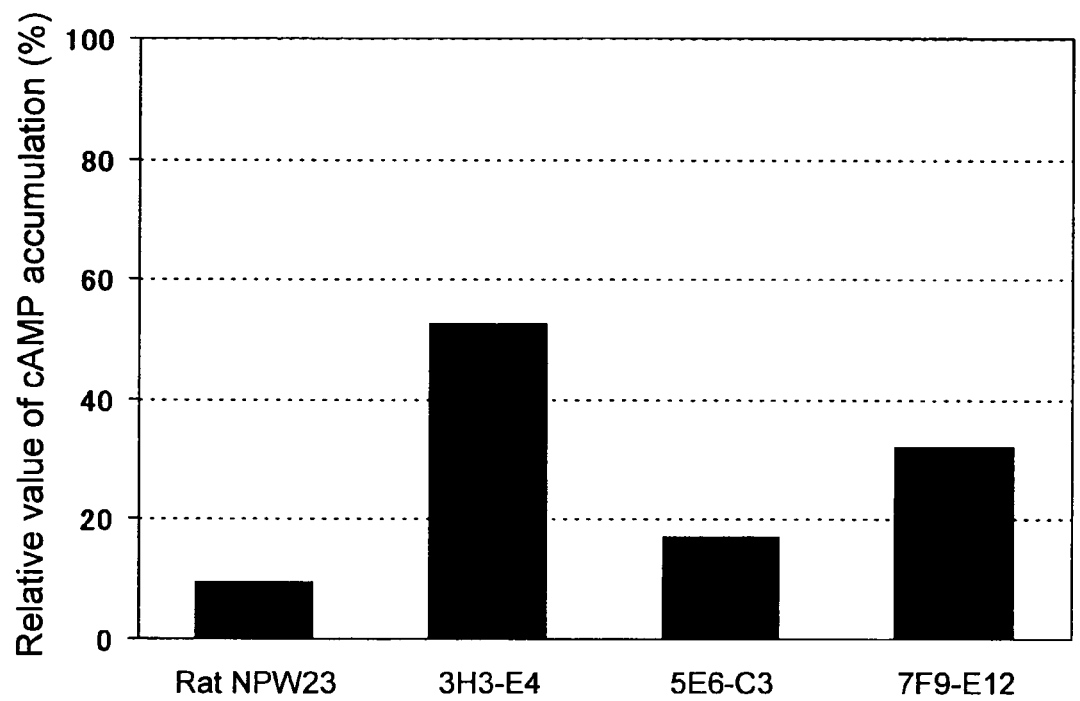
FIG. 16 shows suppression of the cAMP synthesis inhibiting activity of rat NPW23 by the monoclonal antibody recognizing the amino terminus of NPW.

Rat NPW23 (SEQ ID NO: 6) was reacted with 3H3-E4, 5E6-C3 and 7F9-E12 as the monoclonal antibodies recognizing the amino terminus of NPW. Thereafter, the reaction solution was given to the rat GPR7-expressing cell line. By giving rat NPW23 alone, the cAMP level in rat GPR7-expressed cells decreased to 9% as compared to the case where FSK stimulation only was made. By reacting rat NPW23 with 3H3-E4, 5E6-C3 and 7F9-E12 in a molar ratio of 30-fold excess, however, the cAMP levels in GPR7-expressed cells were recovered to 53%, 17% and 32%, respectively, as compared to the case where FSK stimulation only was made. The results are shown in FIG. 16.

These results mean that 3H3-E4, 5E6-C3 and 7F9-E12 suppress the cAMP synthesis inhibiting activity of rat NPW23.

Figure 17:
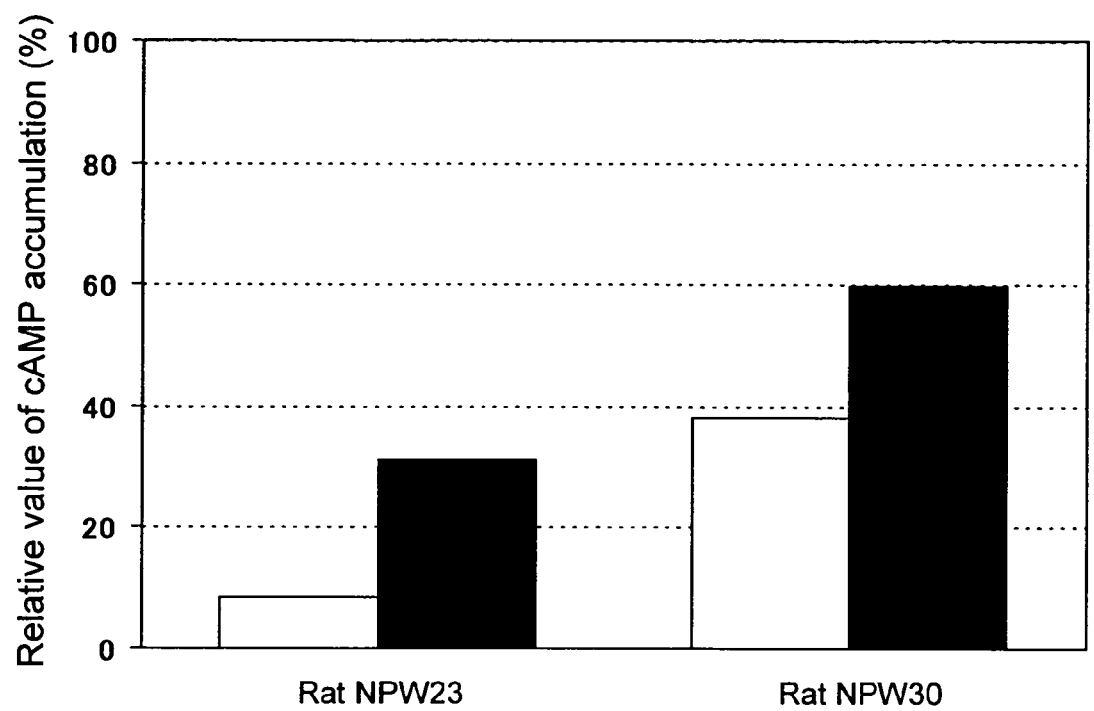
FIG. 17 shows suppression of the cAMP synthesis inhibiting activity of rat NPW23 and rat NPW30 by monoclonal antibody 2G6-D1. In the figure, symbol □ (open square) shows the case where rat NPW alone was added and ■ (closed square) shows the case where rat NPW and 2G6-D1 antibody were added.

Rat NPW23 or rat NPW30 (SEQ ID NO: 7) was reacted with 2G6-D1 as the monoclonal antibody recognizing the amino terminus of NPW. Thereafter, the reaction solution was given to the rat GPR7-expressing cell line. By giving rat NPW23 or rat NPW30 alone, the cAMP levels in rat GPR7-expressed cells decreased to 8% and 31%, respectively, as compared to the case where FSK stimulation only was made. By reacting rat NPW23 or rat NPW30 with 2G6-D1 in a molar ratio of 30-fold excess, however, the cAMP levels in GPR7-expressed cells were recovered to 38% and 60% respectively, as compared to the case where FSK stimulation only was made. The results are shown in FIG. 17.

These results mean that 2G6-D1 suppress the cAMP synthesis inhibiting activity of rat NPW23 or rat NPW30.

Figure 18:
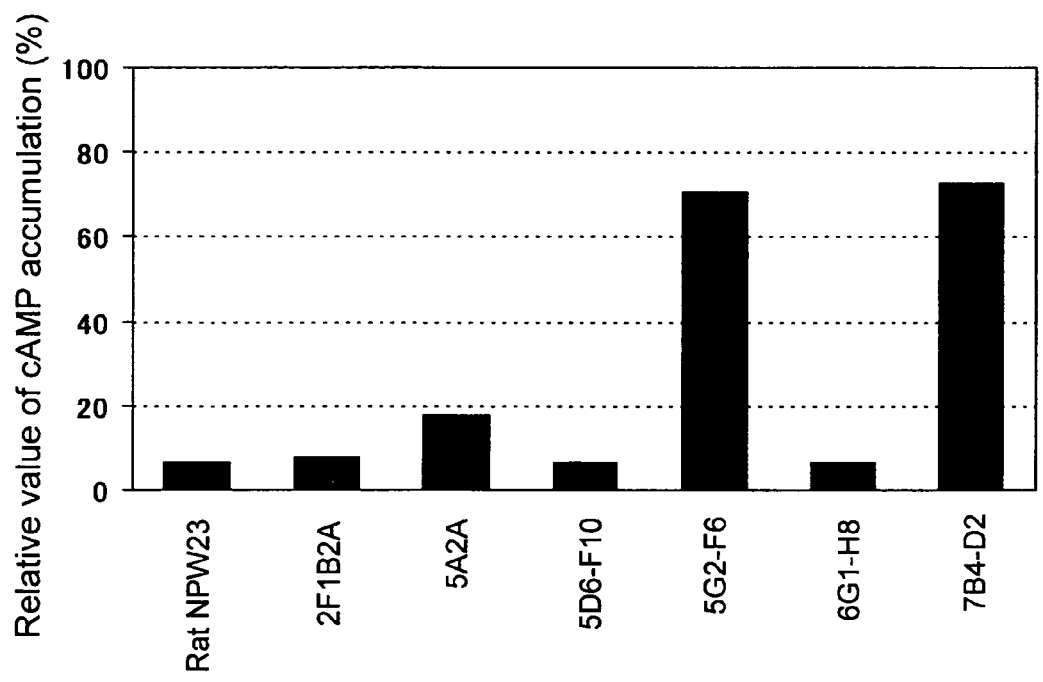
FIG. 18 shows suppression of the cAMP synthesis inhibiting activity of rat NPW23 by the monoclonal antibody recognizing the carboxyl terminus of NPW23.

Rat NPW23 was reacted with 2F1B2A, 5A2A, 5D6-F10, 5G2-F6, 6G1-1H8 and 7B4-D2 as the monoclonal antibodies recognizing the carboxyl terminus of NPW. Thereafter, the reaction solution was given to the rat GPR7-expressing cell line. By giving rat NPW23 alone, the cAMP level in rat GPR7-expressed cells decreased to 7% as compared to the case where FSK stimulation only was made. Rat NPW23 was reacted with 2F1B2A, 5A2A, 5D6-F10, 5G2-F6, 6G1-H8 and 7B4-D2 in a molar ratio of 30-fold excess. When reacted with 5A2A, 5G2-F6 and 7B4-D2, the cAMP levels in GPR7-expressed cells were recovered to 16%, 71% and 73%, respectively, as compared to the case where FSK stimulation only was made. The results are shown in FIG. 18.

These results mean that 5A2A, 5G2-F6 and 7B4-D2 suppress the cAMP synthesis inhibiting activity of rat NPW23.

Figure 19:
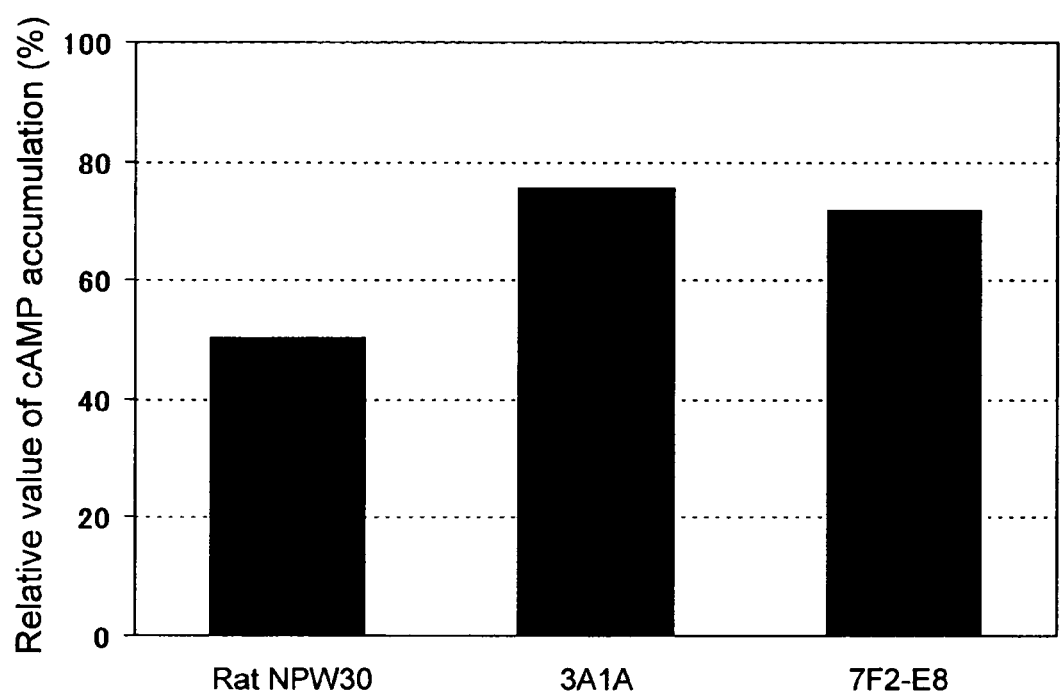
FIG. 19 shows suppression of the cAMP synthesis inhibiting activity of rat NPW30 by the monoclonal antibody recognizing the carboxyl terminus of NPW30.
Figure 20:
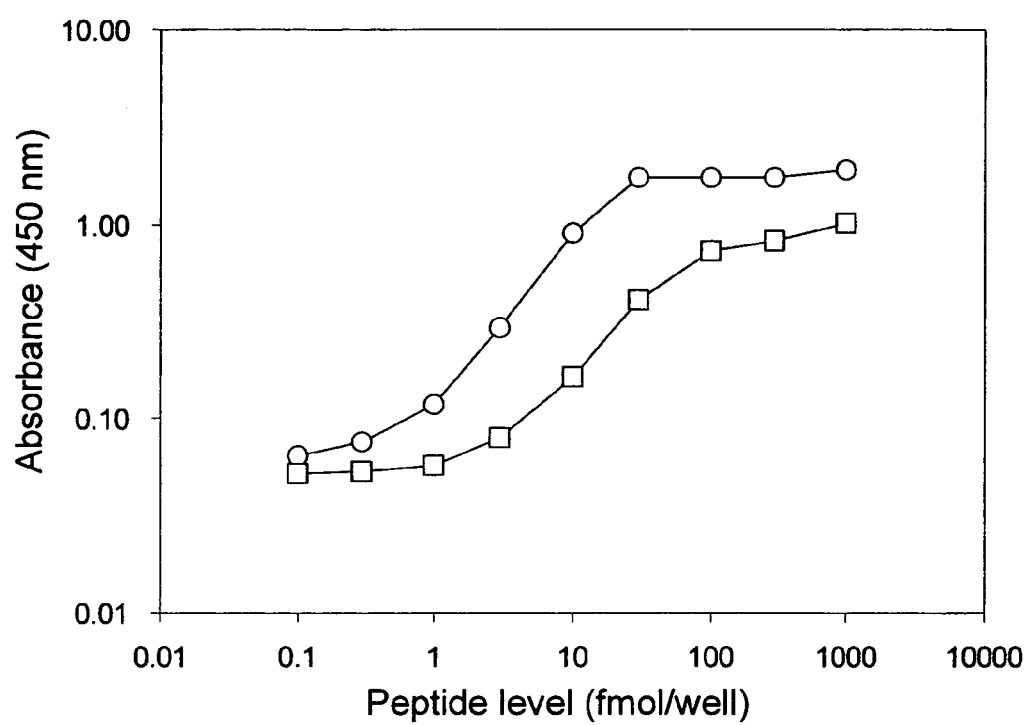
FIG. 20 shows absorbance at 450 nm when human NPW23 and rat (mouse) NPW23 were added to the EIA system using monoclonal antibody 2F1B2A in various levels. In the figure, -○- (-open circle-) indicates the case where human NPW23 was added and -□- (-open square-) indicates the case where rat (mouse) NPW23 was added, respectively.
Figure 21:
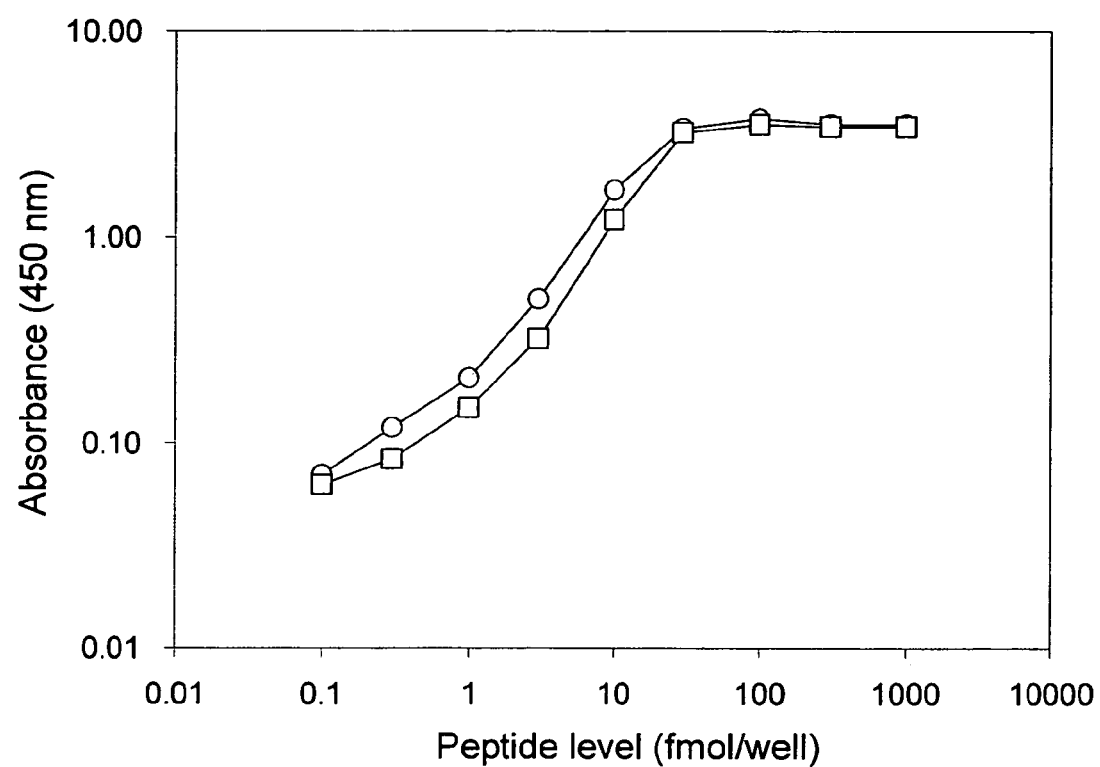
FIG. 21 shows absorbance at 450 nm when human NPW23 and rat (mouse) NPW23 were added to the EIA system using monoclonal antibody 5A2A in various levels. In the figure, -○- (-open circle-) indicates the case where human NPW23 was added and -□- (-open square-) indicates the case where rat (mouse) NPW23 was added, respectively.
Figure 22:
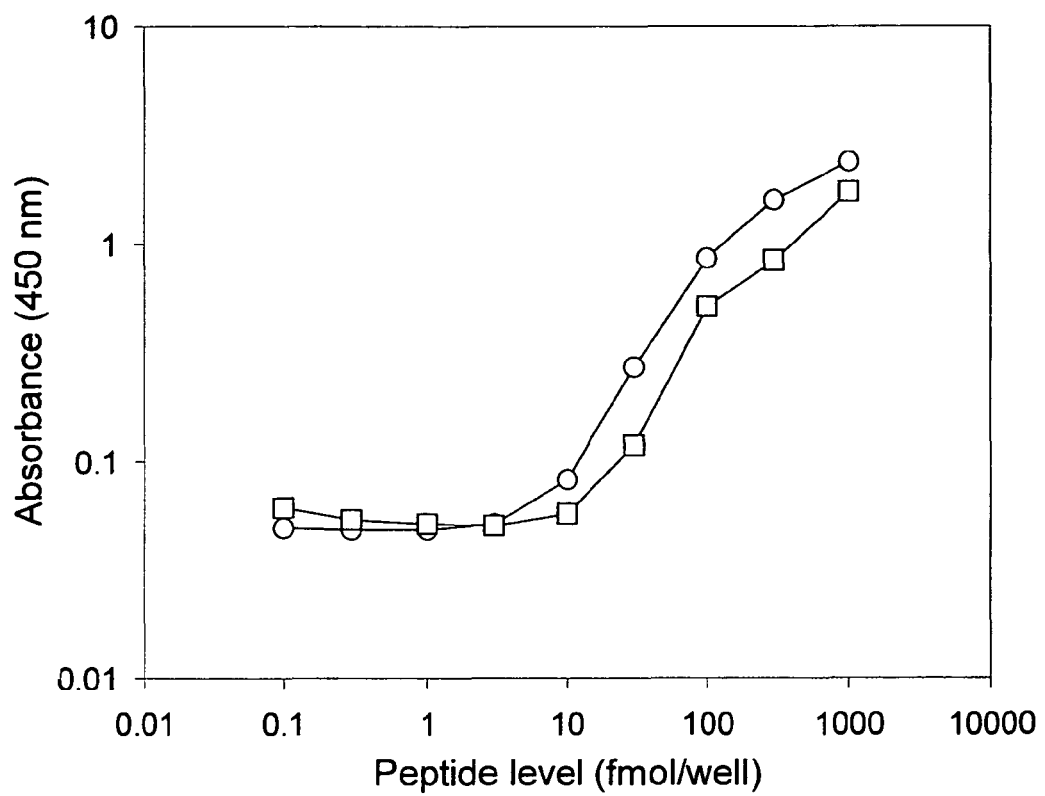
FIG. 22 shows absorbance at 450 nm when human NPW23 and rat (mouse) NPW23 were added to the EIA system using monoclonal antibody 5D6-F10 in various levels. In the figure, -○- (-open circle-) indicates the case where human NPW23 was added and -□- (-open square-) indicates the case where rat (mouse) NPW23 was added, respectively.
Figure 23:
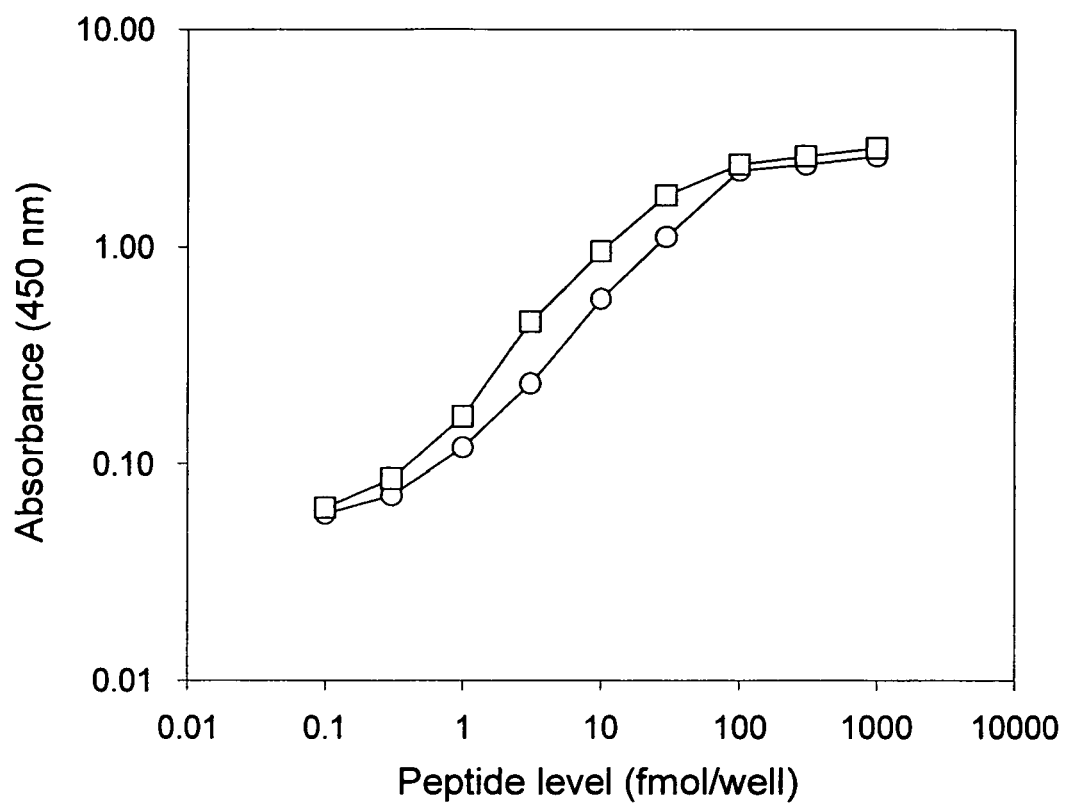
FIG. 23 shows absorbance at 450 nm when human NPW23 and rat (mouse) NPW23 were added to the EIA system using monoclonal antibody 5G2-F6 in various levels. In the figure, -○- (-open circle-) indicates the case where human NPW23 was added and -□- (-open square-) indicates the case where rat (mouse) NPW23 was added, respectively.
Figure 24:
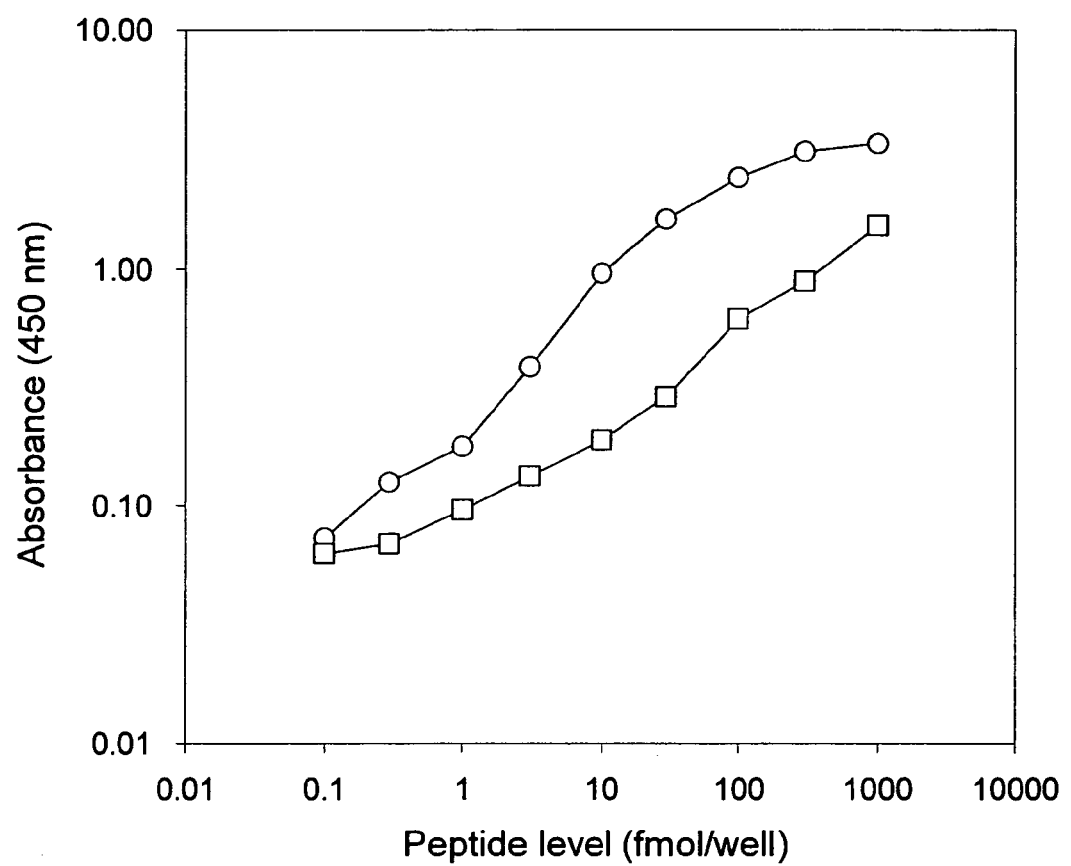
FIG. 24 shows absorbance at 450 nm when human NPW23 and rat (mouse) NPW23 were added to the EIA system using monoclonal antibody 6G1-H8 in various levels. In the figure, -○- (-open circle-) indicates the case where human NPW23 was added and -○- (-open square-) indicates the case where rat (mouse) NPW23 was added, respectively.
Figure 25:
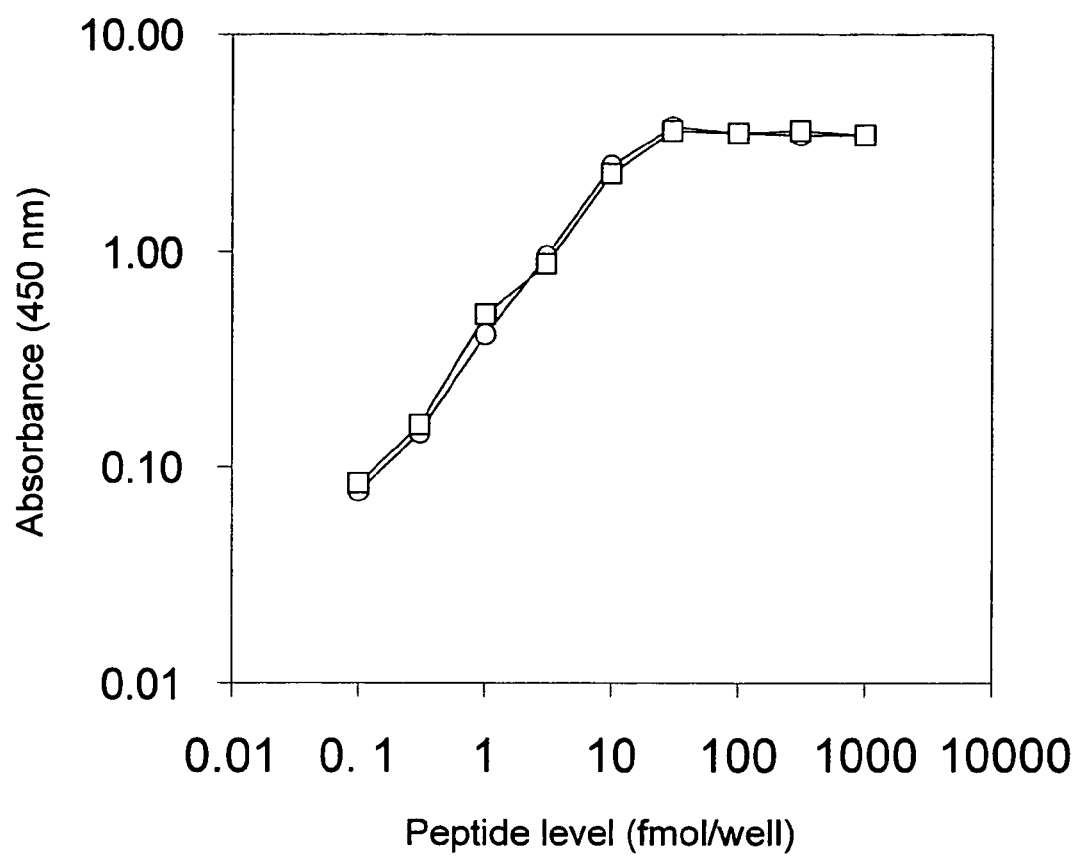
FIG. 25 shows absorbance at 450 nm when human NPW23 and rat (mouse) NPW23 were added to the EIA system using monoclonal antibody 7B4-D2 in various levels. In the figure, -○- (-open circle-) indicates the case where human NPW23 was added and -○- (-open square-) indicates the case where rat (mouse) NPW23 was added, respectively.

Rat NPW30 was reacted with 3A1A and 7F2-E8 as the monoclonal antibodies recognizing the carboxyl terminus of NPW. Thereafter, the reaction solution was given to the rat GPR7-expressing cell line. By giving rat NPW30 alone, the cAMP level in rat GPR7-expressed cells decreased to 50% as compared to the case where FSK stimulation only was made. By reacting rat NPW30 with 3A1A and 7F2-E8 in a molar ratio of 150-fold excess, the cAMP levels in GPR7-expressed cells were recovered to 75% and 72%, respectively, as compared to the case where FSK stimulation only was made. The results are shown in FIG. 19.

These results mean that 3A1A and 7F2-E8 suppress the cAMP synthesis inhibiting activity of rat NPW30.

EXAMPLE 3

Establishment of the Double Antibody EIA System for Quantifying NPW23 and NPW30

(1) Preparation of Enzyme-Labeled Antibody Capable of Recognizing the Amino Terminus of NPW The monoclonal antibody 2G6-D1 capable of recognizing the amino terminus of NPW was labeled with an enzyme by following procedure. One liter of a solution of 4.4 mg of 2G6-D1 IgG in 2 ml of PBS was dialyzed against 0.1 M phosphate buffer (pH 6.7) at 4° C. for 16 hours. After a solution of 6.4 mM N-(4-maleimidobutyryloxy)-succinimide (GMBS, Dojin Chemical) in 50 µl of N, N-dimethylformamide (DMF) was added to the dialyzed IgG solution, the solution mixture was left to stand at room temperature for 40 minutes while stirring. The reaction solution was applied to a Sephadex G-25 (Amersham Biosciences) column to perform molecular sieve chromatography (buffer: 0.1 M phosphate buffer (pH 6.7), flow rate: 0.5 ml/min) at 4° C. Thus, the IgG fraction was obtained. At the same time, a solution of 45.5 mM N-succinimidyl 3-(2-pyridyldithio)propionate (SPDP, Wako Pure Chemical) in 60 µl of DMF was added to a solution of 7.3 mg of HRP in 1.1 ml of 20 mM phosphate buffer (pH 6.8) containing 0.1 M sodium chloride. The solution mixture was left to stand at room temperature for 40 minutes while stirring. A solution of 5.48 mM of dithiothreitol (DTT, Wako Pure Chemical) in 400 µl of 100 mM acetate buffer (pH 4.5) was added to the reaction solution of HRP and SPDP, and the solution mixture was left to stand at room temperature for 20 minutes while stirring. The reaction solution was applied to a Sephadex G-25 column to perform molecular sieve chromatography (buffer: 0.1 M phosphate buffer (pH 6.0) containing 0.2 mM EDTA, flow rate: 0.5 ml/min) at 4° C. Thus, the HRP fraction was obtained. A solution mixture of this HRP fraction and the IgG fraction shown above was concentrated to about 2 ml using Centriplus YM-10 (MILLIPORE) and the concentrated solution mixture was kept warm at 4° C. for 16 hours. The solution concentrate was applied to a Sephacryl S-300 (Amersham Biosciences) column to perform molecular sieve chromatography (buffer: 0.1 M phosphate buffer (pH 6.5), flow rate: 1.0 ml/min) at 4° C. Thus, the HRP-bound IgG was obtained. The HRP-bound IgG was used for double antibody EIA as the enzyme-labeled antibody (hereinafter referred to as HRP-labeled 2G6-D1).

(2) Establishment of the Double Antibody EIA System for Assaying NPW23

Six monoclonal antibodies 2F1B2A, 5A2A, 5D6-F10, 5G2-F6, 6G1-H8 or 7B4-D2 binding to the carboxyl terminal region of NPW23 were dissolved in 50 mM carbonate buffer (pH 9.6) in 10 μg/ml, and 100 μl of the antibody solution was added to each well of a 96-well immunoplate (NUNC). The plate was left to stand at 4° C. for 16 hours. The solution in the well was then discarded and 200 μl/well of Block Ace was added to the well. The plate was stored at 4° C. until used. The NPW solution was diluted with the EIA buffer described in EXAMPLE 1-(10) in various concentrations and 100 μl of the dilution was added to each well. This plate was then left to stand at 4° C. for 16 hours. After the plate was washed 3 times with PBS, 100 μl of a HRP-labeled 2G6-D1 dilution in EIA buffer in fixed magnifications (300 to 1000-fold) was added to each well. The plate was then left to stand at 4° C. for 16 hours. After the plate was washed 4 times with PBS, 100 μl of the TMB Microwell Peroxidase Substrate System was added thereto to react them at room temperature. After the reaction was terminated by adding 50 μl of 1M phosphoric acid, the absorbance was measured at 450 nm on the plate reader. Increased absorbance at 450 nm was noted dependently on each of the peptide levels of human NPW23 (SEQ ID NO: 4), rat NPW23 (SEQ ID NO: 6) and mouse NPW23 (SEQ ID NO: 8 (the same as SEQ ID NO: 6)) added in the respective double antibody EIA systems. The results obtained using the monoclonal antibodies 2F1B2A, 5A2A, 5D6-F10, 5G2-F6, 6G1-H8 and 7B4-D2 are shown in FIGS. 20, 21, 22, 23, 24 and 25, respectively.

Using these double antibody EIA systems, a minimum of 0.3 fmol of NPW23 could be detected. Also, porcine NPW23 (SEQ ID NO: 10) can be determined using these double antibody techniques.

(3) Establishment of the Double Antibody EIA System for Assaying NPW30

Figure 26:
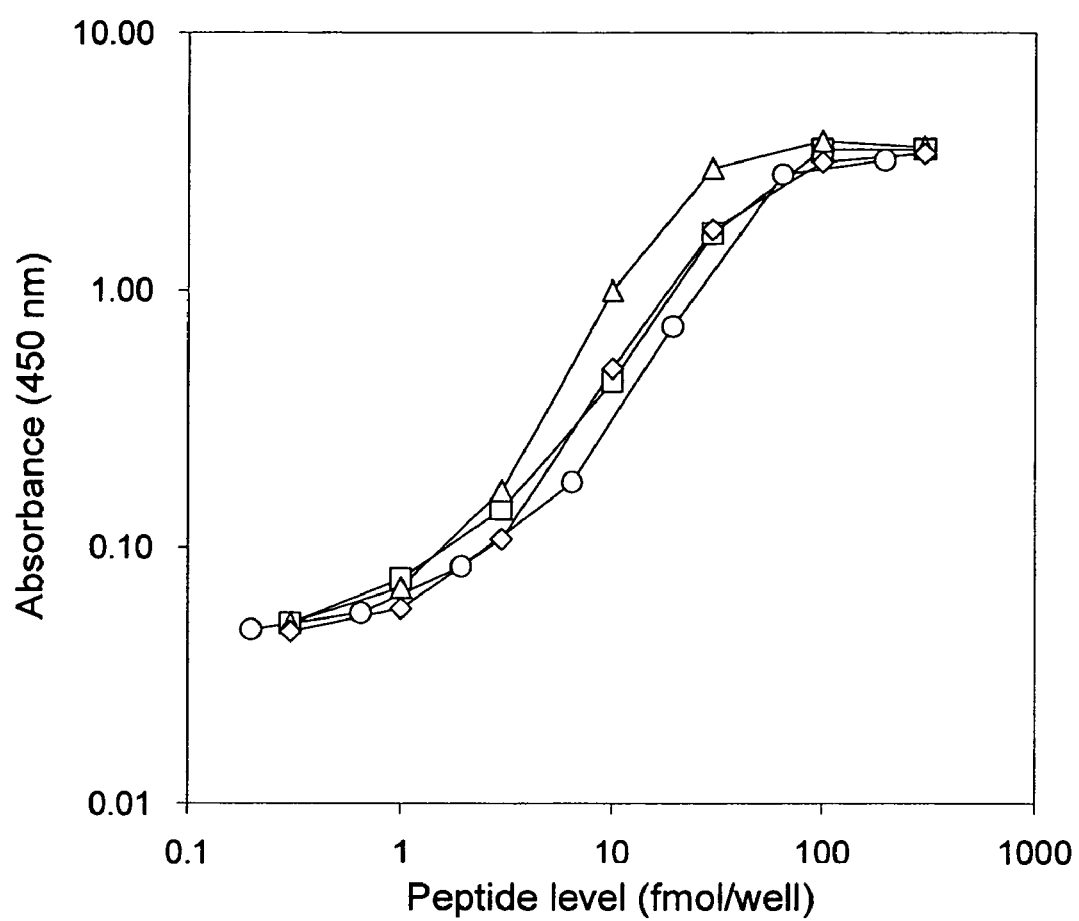
FIG. 26 shows absorbance at 450 nm when human NPW30, rat NPW30, mouse NPW30 and porcine NPW30 were added to the EIA system using monoclonal antibody 2A1A in various levels. In the figure, -○- (-open circle-) indicates the case where human NPW30 was added, -□- (-open square-) indicates the case where rat NPW30 was added, -Δ- (-open triangle-) indicates the case where mouse NPW30 was added, and -◇- (-open diamond-) indicates the case where porcine NPW30 was added, respectively.
Figure 27:
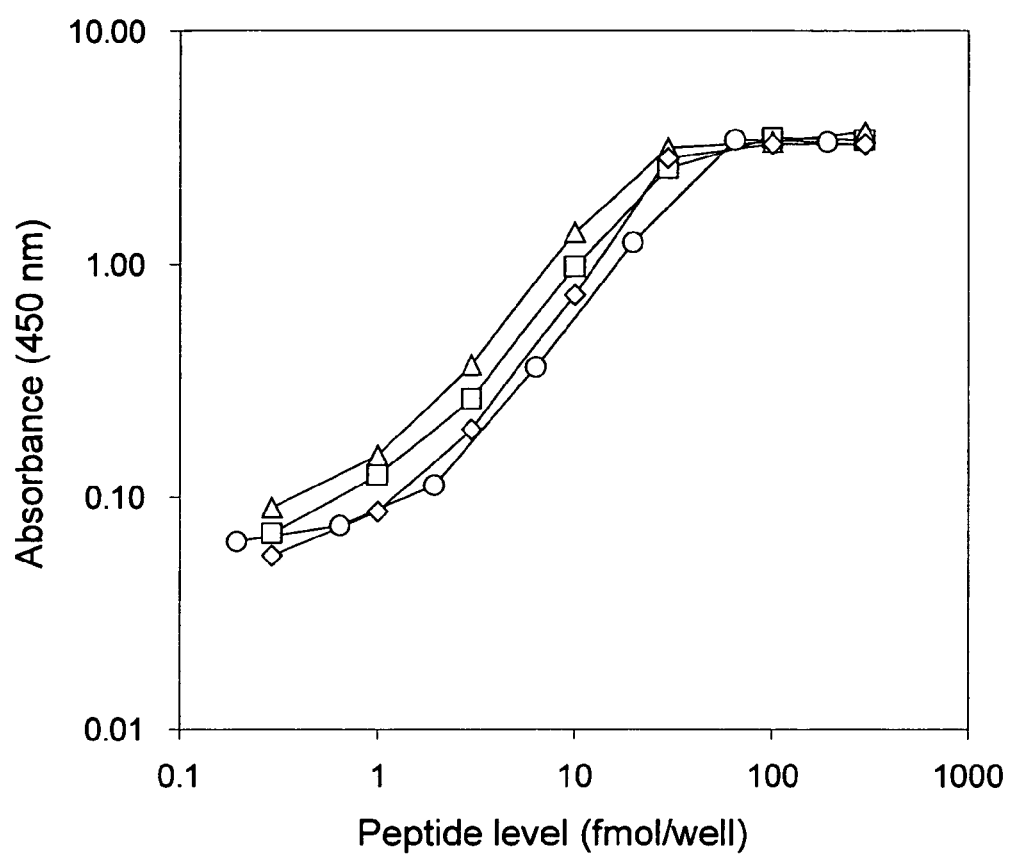
FIG. 27 shows absorbance at 450 nm when human NPW30, rat NPW30, mouse NPW30 and porcine NPW30 were added to the EIA system using monoclonal antibody 3A1A in various levels. In the figure, -○- (-open circle-) indicates the case where human NPW30 was added, -□- (-open square-) indicates the case where rat NPW30 was added, -△- (-open triangle-) indicates the case where mouse NPW30 was added, and -◇- (-open diamond-) indicates the case where porcine NPW30 was added, respectively.
Figure 28:
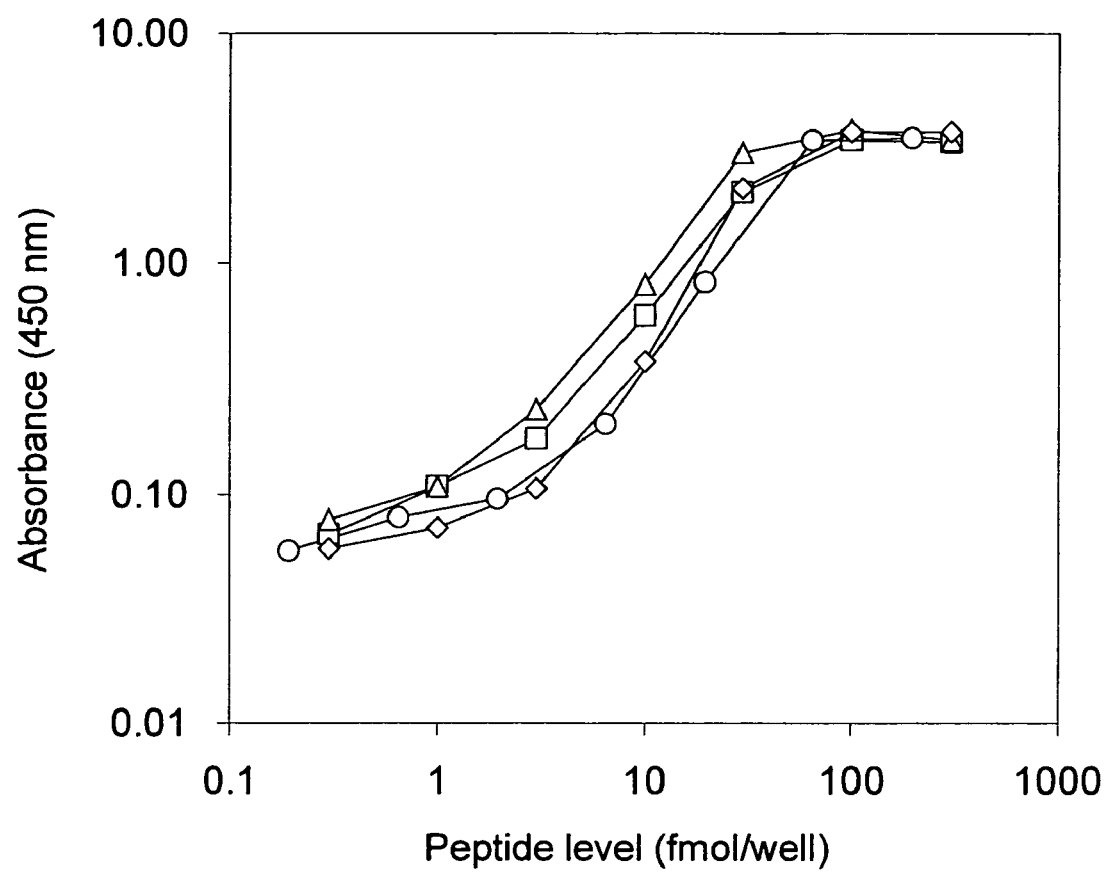
FIG. 28 shows absorbance at 450 μm when human NPW30, rat NPW30, mouse NPW30 and porcine NPW30 were added to the EIA system using monoclonal antibody 7F2-E8 in various levels. In the figure, -○- (-open circle-) indicates the case where human NPW30 was added, -□- (-open square-) indicates the case where rat NPW30 was added, -△- (-open triangle-) indicates the case where mouse NPW30 was added, and -◇- (-open diamond-) indicates the case where porcine NPW30 was added, respectively.

Three monoclonal antibodies 2A1A, 3A1A or 7F2-E8 binding to the carboxyl terminal region of NPW30 were dissolved in 50 mM carbonate buffer (pH 9.6) in 10 μg/ml, and 100 μl of the antibody solution was added to each well of a 96-well immunoplate (NUNC). The plate was left to stand at 4° C. for 16 hours. The solution in the well was then discarded and 200 μl/well of Block Ace was added to the well. The plate was stored at 4° C. until used. The NPW solution was diluted with the EIA buffer described in EXAMPLE 1-(10) in various concentrations and 100 μl of the dilution was added to each well. This plate was then left to stand at 4° C. for 16 hours. After the plate was washed 3 times with PBS, 100 μl of a HRP-labeled 2G6-D1 dilution in EIA buffer in fixed magnifications (300 to 1000-fold) was added to each well. The plate was then left to stand at 4° C. for 16 hours. After the plate was washed 4 times with PBS, 100 μl of the TMB Microwell Peroxidase Substrate System was added thereto to react them at room temperature. After the reaction was terminated by adding 50 μl of 1M phosphoric acid, the absorbance was measured at 450 nm on the plate reader. Increased absorbance at 450 nm was noted dependently on each of the peptide levels of human NPW30 (SEQ ID NO: 5), rat NPW30 (SEQ ID NO: 7), mouse NPW30 (SEQ ID NO: 9) and porcine NPW30 (SEQ ID NO: 11) added in the respective double antibody EIA systems. The results obtained using the monoclonal antibodies 2A1A, 3A1A and 7F2-E8 are shown in FIGS. 26, 27 and 28, respectively.

Using these double antibody EIA systems, a minimum of 1 fmol of NPW30 could be detected.

INDUSTRIAL APPLICABILITY

The antibody of the present invention has an extremely high binding affinity to NPW, can neutralize the intracellular cAMP production inhibiting activity of NPW and also has an eating stimulation action, prolactin production inhibiting action, diuretic action and gastric acid secretion inhibiting action.

Therefore, the antibody of the present invention inhibits the action of NPW and can thus be used as a safe pharmaceutical such as an agent for preventing/treating, for example, anorexia, pituitary tumor, diencephalon tumor, menstrual disorder, autoimmune disease, prolactinoma, sterility, impotence, amenorrhea, lactorrhea, acromegaly, Chiari-Frommel syndrome, Argonz-del Castillo syndrome, Forbes-Albright syndrome, lymphoma, Sheehan's syndrome, spermatogenesis disorder, renal dropsy, voiding dysfunction (e.g., bladder contractile dysfunction, obstruction of urethral flow, dysuria, urodynia, urinary obstruction, etc.), hyponatremia, syndrome of inappropriate secretion of anti-diuretic hormone (SIADH), hypertension, upper digestive tract disorders (e.g., peptic ulcer (e.g., gastric ulcer, duodenal ulcer, marginal ulcer, Zollinger-Ellison syndrome, etc.), gastritis, reflux esophagitis, NUD (non-ulcer dyspepsia), gastric cancer, gastric MALT lymphoma, nonsteroidal anti-inflammatory drug-induced ulcer, hyperacidity, ulcer, etc.) or the like; an eating (appetite) stimulant, etc.

By the assay method using the antibody of the present invention, preferably by immunoassay based on the sandwich method using the monoclonal antibody specifically recognizing the C-terminus of NPW and the monoclonal antibody specifically recognizing the N-terminus of NPW, etc., the NPW can be quantified with high sensitivity and specificity, and thus can be used for diagnosis of diseases associated with NPW [for example, anorexia, obesity (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity, etc.), pituitary tumor, diencephalon tumor, menstrual disorder, autoimmune disease, prolactinoma, sterility, impotence, amenorrhea, lactorrhea, acromegaly, Chiari-Frommel syndrome, Argonz-del Castillo syndrome, Forbes-Albright syndrome, lymphoma, Sheehan's syndrome, spermatogenesis disorder, renal dropsy, voiding dysfunction (e.g., bladder contractile dysfunction, obstruction of urethral flow, dysuria, urodynia, urinary obstruction, etc.), hyponatremia, syndrome of inappropriate secretion of anti-diuretic hormone (SIADH), hypertension, storage dysfunction (e.g., pollakiuria, urinary incontinence (e.g., urge incontinence, stress incontinence, functional incontinence, etc.)), polyuria, diabetes insipidus (e.g., pituitary diabetes insipidus, renal diabetes insipidus, etc.), hypernatremia, metabolic alkalosis, hypokalemia, Cushing's syndrome, upper digestive tract disorders (e.g., peptic ulcer (e.g., gastric ulcer, duodenal ulcer, marginal ulcer, Zollinger-Ellison syndrome, etc.), gastritis, reflux esophagitis, NUD (non-ulcer dyspepsia), gastric cancer, gastric MALT lymphoma, nonsteroidal anti-inflammatory drug-induced ulcer, hyperacidity, ulcer, etc.), dyspepsia (e.g., pituitary dyspepsia, renal dyspepsia, etc.), bone metabolism disorders (e.g., osteoporosis, osteomalacia, etc.), anemia (e.g., iron deficiency anemia, etc.). Besides, the antibody of the present invention can be used for immuno-tissue staining of the NPW.

The invention claimed is:

1. A monoclonal antibody which specifically reacts with a partial peptide at the N-terminal region of a polypeptide comprising the amino acid sequence of SEQ ID NO: 4 or a salt thereof, and does not recognize the partial peptide at the C-terminal region of the polypeptide or a salt thereof; specifically reacts with a peptide comprising (i) the 1st-6th ammo acid sequences, (ii) the 2nd-7th amino acid sequences, (iii) the 3rd-8th amino acid sequences or (iv) the 4th-9th amino acid sequences in the amino acid sequence of SEQ ID NO:4; and has a neutralizing activity for the polypeptide comprising the amino acid sequence of SEQ ID NO: 4.

2. The antibody according to claim 1, which is labeled.

3. The antibody represented by AhW23N2G6D1a producible from a hybridoma represented by AhW23N2G6D1 (FERM BP-8363).

4. An antibody specifically reacting with a binding site of the antibody according to claim 3 to a polypeptide comprising the amino acid sequence represented by SEQ ID NO: 4.

5. The antibody according to claim 4, which has a neutralizing activity for a polypeptide comprising the amino acid sequence represented by SEQ ID NO: 4.

6. The antibody represented by AhW23N3H3E4a producible from a hybridoma represented by AhW23N3H3E4 (FERM BP-8364).

7. An antibody specifically reacting with a binding site of the antibody according to claim 6 to a polypeptide comprising the amino acid sequence represented by SEQ ID NO: 4.

8. The antibody according to claim 7, which has a neutralizing activity for a polypeptide comprising the amino acid sequence represented by SEQ ID NO: 4.

9. A pharmaceutical comprising the antibody according to claim 1.

10. The pharmaceutical according to claim 9, which is an agent for preventing/treating sterility, renal dropsy, peptic ulcer or hyperchlorhydria.

11. A diagnostic agent comprising the antibody according to claim 1.

* * * * *

SEQUENCE LISTING

<160> NUMBER OF SEQ ID NOS: 20

<210> SEQ ID NO 1
<211> LENGTH: 14
<212> TYPE: PRT
<213> ORGANISM: Artificial Sequence
<220> FEATURE:
<223> OTHER INFORMATION: immunogen

<400> SEQUENCE: 1

Trp Tyr Lys His Val Ala Ser Pro Arg Tyr His Thr Val Cys
                 5                  10

<210> SEQ ID NO 2
<211> LENGTH: 14
<212> TYPE: PRT
<213> ORGANISM: Artificial Sequence
<220> FEATURE:
<223> OTHER INFORMATION: immunogen

<400> SEQUENCE: 2

Cys His Thr Val Gly Arg Ala Ala Gly Leu Leu Met Gly Leu
                 5                  10

<210> SEQ ID NO 3
<211> LENGTH: 16
<212> TYPE: PRT
<213> ORGANISM: Artificial Sequence
<220> FEATURE:
<223> OTHER INFORMATION: immunogen

<400> SEQUENCE: 3

Cys Ala Ser Gly Leu Leu Met Gly Leu Arg Arg Ser Pro Tyr Leu Trp
                 5                  10                  15

<210> SEQ ID NO 4
<211> LENGTH: 23
<212> TYPE: PRT
<213> ORGANISM: Homo sapiens

<400> SEQUENCE: 4

Trp Tyr Lys His Val Ala Ser Pro Arg Tyr His Thr Val Gly Arg Ala
1               5                   10                  15

Ala Gly Leu Leu Met Gly Leu
            20

<210> SEQ ID NO 5
<211> LENGTH: 30
<212> TYPE: PRT
<213> ORGANISM: Homo sapiens

<400> SEQUENCE: 5

Trp Tyr Lys His Val Ala Ser Pro Arg Tyr His Thr Val Gly Arg Ala
1               5                   10                  15

Ala Gly Leu Leu Met Gly Leu Arg Arg Ser Pro Tyr Leu Trp
            20                  25                  30

<210> SEQ ID NO 6
<211> LENGTH: 23
<212> TYPE: PRT
<213> ORGANISM: Rattus norvegicus

<400> SEQUENCE: 6

Trp Tyr Lys His Val Ala Ser Pro Arg Tyr His Thr Val Gly Arg Ala
1               5                   10                  15

Ser Gly Leu Leu Met Gly Leu
            20

<210> SEQ ID NO 7
<211> LENGTH: 30
<212> TYPE: PRT
<213> ORGANISM: Rattus norvegicus

<400> SEQUENCE: 7

Trp Tyr Lys His Val Ala Ser Pro Arg Tyr His Thr Val Gly Arg Ala
1               5                   10                  15

Ser Gly Leu Leu Met Gly Leu Arg Arg Ser Pro Tyr Leu Trp
            20                  25                  30

<210> SEQ ID NO 8
<211> LENGTH: 23
<212> TYPE: PRT
<213> ORGANISM: Mus musculus

<400> SEQUENCE: 8

Trp Tyr Lys His Val Ala Ser Pro Arg Tyr His Thr Val Gly Arg Ala
1               5                   10                  15

Ser Gly Leu Leu Met Gly Leu
            20

<210> SEQ ID NO 9
<211> LENGTH: 30
<212> TYPE: PRT
<213> ORGANISM: Mus musculus

<400> SEQUENCE: 9

Trp Tyr Lys His Val Ala Ser Pro Arg Tyr His Thr Val Gly Arg Ala
1               5                   10                  15

Ser Gly Leu Leu Met Gly Leu Arg Arg Ser Pro Tyr Gln Trp
            20                  25                  30

<210> SEQ ID NO 10
<211> LENGTH: 23
<212> TYPE: PRT
<213> ORGANISM: Sus scrofa

<400> SEQUENCE: 10

Trp Tyr Lys His Thr Ala Ser Pro Arg Tyr His Thr Val Gly Arg Ala
1               5                   10                  15

Ala Gly Leu Leu Met Gly Leu
            20

<210> SEQ ID NO 11
<211> LENGTH: 30
<212> TYPE: PRT
<213> ORGANISM: Sus scrofa

<400> SEQUENCE: 11

Trp Tyr Lys His Thr Ala Ser Pro Arg Tyr His Thr Val Gly Arg Ala
1               5                   10                  15

Ala Gly Leu Leu Met Gly Leu Arg Arg Ser Pro Tyr Met Trp
            20                  25                  30

<210> SEQ ID NO 12
<211> LENGTH: 14

```
<212> TYPE: PRT
<213> ORGANISM: Artificial Sequence
<220> FEATURE:
<223> OTHER INFORMATION: Biotin-labeled peptide
<220> FEATURE:
<221> NAME/KEY: MOD_RES
<222> LOCATION: 14
<223> OTHER INFORMATION: Xaa means biotin-labeled Cys modified with
      Biotin (Long Arm) Maleimide (Vector Laboratories).

<400> SEQUENCE: 12

Trp Tyr Lys His Val Ala Ser Pro Arg Tyr His Thr Val Xaa
                  5                  10

<210> SEQ ID NO 13
<211> LENGTH: 14
<212> TYPE: PRT
<213> ORGANISM: Artificial Sequence
<220> FEATURE:
<223> OTHER INFORMATION: Biotin-labeled peptide
<220> FEATURE:
<221> NAME/KEY: MOD_RES
<222> LOCATION: 1
<223> OTHER INFORMATION: Xaa means biotin-labeled Cys modified with
      Biotin (Long Arm) Maleimide (Vector Laboratories).

<400> SEQUENCE: 13

Xaa His Thr Val Gly Arg Ala Ala Gly Leu Leu Met Gly Leu
                  5                  10

<210> SEQ ID NO 14
<211> LENGTH: 16
<212> TYPE: PRT
<213> ORGANISM: Artificial Sequence
<220> FEATURE:
<223> OTHER INFORMATION: Biotin-labeled peptide
<220> FEATURE:
<221> NAME/KEY: MOD_RES
<222> LOCATION: 1
<223> OTHER INFORMATION: Xaa means biotin-labeled Cys modified with
      Biotin (Long Arm) Maleimide (Vector Laboratories).

<400> SEQUENCE: 14

Xaa Ala Ser Gly Leu Leu Met Gly Leu Arg Arg Ser Pro Tyr Leu Trp
                  5                  10                  15

<210> SEQ ID NO 15
<211> LENGTH: 328
<212> TYPE: PRT
<213> ORGANISM: Homo sapiens

<400> SEQUENCE: 15

Met Asp Asn Ala Ser Phe Ser Glu Pro Trp Pro Ala Asn Ala Ser Gly
1               5                   10                  15

Pro Asp Pro Ala Leu Ser Cys Ser Asn Ala Ser Thr Leu Ala Pro Leu
            20                  25                  30

Pro Ala Pro Leu Ala Val Ala Val Pro Val Val Tyr Ala Val Ile Cys
        35                  40                  45

Ala Val Gly Leu Ala Gly Asn Ser Ala Val Leu Tyr Val Leu Leu Arg
    50                  55                  60

Ala Pro Arg Met Lys Thr Val Thr Asn Leu Phe Ile Leu Asn Leu Ala
65                  70                  75                  80

Ile Ala Asp Glu Leu Phe Thr Leu Val Leu Pro Ile Asn Ile Ala Asp
                85                  90                  95

Phe Leu Leu Arg Gln Trp Pro Phe Gly Glu Leu Met Cys Lys Leu Ile
            100                 105                 110
```

```
Val Ala Ile Asp Gln Tyr Asn Thr Phe Ser Ser Leu Tyr Phe Leu Thr
        115                 120                 125

Val Met Ser Ala Asp Arg Tyr Leu Val Val Leu Ala Thr Ala Glu Ser
    130                 135                 140

Arg Arg Val Ala Gly Arg Thr Tyr Ser Ala Ala Arg Ala Val Ser Leu
145                 150                 155                 160

Ala Val Trp Gly Ile Val Thr Leu Val Val Leu Pro Phe Ala Val Phe
                165                 170                 175

Ala Arg Leu Asp Asp Glu Gln Gly Arg Arg Gln Cys Val Leu Val Phe
            180                 185                 190

Pro Gln Pro Glu Ala Phe Trp Trp Arg Ala Ser Arg Leu Tyr Thr Leu
        195                 200                 205

Val Leu Gly Phe Ala Ile Pro Val Ser Thr Ile Cys Val Leu Tyr Thr
    210                 215                 220

Thr Leu Leu Cys Arg Leu His Ala Met Arg Leu Asp Ser His Ala Lys
225                 230                 235                 240

Ala Leu Glu Arg Ala Lys Lys Arg Val Thr Phe Leu Val Val Ala Ile
                245                 250                 255

Leu Ala Val Cys Leu Leu Cys Trp Thr Pro Tyr His Leu Ser Thr Val
            260                 265                 270

Val Ala Leu Thr Thr Asp Leu Pro Gln Thr Pro Leu Val Ile Ala Ile
        275                 280                 285

Ser Tyr Phe Ile Thr Ser Leu Ser Tyr Ala Asn Ser Cys Leu Asn Pro
    290                 295                 300

Phe Leu Tyr Ala Phe Leu Asp Ala Ser Phe Arg Arg Asn Leu Arg Gln
305                 310                 315                 320

Leu Ile Thr Cys Arg Ala Ala Ala
                325

<210> SEQ ID NO 16
<211> LENGTH: 984
<212> TYPE: DNA
<213> ORGANISM: Homo sapiens

<400> SEQUENCE: 16
atggacaacg cctcgttctc ggagccctgg cccgccaacg catcgggccc ggacccggcg      60
ctgagctgct ccaacgcgtc gactctggcg ccgctgccgg cgccgctggc ggtggctgta     120
ccagttgtct acgcggtgat ctgcgccgtg ggtctggcgg caactccgc cgtgctgtac     180 gtgttgctgc gggcgccccg catgaagacc gtcaccaacc tgttcatcct caacctggcc     240
atcgccgacg agctcttcac gctggtgctg cccatcaaca tcgccgactt cctgctgcgg     300
cagtggccct cggggagct catgtgcaag ctcatcgtgg ctatcgacca gtacaacacc     360
ttctccagcc tctacttcct caccgtcatg agcgccgacc gctacctggt ggtgttggcc     420
actgcggagt cgcgccgggt ggccggccgc acctacagcg ccgcgcgcgc ggtgagcctg     480
gccgtgtggg gatcgtcac actcgtcgtg ctgcccttcg cagtcttcgc ccggctagac     540
gacgagcagg gccggcgcca gtgcgtgcta gtctttccgc agcccgaggc cttctggtgg     600
cgcgcgagcc gcctctacac gctcgtgctg ggcttcgcca tcccgtgtc caccatctgt     660 gtcctctata ccaccctgct gtgccggctg catgccatgc ggctggacag ccacgccaag     720
gccctggagc gcgccaagaa gcgggtgacc ttcctggtgg tggcaatcct ggcggtgtgc     780
ctcctctgct ggacgcccta ccacctgagc accgtggtgg cgctcaccac cgacctcccg     840
```

```
cagacgccgc tggtcatcgc tatctcctac ttcatcacca gcctgagcta cgccaacagc    900
tgcctcaacc ccttcctcta cgccttcctg gacgccagct ccgcaggaa cctccgccag    960 ctgataactt gccgcgcggc agcc                                          984
```

```
<210> SEQ ID NO 17
<211> LENGTH: 333
<212> TYPE: PRT
<213> ORGANISM: Homo sapiens

<400> SEQUENCE: 17
```

Met Gln Ala Ala Gly His Pro Glu Pro Leu Asp Ser Arg Gly Ser Phe
1               5                   10                  15

Ser Leu Pro Thr Met Gly Ala Asn Val Ser Gln Asp Asn Gly Thr Gly
            20                  25                  30

His Asn Ala Thr Phe Ser Glu Pro Leu Pro Phe Leu Tyr Val Leu Leu
        35                  40                  45

Pro Ala Val Tyr Ser Gly Ile Cys Ala Val Gly Leu Thr Gly Asn Thr
    50                  55                  60

Ala Val Ile Leu Val Ile Leu Arg Ala Pro Lys Met Lys Thr Val Thr
65                  70                  75                  80

Asn Val Phe Ile Leu Asn Leu Ala Val Ala Asp Gly Leu Phe Thr Leu
                85                  90                  95

Val Leu Pro Val Asn Ile Ala Glu His Leu Leu Gln Tyr Trp Pro Phe
            100                 105                 110

Gly Glu Leu Leu Cys Lys Leu Val Leu Ala Val Asp His Tyr Asn Ile
        115                 120                 125

Phe Ser Ser Ile Tyr Phe Leu Ala Val Met Ser Val Asp Arg Tyr Leu
    130                 135                 140

Val Val Leu Ala Thr Val Arg Ser Arg His Met Pro Trp Arg Thr Tyr
145                 150                 155                 160

Arg Gly Ala Lys Val Ala Ser Leu Cys Val Trp Leu Gly Val Thr Val
                165                 170                 175

Leu Val Leu Pro Phe Phe Ser Phe Ala Gly Val Tyr Ser Asn Glu Leu
            180                 185                 190

Gln Val Pro Ser Cys Gly Leu Ser Phe Pro Trp Pro Glu Gln Val Trp
        195                 200                 205

Phe Lys Ala Ser Arg Val Tyr Thr Leu Val Leu Gly Phe Val Leu Pro
    210                 215                 220

Val Cys Thr Ile Cys Val Leu Tyr Thr Asp Leu Leu Arg Arg Leu Arg
225                 230                 235                 240

Ala Val Arg Leu Arg Ser Gly Ala Lys Ala Leu Gly Lys Ala Arg Arg
                245                 250                 255

Lys Val Thr Val Leu Val Leu Val Val Leu Ala Val Cys Leu Leu Cys
            260                 265                 270

Trp Thr Pro Phe His Leu Ala Ser Val Val Ala Leu Thr Thr Asp Leu
        275                 280                 285

Pro Gln Thr Pro Leu Val Ile Ser Met Ser Tyr Val Ile Thr Ser Leu
    290                 295                 300

Ser Tyr Ala Asn Ser Cys Leu Asn Pro Phe Leu Tyr Ala Phe Leu Asp
305                 310                 315                 320

Asp Asn Phe Arg Lys Asn Phe Arg Ser Ile Leu Arg Cys
                325                 330

```
<210> SEQ ID NO 18
```

<211> LENGTH: 999
<212> TYPE: DNA
<213> ORGANISM: Homo sapiens

<400> SEQUENCE: 18

```
atgcaggccg ctgggcaccc agagcccctt gacagcaggg gctccttctc cctccccacg      60
atgggtgcca acgtctctca ggacaatggc actggccaca atgccacctt ctccgagcca     120
ctgccgttcc tctatgtgct cctgcccgcc gtgtactccg ggatctgtgc gtgggggctg     180
actggcaaca cggccgtcat ccttgtaatc ctaagggcgc ccaagatgaa gacggtgacc     240
aacgtgttca tcctgaacct ggccgtcgcc gacgggctct tcacgctggt actgcccgtc     300
aacatcgcgg agcacctgct gcagtactgg cccttcgggg agctgctctg caagctggtg     360
ctggccgtcg accactacaa catcttctcc agcatctact ccctagccgt gatgagcgtg     420
gaccgatacc tggtggtgct ggccaccgtg aggtcccgcc acatgccctg gcgcacctac     480
cggggggcga aggtcgccag cctgtgtgtc tggctgggcg tcacggtcct ggttctgccc     540
ttcttctctt tcgctggcgt ctacagcaac gagctgcagg tcccaagctg tgggctgagc     600
ttcccgtggc ccgagcaggt ctggttcaag gccagccgtg tctacacgtt ggtcctgggc     660
ttcgtgctgc ccgtgtgcac catctgtgtg ctctacacag acctcctgcg caggctgcgg     720
gccgtgcggc tccgctctgg agccaaggct ctaggcaagg ccaggcggaa ggtgaccgtc     780
ctggtcctcg tcgtgctggc cgtgtgcctc ctctgctgga cgcccttcca cctggcctct     840
gtcgtggccc tgaccacgga cctgcccag accccactgg tcatcagtat gtcctacgtc     900
atcaccagcc tcagctacgc caactcgtgc ctgaaccccc tcctctacgc ctttctagat     960
gacaacttcc ggaagaactt ccgcagcata ttgcggtgc                           999
```

<210> SEQ ID NO 19
<211> LENGTH: 329
<212> TYPE: PRT
<213> ORGANISM: Rattus norvegicus

<400> SEQUENCE: 19

```
Met His Asn Leu Ser Leu Phe Glu Pro Gly Arg Gly Asn Val Ser Cys
                5                   10                  15
Gly Gly Pro Phe Leu Gly Cys Pro Asn Glu Ser Asn Pro Ala Pro Leu
            20                  25                  30
Pro Leu Pro Gln Pro Leu Ala Val Ala Val Pro Val Val Tyr Gly Val
        35                  40                  45
Ile Cys Ala Val Gly Leu Ala Gly Asn Ser Ala Val Leu Tyr Val Leu
    50                  55                  60
Leu Arg Thr Pro Arg Met Lys Thr Val Thr Asn Val Phe Ile Leu Asn
65                  70                  75                  80
Leu Ala Ile Ala Asp Glu Leu Phe Thr Leu Val Leu Pro Ile Asn Ile
                85                  90                  95
Ala Asp Phe Leu Leu Arg Arg Trp Pro Phe Gly Glu Val Met Cys Lys
            100                 105                 110
Leu Ile Val Ala Val Asp Gln Tyr Asn Thr Phe Ser Ser Leu Tyr Phe
        115                 120                 125
Leu Ala Val Met Ser Ala Asp Arg Tyr Leu Val Val Leu Ala Thr Ala
    130                 135                 140
Glu Ser Arg Arg Val Ser Gly Arg Thr Tyr Gly Ala Ala Arg Ala Val
145                 150                 155                 160
Ser Leu Ala Val Trp Ala Leu Val Thr Leu Val Val Leu Pro Phe Ala
```

```
                165                 170                 175
Val Phe Ala Arg Leu Asp Glu Glu Gln Gly Arg Arg Gln Cys Val Leu
            180                 185                 190

Val Phe Pro Gln Pro Glu Ala Phe Trp Trp Arg Ala Ser Arg Leu Tyr
            195                 200                 205

Thr Leu Val Leu Gly Phe Ala Ile Pro Val Ser Thr Ile Cys Ala Leu
            210                 215                 220

Tyr Ile Thr Leu Leu Cys Arg Leu Arg Ala Ile Gln Leu Asp Ser His
225                 230                 235                 240

Ala Lys Ala Leu Asp Arg Ala Lys Lys Arg Val Thr Leu Val Val
            245                 250                 255

Ala Ile Leu Ala Val Cys Leu Leu Cys Trp Thr Pro Tyr His Leu Ser
            260                 265                 270

Thr Ile Val Ala Leu Thr Thr Asp Leu Pro Gln Thr Pro Leu Val Ile
            275                 280                 285

Gly Ile Ser Tyr Phe Ile Thr Ser Leu Ser Tyr Ala Asn Ser Cys Leu
            290                 295                 300

Asn Pro Phe Leu Tyr Ala Phe Leu Asp Asp Ser Phe Arg Arg Ser Leu
305                 310                 315                 320

Arg Gln Leu Val Ser Cys Arg Thr Ala
                325

<210> SEQ ID NO 20
<211> LENGTH: 987
<212> TYPE: DNA
<213> ORGANISM: Rattus norvegicus

<400> SEQUENCE: 20
atgcacaact tgtcgctctt cgagcctggc aggggcaatg tgtcttgcgg cggcccattt    60
ttgggctgtc ctaacgagtc gaacccagcg cctctgccac tgccgcagcc tctggcggta   120
gcagtgcctg tggtctacgg ggtgatctgc gcggtgggac tggcgggcaa ctccgcggtg   180
ctgtacgtac tgctgcgcac gccgcgcatg aagactgtta ccaacgtgtt cattctcaac   240
ctggctatcg cggacgagct cttcacctc gtgctgccca tcaacatcgc ggacttcctg   300
ctgaggcgct ggcccttcgg ggaagtcatg tgcaagctca tcgtggctgt cgaccagtac   360
aacactttct ctagcctcta cttcctcgcc gtcatgagcg cagaccgcta cctggttgtc   420
ctggccacag ccgagtcgcg ccgggtgtcc gggcgcactt atggtgcagc gcgggctgtc   480
agtctggcgg tgtgggcgct ggtgacattg gtcgtgctgc cttttgcggt attcgcccgg   540
ctggacgaag agcagggtcg gcgtcagtgc gtgctggtct cccgcagcc tgaggccttc   600 tggtggcgcg ccagccgtct gtacactcta gtgtttgggct tcgccatccc ggtgtccacc   660
atctgcgccc tctatatcac cctgttgtgc cgactgcgtg ctatccagct agacagccac   720
gccaaggccc tggaccgtgc caagaagcgc gtgaccttgt tggtggtggc gattctggct   780
gtgtgcctcc tctgctggac accgtaccac ctgagcacca tagtggcgct caccaccgac   840
ctcccgcaaa caccgttggt catcggcatc tcttacttca tcaccagtct gagctatgcc   900
aacagctgcc tcaaccctt cctctatgcc ttcctggacg acagcttccg caggagcctg   960
cggcagctgg tgtcatgccg cacagcc                                       987
```